US009758813B2

(12) United States Patent
Wangh et al.

(10) Patent No.: US 9,758,813 B2
(45) Date of Patent: *Sep. 12, 2017

(54) REAGENTS AND METHODS OF PCR

(71) Applicant: Brandeis University, Waltham, MA (US)

(72) Inventors: Lawrence J. Wangh, Auburndale, MA (US); John E. Rice, Quincy, MA (US); Nicholas Rice, Quincy, MA (US); Yanwei Jia, Waltham, MA (US)

(73) Assignee: Brandeis University, Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/715,299

(22) Filed: May 18, 2015

(65) Prior Publication Data

US 2015/0322503 A1   Nov. 12, 2015

Related U.S. Application Data

(63) Continuation of application No. 13/256,038, filed as application No. PCT/US2010/027011 on Mar. 11, 2010, now Pat. No. 9,034,605.

(60) Provisional application No. 61/202,565, filed on Mar. 12, 2009.

(51) Int. Cl.
*C12Q 1/68* (2006.01)

(52) U.S. Cl.
CPC ......... *C12Q 1/6806* (2013.01); *C12Q 1/6853* (2013.01)

(58) Field of Classification Search
CPC ........ C12Q 2527/107; C12Q 2531/107; C12Q 2545/114; C12Q 1/6806; C12Q 1/6853
USPC ...................................................... 435/91.2
See application file for complete search history.

(56) References Cited

U.S. PATENT DOCUMENTS

| 4,683,195 | A | 7/1987 | Mullis et al. |
| 4,683,202 | A | 7/1987 | Mullis |
| 4,965,188 | A | 10/1990 | Mullis et al. |
| 5,066,584 | A | 11/1991 | Gyllensten et al. |
| 5,338,671 | A | 8/1994 | Scalice et al. |
| 5,487,972 | A | 1/1996 | Gelfand et al. |
| 5,677,152 | A | 10/1997 | Birch et al. |
| 5,773,258 | A | 6/1998 | Birch et al. |
| 5,925,517 | A | 7/1999 | Tyagi et al. |
| 5,994,056 | A | 11/1999 | Higuchi |
| 6,020,130 | A | 2/2000 | Gold et al. |
| 6,150,097 | A | 11/2000 | Tyagi et al. |
| 6,277,607 | B1 | 8/2001 | Tyagi et al. |
| 9,034,605 | B2 * | 5/2015 | Wangh ............... C12Q 1/6806 435/91.2 |
| 2005/0242506 | A1 | 11/2005 | Yoseloff |
| 2006/0177841 | A1 | 8/2006 | Wangh et al. |
| 2006/0177842 | A1 * | 8/2006 | Wangh ............... C12Q 1/6848 435/6.12 |
| 2012/0088275 | A1 | 4/2012 | Wangh et al. |

FOREIGN PATENT DOCUMENTS

| WO | WO-03/054233 | 7/2003 |
| WO | WO-2004/090153 A2 | 10/2004 |
| WO | WO-2006/044994 A2 | 4/2006 |
| WO | WO-2006/044995 A1 | 4/2006 |
| WO | WO-2007/008728 A2 | 1/2007 |
| WO | WO-2008/044129 A2 | 4/2008 |
| WO | WO-2008/076324 A2 | 6/2008 |

OTHER PUBLICATIONS

Kainz., BioTechniques vol. 28, No. 2, pp. 278-282, 2000.*
Alllawi et al., "Thermodynamics and NMR of Internal G.T. Mismatches in DNA," Biochemistry, 36: 10581-10594 (1997).
Dang et al., "Oligonucleotide Inhibitors of Taq DNA Polymerase Facilitate Detection of Low Copy Number Targets by PCR," J Mol Biol, 264: 268-278 (1996).
Gyllensten et al., "Generation of Single-Stranded DNA by the Polymerase Chain Reaction and Its Application to Direct Sequencing of the HLA-DQA Locus," Proc Natl Acad Sci USA, 85: 7652-7656 (1988).
Haas et al., "Primer Design for Large Scale Sequencing," Nucl Acids Res, 26: 3006-3012 (1998).
Hillier et al., "OSP: A Computer Program for Choosing PCR and DNA Sequencing Primers," PCR Methods Appl, 1(2): 124-128 (1991).
Innis, "PCR Protocols, A Guide to Methods and Applications," Academic Press, San Diego, CA, 1990.
Kaboev et al., "PCR Hot Start Using Primers with the Structure of Molecular Beacons (Hairpin-like Structure)," Nucl Acids Res, 28(21): E94 (2000).

(Continued)

*Primary Examiner* — Cynthia B Wilder
(74) *Attorney, Agent, or Firm* — Foley Hoag LLP

(57) ABSTRACT

Modified double-stranded oligonucleotides that have terminal regions on each of their strands, that have a hybrid length of 6-50 nucleotides long, that have a melting temperature Tm of at least 32° C., and that include 2-4 modifying groups, each covalently attached to a different terminal region, preferably to a terminal nucleotide, said modifying groups being polycyclic substituents that do not have bulky portions that are non-planar, said modified oligonucleotide being capable of binding to the 5' exonuclease domains of DNA polymerases and, when included in a PCR or other primer-dependent DNA amplification reaction at a concentration, generally not more than 2000 nM, that is effective for at least one of the functions of suppressing mispriming, increasing polymerase selectivity against 3' terminal mismatches. Increasing polymerase selectivity against AT-rich 3' ends, reducing scatter among replicates, suppressing polymerase 5' exonuclease activity, and inhibiting polymerase activity; as well as amplification reaction mixtures containing such modified double-stranded oligonucleotides, and amplification reactions, amplification assays and kits that include such modified double-stranded oligonucleotides.

20 Claims, 49 Drawing Sheets

(56) References Cited

OTHER PUBLICATIONS

Li et al., "PRIMO: A Primer Design Program that Applies Base Quality Statistics for Automated Large-scale DNA Sequencing," Genomics, 40(3): 476-485 (1997).

Markham et al., "DINAMelt Web Server for Nucleic Acid Melting Prediction," Nucl Acids Res, 33: W577-W581 (2005).

Markham et al., "UNAFold: Software for Nucleic Acid Folding and Hybridization," Methods Mol Biol, 453: 1-33 (2008).

Newton et al., "Analysis of Any Point Mutation in DNA. The Amplification Refactory Mutation System (ARMS)," Nucl Acids Res, 17: 2503-2516 (1989).

Pierce et al., "Linear-After-The-Exponential (LATE)-PCR: Primer Design Criteria for High Yields of Specific Single-Stranded DNA and Improved Real-Time Detection," PNAS, 102: 8609-8614 (2005).

Proutski et al., "Primer Master: A New Program for the Design and Analysis of PCR Primers," Comput Appl Biosci, 12(3): 253-255 (1996).

Rice et al., "Monoplex/multiplex Linear-After-The-Exponential-PCR Assays Combined with PrimeSafe and Dilute-'N'-Go Sequencing bn," Nat Protoc, 2: 2429-2438 (2007).

Rychlik et al., "A Computer Program for Choosing Optimal Oligonucleotides for Filter Hybridization, Sequencing and in Vitro Amplification of DNA," Nucl Acids Res, 17(21): 8543-8551 (1989).

Sanchez et al., "Linear-After-The-Expontential (LATE)-PCR: An Advanced Method of Asymmetric PCR and Its Uses in Quantitative Real-Time Analysis," Proc Natl Acad Sci USA, 101(7): 1933-1938 (2004).

Santalucia et al., "A Unified View of Polymer, Dumbbell, and Oligonucleotide DNA Nearest-Neighbor Thermodynamics," PNAS, 95: 1460-1465 (1998).

Wu et al., "Allele-Specific Enzymatic Amplification of Beta-Globin Genomic DNA for Diagnosis of Sickle Cell Anemia," Proc Natl Acad Sci USA, 86: 2757-2760 (1989).

Xu et al., "Real-time Quantiative Assay of HCV RNA Using the Duplex Scorpion Primer," Arch Virol, 152(2): 431-440 (2007).

\* cited by examiner

Lane Nos. 1 2 3

SEQUENCE LISTING

<160> NUMBER OF SEQ ID NOS: 165

<210> SEQ ID NO 1
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1
cctggattat gcctggcacc at                                           22

<210> SEQ ID NO 2
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 2
ccttgatgac gcttctgtat cta                                          23

<210> SEQ ID NO 3
<211> LENGTH: 84
<212> TYPE: DNA
<213> ORGANISM: Unknown
<220> FEATURE:
<221> NAME/KEY: source
<223> OTHER INFORMATION: /note="Description of Unknown: Target
      polynucleotide"

<400> SEQUENCE: 3
cctggattat gcctggcacc attaaagaaa atatcatctt tggtgtttcc tatgatgaat    60
atagatacag aagcgtcatc aaag                                          84

<210> SEQ ID NO 4
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 4
cacgacctcg ccgacc                                                   16

<210> SEQ ID NO 5
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 5
cacgacctcg ctgacc                                                   16

<210> SEQ ID NO 6
<211> LENGTH: 16
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 6
cacgacctcg ctgacc                                                        16

<210> SEQ ID NO 7
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 7
cacgacctcg ctgacc                                                        16

<210> SEQ ID NO 8
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 8
cacgacctcg ctgacc                                                        16

<210> SEQ ID NO 9
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 9
ggagcaaaat agcaatgagg ta                                                 22

<210> SEQ ID NO 10
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 10
ggtcagatga aaatgatacg tg                                                 22

<210> SEQ ID NO 11
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 11
ggtcagatga aaatgatacg tg                                                 22
```

```
<210> SEQ ID NO 12
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 12
gaaataaaat aaaaataaaa ta                                              22

<210> SEQ ID NO 13
<211> LENGTH: 8
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 13 cagccggc                                                               8

<210> SEQ ID NO 14
<211> LENGTH: 8
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 14 ccgccggc                                                               8

<210> SEQ ID NO 15
<211> LENGTH: 11
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 15
gcgtacgcag g                                                          11

<210> SEQ ID NO 16
<211> LENGTH: 11
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 16
gcgtacgaag g                                                          11

<210> SEQ ID NO 17
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 17
ggagcaaaat agcaatgagg ta                                             22

<210> SEQ ID NO 18
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 18
tgagagatga aaatgatcga gt                                             22

<210> SEQ ID NO 19
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 19
ggtcagatga aaatgatacg tg                                             22

<210> SEQ ID NO 20
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 20
aaattgcgtc attgtttcac agggcca                                        27

<210> SEQ ID NO 21
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 21
aatctgggtg gtggtcatac                                                20

<210> SEQ ID NO 22
<211> LENGTH: 192
<212> TYPE: DNA
<213> ORGANISM: Unknown
<220> FEATURE:
<221> NAME/KEY: source
<223> OTHER INFORMATION: /note="Description of Unknown: Target
      polynucleotide"

<400> SEQUENCE: 22
aatctgggtg gtggtcatac aggtcatcac tgtaaaattc tttgaacttt tctgtatata    60
tctttgaaaa ttttggaaaa aaaatgttgg aaaacttaaa aggctgttgc tttgctcata   120
ttggcggtac atatacaaaa gtggaaagga tgagattgat tggcatggcc ctgtgaaaca   180
atgacgcaat tt                                                         192

<210> SEQ ID NO 23
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 23
ggagcaaaat agcaatgagg ta                                              22

<210> SEQ ID NO 24
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 24
ggagcaaaat agcaatgagg ta                                              22

<210> SEQ ID NO 25
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 25
ggagcaaaat agcaatgagg ta                                              22

<210> SEQ ID NO 26
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 26
ggagcaaaat agcaatgagg ta                                              22

<210> SEQ ID NO 27
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 27
ggagcaaaat agcaatgagg ta                                              22

<210> SEQ ID NO 28
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 28
ggagcaaaat agcaatgagg ta                                              22

<210> SEQ ID NO 29
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 29
ggagcaaaat agcaatgagg ta                                              22

<210> SEQ ID NO 30
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 30
ggagcaaaat agcaatgagg ta                                              22

<210> SEQ ID NO 31
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 31
ggagcaaaat agcaatgagg ta                                              22

<210> SEQ ID NO 32
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 32
ggagcaaaat agcaatgagg ta                                              22

<210> SEQ ID NO 33
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 33
ggagcaaaat agcaatgagg ta                                              22

<210> SEQ ID NO 34

```
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 34
cgtaagatta caatggcagg ctccagt                                        27

<210> SEQ ID NO 35
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 35
gcccaagttt tatcgttctt ctca                                           24

<210> SEQ ID NO 36
<211> LENGTH: 95
<212> TYPE: DNA
<213> ORGANISM: Unknown
<220> FEATURE:
<221> NAME/KEY: source
<223> OTHER INFORMATION: /note="Description of Unknown: Target
      polynucleotide"

<400> SEQUENCE: 36
cgtaagatta caatggcagg ctccagaagg ttctaagtgc catgatacaa gcttcccaat    60
tactaagtat gctgagaaga acgataaaac ttggg                               95

<210> SEQ ID NO 37
<211> LENGTH: 98
<212> TYPE: DNA
<213> ORGANISM: Unknown
<220> FEATURE:
<221> NAME/KEY: source
<223> OTHER INFORMATION: /note="Description of Unknown: Target
      polynucleotide"

<400> SEQUENCE: 37
cgtaagatta caatggcagg ctccagtagg ttctaagtgc catgatacaa gcttcccaat    60
tactaagtat gctgagaaga acgataaaac ttgggcaa                            98

<210> SEQ ID NO 38
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 38
cacgacctcg ctgacc                                                    16

<210> SEQ ID NO 39
<211> LENGTH: 16
<212> TYPE: DNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"

<400> SEQUENCE: 39
cacgacctcg ctgacc                                                      16

<210> SEQ ID NO 40
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 40
ggtcagatga aaatgatacg tg                                               22

<210> SEQ ID NO 41
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 41
ggtcagatga aaatgatacg tg                                               22

<210> SEQ ID NO 42
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 42
ggtcagatga aaatgatacg tg                                               22

<210> SEQ ID NO 43
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 43
ggtcagatga aaatgatacg tg                                               22

<210> SEQ ID NO 44
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 44
cctcgtctga tcgtgactcc at                                               22

<210> SEQ ID NO 45
```

```
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 45
cctcgtctga tcgtgactcc at                                              22

<210> SEQ ID NO 46
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 46
cctcgtctga tcgtgactcc at                                              22

<210> SEQ ID NO 47
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 47
cctcgtctga tcgtgactcc at                                              22

<210> SEQ ID NO 48
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 48
ggagcagact agcactgagg ta                                              22

<210> SEQ ID NO 49
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 49
ggagcagact agcactgagg ta                                              22

<210> SEQ ID NO 50
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 50
```
tgtcatcttc tgtcccttcc cagaaa                                          26

<210> SEQ ID NO 51
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 51
actgtcccag aatgcaagaa gcccagacg                                       29

<210> SEQ ID NO 52
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 52
ccgtagctgc cctgg                                                      15

<210> SEQ ID NO 53
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 53
gcacagttac agtattccag cagactca                                        28

<210> SEQ ID NO 54
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 54
tcagtggtgg cagtggtagt ggtggc                                          26

<210> SEQ ID NO 55
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 55
tcagtggtgg cagtggtaga                                                 20

<210> SEQ ID NO 56
<211> LENGTH: 22
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 56
ggtcagatga aaatgatacg tg                                          22

<210> SEQ ID NO 57
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 57
ccatgataca agcttcc                                                17

<210> SEQ ID NO 58
<211> LENGTH: 41
<212> TYPE: DNA
<213> ORGANISM: Unknown
<220> FEATURE:
<221> NAME/KEY: source
<223> OTHER INFORMATION: /note="Description of Unknown: Target
      polynucleotide"

<400> SEQUENCE: 58
acttagtaat tgggaagctt gtatcatggc acttagaacc t                     41

<210> SEQ ID NO 59
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 59
cgcggcgtca ggcatatagg ataccgggac agacgccgcg                       40

<210> SEQ ID NO 60
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 60
ggtcagatga aaatgatacg tg                                          22

<210> SEQ ID NO 61
<211> LENGTH: 549
<212> TYPE: DNA
<213> ORGANISM: Unknown
<220> FEATURE:
<221> NAME/KEY: source
<223> OTHER INFORMATION: /note="Description of Unknown: Target
      polynucleotide"

<400> SEQUENCE: 61
gcccggagcg aggagagtag cactcttgtg cgggatattg atttcacgga ggatggtggt   60
caagggaccc ctatctgagg ggggtcatcc atggggacga aagggatttt gactgtaatg  120
```

```
tgctatgtac ggtaaatggc tttatgtact atgtactgtt aagggtgggt aggtttgttg      180
gtatcctagt gggtgagggg tggctttgga gttgcagttg atgtgtgata gttgagggtt      240
gattgctgta cttgcttgta agcatgggga ggggttttg atgtggattg ggttttatg        300 tactacaggt ggtcaagtat ttatggtacc gtacaatatt catggtggct ggcagtaatg      360
tacgaaatac atagcggttg ttgatgggtg agtcaatact tgggtggtac ccaaatctgc      420
ttccccatga aagaacagag aatagtttaa attagaatct tagctttggg tgctaatggt      480
ggagttaaag acttttctc tgatttgtcc ttggaaaaag gttttcatct ccggtttaca       540
agactggtg                                                              549
```

<210> SEQ ID NO 62
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 62

```
gcccggagcg aggagagtag cactcttg                                          28
```

<210> SEQ ID NO 63
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 63

```
caccagtctt gtaaaccgga gatgaa                                            26
```

<210> SEQ ID NO 64
<211> LENGTH: 525
<212> TYPE: DNA
<213> ORGANISM: Unknown
<220> FEATURE:
<221> NAME/KEY: source
<223> OTHER INFORMATION: /note="Description of Unknown: Target polynucleotide"

<400> SEQUENCE: 64

```
acaggtctat caccctatta accactcacg ggagctctcc atgcatttgg tattttcgtc       60 tgggggggtat gcacgcgata gcattgcgag acgctggagc cggagcaccc tatgtcgcag     120
tatctgtctt tgattcctgc ctcatcctat tatttatcgc acctacgttc aatattacag      180
gcgaacatac ttactaaagt gtgttaatta attaatgctt gtaggacata ataataacaa      240
ttgaatgtct gcacagccac tttccacaca gacatcataa caaaaatttt ccaccaaacc      300 cccctcccc cgcttctggc cacagcactt aaacacatct ctgccaaacc ccaaaaacaa       360
agaaccctaa caccagccta accagatttc aaatttatc ttttggcggt atgcactttt       420
aacagtcacc cccaactaa cacattattt tcccctccca ctcccatact actaatctca       480
tcaatacaac cccgcccat cctacccagc acacacacac cgctg                       525
```

<210> SEQ ID NO 65
<211> LENGTH: 26
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 65
agcggtgtgt gtgtgctggg taggat                                          26

<210> SEQ ID NO 66
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 66
acaggtctat caccctatta accactca                                        28

<210> SEQ ID NO 67
<211> LENGTH: 634
<212> TYPE: DNA
<213> ORGANISM: Unknown
<220> FEATURE:
<221> NAME/KEY: source
<223> OTHER INFORMATION: /note="Description of Unknown: Target
      polynucleotide"

<400> SEQUENCE: 67
aggttgcggt ctgttagtag tatagtgatg ccagcagcta ggactgggag agataggaga      60
agtaggactg ctgtgattag gacggatcag acgaagaggg gcgtttggta ttgggttatg     120 gcaggggtt ttatattgat aattgttgtg atgaaattga tggcccctaa gatagaggag     180
acacctgcta ggtgtaagga gaagatggtt aggtctacgg aggctccagg gtgggagtag     240
ttccctgcta agggagggta gactgttcaa cctgttcctg ctccggcctc cactatagca     300
gatgcgagca ggagtaggag agagggaggt aagagtcaga agcttatgtt gtttatgcgg     360
ggaaacgcca tatcgggggc accgattatt aggggaacta gtcagttgcc aaagcctccg     420
attatgatgg gtattactat gaagaagatt attacaaatg catgggctgt gacgataacg     480
ttgtagatgt ggtcgttacc tagaaggttg cctggctggc ccagctcggc tcgaataagg     540
aggcttagag ctgtgcctag gactccagct catgcgccga ataataggta tagtgttcca     600
atgtctttgt ggtttgtaga gaatagtcaa cggt                                 634

<210> SEQ ID NO 68
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 68
aggttgcggt ctgttagtag tatagtgatg ccagca                               36

<210> SEQ ID NO 69
<211> LENGTH: 27
<212> TYPE: DNA
<213> ORGANISM: Artificial Sequence
<220> FEATURE:
<221> NAME/KEY: source
```

```
<223> OTHER INFORMATION: /note="Description of Artificial Sequence:
      Synthetic primer"

<400> SEQUENCE: 69
accgttgact attctctaca aaccaca                                          27

<210> SEQ ID NO 70
<211> LENGTH: 731
<212> TYPE: DNA
<213> ORGANISM: Unknown
<220> FEATURE:
<221> NAME/KEY: source
<223> OTHER INFORMATION: /note="Description of Unknown: Target
      polynucleotide"

<400> SEQUENCE: 70
atggagggtt cttctactat taggactttt cgcttcgaag cgaaggcttc tcaaatcatg      60
aaaattatta atattactgc tgttagagaa atgaatgagc ctacagatga taggatgttt    120
catgtggtgt atgcatcggg gtagtccgag taacgtcggg gcattccgga taggccgaga    180
aagtgttgtg ggaagaaagt tagatttacg ccgatgaata tgatagtgaa atggattttg    240
gcgtaggttt ggtctagggt gtagcctgag aataggggaa atcagtgaat gaagcctcct    300
atgatggcaa atacagctcc tattgatagg acatagtgga agtgggctac aacgtagtac    360
gtgtcgtgta gtacgatgtc tagtgatgag tttgctaata caatgccagt caggccacct    420
acggtgaaaa gaaagatgaa tcctagggct cagagcactg cagcagatca tttcatattg    480
cttccgtgga gtgtggcgag tcagctaaat actttgacgc cggtggggat agcgatgatt    540
atggtagcgg aggtgaaata tgctcgtgtg tctacgtcta ttcctactgt aaatatatgg    600
tgtgctcaca cgataaaccc taggaagcca attgatatca tagctcagac catacctatg    660
tatccaaatg gttcttttt tccggagtag taagttacaa tatgggagat tattccgaag    720
cctggtagga t                                                         731

<210> SEQ ID NO 71
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 71
atggagggtt cttctactat taggactttt cgct                                 34

<210> SEQ ID NO 72
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 72
atcctaccag gcttcggaat aatctc                                          26

<210> SEQ ID NO 73
<211> LENGTH: 586
<212> TYPE: DNA
<213> ORGANISM: Unknown
<220> FEATURE:
```

```
<221> NAME/KEY: source
<223> OTHER INFORMATION: /note="Description of Unknown: Target
      polynucleotide"

<400> SEQUENCE: 73
agggtaaata cgggccctat ttcaaagatt tttaggggaa ttaattctag gacgatgggc      60
atgaaactgt ggtttgctcc acagatttca gagcattgac cgtagtatac ccccggtcgt     120
gtagcggtga aagtggtttg gtttagacgt ccgggaattg catctgtttt taagcctaat     180
gtggggacag ctcatgagtg caagacgtct tgtgatgtaa ttattatacg aatgggggct     240
tcaatcggga gtactactcg attgtcaacg tcaaggagtc gcaggtcgcc tggttctagg     300
aataatgggg gaagtatgta ggagttgaag attagtccgc cgtagtcggt gtactcgtag     360
gttcagtacc attggtggcc aattgatttg atggtaaggg agggatcgtt gacctcgtct     420
gttatgtaaa ggatgcgtag ggatgggagg gcgatgagga ctaggatgat ggcgggcagg     480
atagttcaga cggtttctat ttcctgagcg tctgagatgt tagtattagt tagttttgtt     540
gtgagtgtta ggaaaagggc atacaggact aggaagcaga taagga                   586

<210> SEQ ID NO 74
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 74
agggtaaata cgggccctat ttcaaagatt tttagggga                             39

<210> SEQ ID NO 75
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 75
tccttatctg cttcctagtc ctgtatgc                                         28

<210> SEQ ID NO 76
<211> LENGTH: 859
<212> TYPE: DNA
<213> ORGANISM: Unknown
<220> FEATURE:
<221> NAME/KEY: source
<223> OTHER INFORMATION: /note="Description of Unknown: Target
      polynucleotide"

<400> SEQUENCE: 76
cctctaaatc accacgatca aaaggaacaa gcatcaagca cgcagcaatg cagctcaaaa      60
cgcttagcct agccacaccc ccacgggaaa cagcagtgat taacctttag caataaacga     120
aagtttaact aagctatact aaccccaggg ttggtcaatt tcgtgccagc caccgcggtc     180
acacgattaa cccaagtcaa tagaagccgg cgtaaagagt gttttagatc accccctccc     240
caataaagct aaaactcacc tgagttgtaa aaaactccag ttgacacaaa atagactacg     300
aaagtggctt taacatatct gaacacacaa tagctaagac ccaaactggg attagatacc     360
ccactatgct tagccctaaa cctcaacagt taaatcaaca aaactgctcg ccagaacact     420
```

```
acgagccaca gcttaaaact caaaggacct ggcggtgctt catatccctc tagaggagcc      480
tgttctgtaa tcgataaacc ccgatcaacc tcaccacctc ttgctcagcc tatataccgc      540
catcttcagc aaaccctgat gaaggctaca agtaagcgc aagtacccac gtaaagacgt       600
taggtcaagg tgtagcccat gaggtggcaa gaaatgggct acattttcta ccccagaaaa     660
ctacgatagc ccttatgaaa cttaagggtc gaaggtggat ttagcagtaa actaagagta     720
gagtgcttag ttgaacaggg ccctgaagcg cgtacacacc gcccgtcacc ctcctcaagt     780
atacttcaaa ggacatttaa ctaaaacccc tacgcattta tatagaggag acaagtcgta    840
acatggtaag tgtactgga                                                  859
```

<210> SEQ ID NO 77
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 77

```
tccagtacac ttaccatgtt acgacttgtc tcctcta                               37
```

<210> SEQ ID NO 78
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 78

```
cctctaaatc accacgatca aaaggaac                                         28
```

<210> SEQ ID NO 79
<211> LENGTH: 447
<212> TYPE: DNA
<213> ORGANISM: Unknown
<220> FEATURE:
<221> NAME/KEY: source
<223> OTHER INFORMATION: /note="Description of Unknown: Target
      polynucleotide"

<400> SEQUENCE: 79

```
tgtgagggtg ggactgtcta ctgagtagcc tcctcagatt cattgaacta ggtctgtccc      60
aatgtatggg atggcggata gtaagtttgt aattactgtg gcccctcaga atgatatttg    120
gcctcacggg aggacatagc ctatgaaggc tgttgctata gttgcaagca ggaggataat    180
gccgatgttt caggtttctg agtagagaaa tgatccgtaa tataggcctc gcccgatgtg    240
taggaagagg cagataaaga atattgaggc gccattggcg tgaaggtagc ggatgattca    300
gccataattt acgtctcgag tgatgtgggc gattgatgaa aaggcggttg aggcgtctgg    360
tgagtagtgc atggctagga atagtcctgt ggtgatttgg aggatcaggc aggcgccaag    420
gagtgagccg aagtttcatc atgcgga                                         447
```

<210> SEQ ID NO 80
<211> LENGTH: 30
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic primer"

<400> SEQUENCE: 80
tgtgagggtg ggactgtcta ctgagtagcc                                          30

<210> SEQ ID NO 81
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 81
tccgcatgat gaaacttcgg ctc                                                 23

<210> SEQ ID NO 82
<211> LENGTH: 434
<212> TYPE: DNA
<213> ORGANISM: Unknown
<220> FEATURE:
<221> NAME/KEY: source
<223> OTHER INFORMATION: /note="Description of Unknown: Target
      polynucleotide"

<400> SEQUENCE: 82
actccacctc ctattcttgc acgaaacggg atcaaacaac ccctaggaa tcacctccca          60 ttccgataaa atcaccttcc acccttacta cacaatcaaa gacgccctcg gcttacttct       120
cttccttctc tccttaatga cattaacact attctcacca gacctcctag gcgacccaga       180
caattatacc ctagccaacc ccttaaacac ccctccccac atcaagcccg aatgatattt       240
cctattcgcc tacacaattc tccgatccgt ccctaacaaa ctaggaggcg tccttgccct       300
attactatcc atcctcatcc tagcaataat ccccatcctc catatatcca aacaacaaag       360
cataatattt cgcccactaa gccaatcact ttattgactc ctagccgcag acctcctcat       420
tctaacctga atcg                                                         434

<210> SEQ ID NO 83
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 83
cgattcaggt tagaatgagg aggtctgcgg ctag                                    34

<210> SEQ ID NO 84
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 84
actccacctc ctattcttgc acga                                               24
```

```
<210> SEQ ID NO 85
<211> LENGTH: 638
<212> TYPE: DNA
<213> ORGANISM: Unknown
<220> FEATURE:
<221> NAME/KEY: source
<223> OTHER INFORMATION: /note="Description of Unknown: Target
      polynucleotide"

<400> SEQUENCE: 85
cataagaaca gggaggttag aagtagggtc ttggtgacaa aatatgttgt gtagagttca      60
ggggagagtg cgtcatatgt tgttcctagg aagattgtag tggtgagggt gtttattata     120
ataatgtttg tgtattcggc tatgaagaat agggcgaagg ggcctgcggc gtattcgatg     180
ttgaagcctg agactagttc ggactcccct tcggcaaggt cgaagggggt tcggttggtc     240
tctgctagtg tggagataaa tcatattatg gccaagggtc atgatggcag gagtaatcag     300
aggtgttctt gtgttgtgat aagggtggag aggttaaagg agccacttat tagtaatgtt     360
gatagtagaa tgatggctag ggtgacttca tatgagattg tttgggctac tgctcgcagt     420
gcgccgatca gggcgtagtt tgagtttgat gctcaccctg atcagaggat tgagtaaacg     480
gctaggctag aggtggctag aataaatagg aggcctaggt tgaggttgac caggggggttg    540 ggtatgggga gggggggttca tagtagaaga gcgatggtga gagctaaggt cggggcggtg    600
atgtagaggg tgatggtaga tgtggcgggt tttagggg                             638

<210> SEQ ID NO 86
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 86
cataagaaca gggaggttag aagtagggtc ttggt                                 35

<210> SEQ ID NO 87
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 87
cccctaaaac ccgccacat                                                   19

<210> SEQ ID NO 88
<211> LENGTH: 870
<212> TYPE: DNA
<213> ORGANISM: Unknown
<220> FEATURE:
<221> NAME/KEY: source
<223> OTHER INFORMATION: /note="Description of Unknown: Target
      polynucleotide"

<400> SEQUENCE: 88
agtgtgattg aggtggagta gattaggcgt aggtagaagt agaggttaag gagggtgatg      60
gtggctatga tggtggggat gatgaggcta ttgttttttg tgaattcttc gataatggcc     120
catttgggca aaaagccggt tagcggggc aggcctccta gggagaggag ggtggatgga      180
```

```
attaagggtg ttagtcatgt tagcttgttt caggtgcgag atagtagtag ggtcgtggtg    240
ctggagttta agttgagtag taggaatgcg gtagtagtta ggataatata aatagttaaa    300
ttaagaatgg ttatgttagg gttgtacggt agaactgcta ttattcatcc tatgtgggta    360
attgaggagt atgctaagat tttgcgtagc tgggtttggt ttaatccacc tcaactgcct    420
gctatgatgg ataagattga gagagtgagg agaaggctta cgtttagtga gggagagatt    480
tggtatatga ttgagatggg ggctagtttt tgtcatgtga aagaagcag gccggatgtc    540 agaggggtgc cttgggtaac ctctgggact cagaagtgaa aggggggctat tcctagtttt   600 attgctatag ctattatgat tattaatgat gagtattgat tggtagtatt ggttatggtt    660
cattgtccgg agagtatatt gttgaagagg atagctatta aaggattat ggatgcggtt     720 gcttgcgtga ggaaatactt gatggcagct tctgtggaac gagggtttat ttttttggtt   780
agaactggaa taaaagctag catgtttatt tctaggccta ctcaggtaaa aaatcagtgc    840
gagcttagcg ctgtgatgag tgtgcctgca                                    870
```

```
<210> SEQ ID NO 89
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 89
agtgtgattg aggtggagta gattaggcgt aggtagaagt                          40

<210> SEQ ID NO 90
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 90
tgcaggcaca ctcatcacag cgctaagct                                     29

<210> SEQ ID NO 91
<211> LENGTH: 497
<212> TYPE: DNA
<213> ORGANISM: Unknown
<220> FEATURE:
<221> NAME/KEY: source
<223> OTHER INFORMATION: /note="Description of Unknown: Target
      polynucleotide"

<400> SEQUENCE: 91
aacacaacca cccacagcct aattattagc atcatccctc tactattttt taaccaaatc     60
aacaacaacc tatttagctg ttccccaacc ttttcctccg acccctaac aaccccctc     120 ctaatactaa ctacctgact cctacccctc acaatcatgg caagccaacg ccacttatcc    180
agtgaaccac tatcacgaaa aaaactctac ctctctatac taatctccct acaaatctcc    240
ttaattataa cattcacagc cacagaacta atcatatttt atatcttctt cgaaaccaca    300
cttatcccca ccttggctat catcacccga tgaggcaacc agccagaacg cctgaacgca    360
ggcacatact tcctattcta cacccctagta ggctcccttc ccctactcat cgcactaatt    420
tacactcaca acaccctagg ctcactaaac attctactac tcactctcac tgcccaagaa    480
```
ctatcaaact cctgagc        497

<210> SEQ ID NO 92
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 92
gctcaggagt tgatagttc ttgggcagtg agag        34

<210> SEQ ID NO 93
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 93
aacacaacca cccacagcct aattattag        29

<210> SEQ ID NO 94
<211> LENGTH: 493
<212> TYPE: DNA
<213> ORGANISM: Unknown
<220> FEATURE:
<221> NAME/KEY: source
<223> OTHER INFORMATION: /note="Description of Unknown: Target
      polynucleotide"

<400> SEQUENCE: 94
gtggtgggtg agtgagcccc attgtgttgt ggtaaatatg tagagggagt atagggctgt        60
gactagtatg ttgagtcctg taagtaggag agtgatattt gatcaggaga acgtggttac       120
tagcacagag agttctccca gtaggttaat agtgggggt aaggcgaggt tagcgaggct       180
tgctagaagt catcaaaaag ctattagtgg gagtagagtt tgaagtcctt gagagaggat       240
tatgatgcga ctgtgagtgc gttcgtagtt tgagtttgct aggcagaata gtaatgagga       300
tgtaagcccg tgggcgatta tgagaatgac tgcgccggtg aagcttcagg gggtttggat       360
gagaatggct gttactacga gggctatgtg gctgattgaa gagtatgcaa tgagcgattt       420
taggtctgtt tgtcgtaggc agatggagct tgttataatt atgcctcata gggatagtac       480
aaggaagggg tag       493

<210> SEQ ID NO 95
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 95
gtggtgggtg agtgagcccc attgtgt        27

<210> SEQ ID NO 96
<211> LENGTH: 29
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 96
ctaccccttc cttgtactat ccctatgag                                         29

<210> SEQ ID NO 97
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 97
taaagcccgg agcgaggaga gtagcactct tg                                     32

<210> SEQ ID NO 98
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 98
aaagcggtgt gtgtgtgctg ggtaggat                                          28

<210> SEQ ID NO 99
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 99
aaaggttgcg gtctgttagt agtatagtga tgccagca                               38

<210> SEQ ID NO 100
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 100
aaatggaggg ttcttctact attaggactt ttcgct                                 36

<210> SEQ ID NO 101
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 101
taagggtaaa tacgggccct atttcaaaga tttttagggg a                           41
```

```
<210> SEQ ID NO 102
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 102
aatccagtac acttaccatg ttacgacttg tctcctcta                                39

<210> SEQ ID NO 103
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 103
aatgtgaggg tgggactgtc tactgagtag cc                                       32

<210> SEQ ID NO 104
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 104
aacgattcag gttagaatga ggaggtctgc ggctag                                   36

<210> SEQ ID NO 105
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 105
aacataagaa cagggaggtt agaagtaggg tcttggt                                  37

<210> SEQ ID NO 106
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 106
aaagtgtgat tgaggtggag tagattaggc gtaggtagaa gt                            42

<210> SEQ ID NO 107
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
```

```
            Synthetic primer"

<400> SEQUENCE: 107
aagctcagga gtttgatagt tcttgggcag tgagag                    36

<210> SEQ ID NO 108
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 108
tagtggtggg tgagtgagcc ccattgtgt                            29

<210> SEQ ID NO 109
<211> LENGTH: 62
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 109
ttgcacgaga gccagctcgt caggtagtca ccagtacagt ccgcttgtgt caagacagca   60
cg                                                                 62

<210> SEQ ID NO 110
<211> LENGTH: 75
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 110
cagcagcaga cagtgcactc gtcactcact aaccgctatt cgagttcgcg tgctgtcttg   60
acacaagcgg actgt                                                   75

<210> SEQ ID NO 111
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 111
ttgcacgaga gccagctcgt caggtagtca ccagt                     35

<210> SEQ ID NO 112
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 112
cagcagcaga cagtgcactc gtcac                                25
```

```
<210> SEQ ID NO 113
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 113
ggagcagact agcactgagg ta                                              22

<210> SEQ ID NO 114
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 114
ctccagcccg gcacgctcac gtgacagacc g                                    31

<210> SEQ ID NO 115
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 115
ccggtggtcg ccgcgatcaa ggag                                            24

<210> SEQ ID NO 116
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 116
gcgggttgtt ctggtccatg a                                               21

<210> SEQ ID NO 117
<211> LENGTH: 150
<212> TYPE: DNA
<213> ORGANISM: Unknown
<220> FEATURE:
<221> NAME/KEY: source
<223> OTHER INFORMATION: /note="Description of Unknown: Target
      polynucleotide"

<400> SEQUENCE: 117
ccggtggtcg ccgcgatcaa ggagttcttc ggcaccagcc agctgagcca attcatggac     60
cagaacaacc cgctgtcggg gttgacccac aagcgccgac tgtcggcgct ggggcccggc    120
ggtctgtcac gtgagcgtgc cgggctggag                                    150

<210> SEQ ID NO 118
<211> LENGTH: 29
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 118
tatcgtcaag gcactcttgc ctacgcctt                                        29

<210> SEQ ID NO 119
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 119
gtactggtgg agtatttgat agtgtattaa cc                                    32

<210> SEQ ID NO 120
<211> LENGTH: 158
<212> TYPE: DNA
<213> ORGANISM: Unknown
<220> FEATURE:
<221> NAME/KEY: source
<223> OTHER INFORMATION: /note="Description of Unknown: Target
      polynucleotide"

<400> SEQUENCE: 120
gtactggtgg agtatttgat agtgtattaa ccttatgtgt gacatgttct aatatagtca      60
cattttcatt attttttatta taaggcctgc tgaaaatgac tgaatataaa cttgtggtag    120
ttggagctga tggcgtaggc aagagtgcct tgacgata                             158

<210> SEQ ID NO 121
<211> LENGTH: 158
<212> TYPE: DNA
<213> ORGANISM: Unknown
<220> FEATURE:
<221> NAME/KEY: source
<223> OTHER INFORMATION: /note="Description of Unknown: Target
      polynucleotide"

<400> SEQUENCE: 121
gtactggtgg agtatttgat agtgtattaa ccttatgtgt gacatgttct aatatagtca      60
cattttcatt attttttatta taaggcctgc tgaaaatgac tgaatataaa cttgtggtag    120
ttggagctgg tggcgtaggc aagagtgcct tgacgata                             158

<210> SEQ ID NO 122
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 122
gcacagttac agtattccag cagactca                                         28

<210> SEQ ID NO 123
<211> LENGTH: 26
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic primer"

<400> SEQUENCE: 123
tcagtggtgg cagtggtagt ggtggc                                              26

<210> SEQ ID NO 124
<211> LENGTH: 76
<212> TYPE: DNA
<213> ORGANISM: Unknown
<220> FEATURE:
<221> NAME/KEY: source
<223> OTHER INFORMATION: /note="Description of Unknown: Target
      polynucleotide"

<400> SEQUENCE: 124
gcacagttac agtattccag cagactcaaa tacaagaacc tactgctaat gccaccacta         60
ccactgccac cactga                                                         76

<210> SEQ ID NO 125
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 125
tcagtggtgg cagtggtaga                                                     20

<210> SEQ ID NO 126
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 126
ctttggcacc agaggtgagc                                                     20

<210> SEQ ID NO 127
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 127
ggtgcgtggg tcccagtctg cagttaag                                            28

<210> SEQ ID NO 128
<211> LENGTH: 65
<212> TYPE: DNA
<213> ORGANISM: Unknown
<220> FEATURE:
<221> NAME/KEY: source
<223> OTHER INFORMATION: /note="Description of Unknown: Target
      polynucleotide"

<400> SEQUENCE: 128
```

```
ggtgcgtggg tcccagtctg cagttaaggg ggcaggagtg gcgctgctca cctctggtgc    60
caaag                                                                65
```

<210> SEQ ID NO 129
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 129

```
gcaggagtgg cgct                                                      14
```

<210> SEQ ID NO 130
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 130

```
aatgtgaggg tgggactgtc tactgagtag cc                                  32
```

<210> SEQ ID NO 131
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 131

```
tacctcagtg ctagtctgct cc                                             22
```

<210> SEQ ID NO 132
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 132

```
tccagtacac ttaccatgtt acgacttgtc tcctcta                             37
```

<210> SEQ ID NO 133
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 133

```
agttcaccct ctaaatcacc acgat                                          25
```

<210> SEQ ID NO 134
<211> LENGTH: 25
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 134
atcgttgtgg tatagagggt gaact                                          25

<210> SEQ ID NO 135
<211> LENGTH: 865
<212> TYPE: DNA
<213> ORGANISM: Unknown
<220> FEATURE:
<221> NAME/KEY: source
<223> OTHER INFORMATION: /note="Description of Unknown: Target
      polynucleotide"

<400> SEQUENCE: 135
agttcaccct ctaaatcacc acgatcaaaa ggaacaagca tcaagcacgc agcaatgcag     60
ctcaaaacgc ttagcctagc cacaccccca cgggaaacag cagtgattaa cctttagcaa    120
taaacgaaag tttaactaag ctatactaac cccaggggttg gtcaatttcg tgccagccac   180
cgcggtcaca cgattaaccc aagtcaatag aagccggcgt aaagagtgtt ttagatcacc    240
ccctccccaa taaagctaaa actcacctga gttgtaaaaa actccagttg acacaaaata    300
gactacgaaa gtggctttaa catatctgaa cacacaatag ctaagaccca aactgggatt    360 agataccccca ctatgcttag ccctaaacct caacagttaa atcaacaaaa ctgctcgcca   420
gaacactacg agccacagct taaaactcaa aggacctggc ggtgcttcat atccctctag    480
aggagcctgt tctgtaatcg ataaaccccg atcaacctca ccacctcttg ctcagcctat    540
ataccgccat cttcagcaaa ccctgatgaa ggctacaaag taagcgcaag tacccacgta    600
aagacgttag gtcaaggtgt agcccatgag gtggcaagaa atgggctaca ttttctaccc    660
cagaaaacta cgatagccct tatgaaactt aagggtcgaa ggtggattta gcagtaaact    720
aagagtagag tgcttagttg aacagggccc tgaagcgcgt acacaccgcc cgtcaccctc    780
ctcaagtata cttcaaagga catttaacta aaaccccctac gcatttatat agaggagaca    840
agtcgtaaca tggtaagtgt actgg                                          865

<210> SEQ ID NO 136
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 136
gacttgcgcg ttacgacagg ccaatc                                         26

<210> SEQ ID NO 137
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 137
tgaatgcggc taatcccaac                                                20
```

-continued

<210> SEQ ID NO 138
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 138
aaccacctgc ccctt                                                         15

<210> SEQ ID NO 139
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 139
gcgcctcacg tatcattttc atctgaccag gcgc                                    34

<210> SEQ ID NO 140
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 140
gcgcctcacg tatcattttc atctgaccag gcgc                                    34

<210> SEQ ID NO 141
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 141
gcgcctcacg tatcattttc atctgaccag gcgc                                    34

<210> SEQ ID NO 142
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 142
gcgcctcacg tatcattttc atctgaccag gcgc                                    34

<210> SEQ ID NO 143
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 143
gcgcctcacg tatcattttc atctgaccag gcgc                          34

<210> SEQ ID NO 144
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 144
gcgcctcacg tatcattttc atctgaccag gcgc                          34

<210> SEQ ID NO 145
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 145
gcgcctcacg tatcattttc atctgaccag gcgc                          34

<210> SEQ ID NO 146
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 146
gcgcctcacg tatcattttc atctgaccag gcgc                          34

<210> SEQ ID NO 147
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 147
gcactcttgc ctacgcc                                             17

<210> SEQ ID NO 148
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 148
ctggtggagt atttgatagt g                                        21

<210> SEQ ID NO 149
<211> LENGTH: 18
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 149
gcctacgcca ccagctcc                                                  18

<210> SEQ ID NO 150
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 150
caagaacatg tcacacataa tg                                             22

<210> SEQ ID NO 151
<211> LENGTH: 145
<212> TYPE: DNA
<213> ORGANISM: Unknown
<220> FEATURE:
<221> NAME/KEY: source
<223> OTHER INFORMATION: /note="Description of Unknown: Target
      polynucleotide"

<400> SEQUENCE: 151
ctggtggagt atttgatagt gtattaacct tatgtgtgac atgttctaat atagtcacat    60
tttcattatt tttattataa ggcctgctga aaatgactga atataaactt gtggtagttg   120
gagctggtgg cgtaggcaag agtgc                                         145

<210> SEQ ID NO 152
<211> LENGTH: 145
<212> TYPE: DNA
<213> ORGANISM: Unknown
<220> FEATURE:
<221> NAME/KEY: source
<223> OTHER INFORMATION: /note="Description of Unknown: Target
      polynucleotide"

<400> SEQUENCE: 152
ctggtggagt atttgatagt gtattaacct tatgtgtcac atgttctaat atagtcacat    60
tttcattatt tttattataa ggcctgctga aaatgactga atataaactt gtggtagttg   120
gagctgatgg cgtaggcaag agtgc                                         145

<210> SEQ ID NO 153
<211> LENGTH: 8
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 153 cgccgcgc                                                              8

<210> SEQ ID NO 154
<211> LENGTH: 22
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 154
tgagagatga aaatcatcga gt                                             22

<210> SEQ ID NO 155
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 155
actcgatcat ttttcactct ca                                             22

<210> SEQ ID NO 156
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 156
tacctcagtg ttagtctggt cc                                             22

<210> SEQ ID NO 157
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 157
tacctcagtg ttagtctggt cc                                             22

<210> SEQ ID NO 158
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 158
cggaggggtc agatgaaaat gatacgtgcc tccg                                34

<210> SEQ ID NO 159
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 159
cggaggggtc agatgaaaat gatacgtgcc tccg                                34
```

<210> SEQ ID NO 160
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 160
cggaggggtc agatgaaaat gatacgtgcc tccg                              34

<210> SEQ ID NO 161
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 161
cggaggggtc agatgaaaat gatacgtgcc tccg                              34

<210> SEQ ID NO 162
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 162
cggaggggtc agatgaaaat gatacgtgcc tccg                              34

<210> SEQ ID NO 163
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 163
cggaggggtc agatgaaaat gatacgtgcc tccg                              34

<210> SEQ ID NO 164
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 164
cggaggggtc agatgaaaat gatacgtgcc tccg                              34

<210> SEQ ID NO 165
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

```
<400> SEQUENCE: 165
cggaggggtc agatgaaaat gatacgtgcc tccg                              34
```

REAGENTS AND METHODS OF PCR

CROSS-REFERENCE FOR RELATED PATENT APPLICATIONS

This application is a continuation of U.S. patent application Ser. No. 13/256,038, filed Mar. 11, 2010, which is a 371 US National Entry of International Patent Application Serial Number PCT/US2010/027011, filed Mar. 11, 2010, which claims benefit to U.S. provisional patent application No. 61/202,565, filed Mar. 12, 2009 to Zhang, which is hereby incorporated by reference in its entirety.

SEQUENCE LISTING

The instant application contains a Sequence Listing which has been submitted in ASCII format via EFS-Web and is hereby incorporated by reference in its entirety.

FIELD

Nucleic acid amplification reactions and assays including both real-time and end point homogeneous polymerase chain reaction (PCR) monoplex and multiplex amplification assays are provided.

BACKGROUND

Amplification and amplification assays using DNA primers and a DNA polymerase are well-known for amplifying and for detecting nucleic acid target sequences. Methods for exponential amplification include the polymerase chain reaction (PCR), strand displacement amplification (SDA), nucleic acid sequence based amplification (NASBA), transcription-mediated amplification (TMA), and rolling circle amplification (RCA). Certain of these primer-dependent amplification methods, such as PCR, include thermal cycling, while others, such as NASBA, are isothermal. Among numerous DNA polymerases commonly used are *Thermus aquaticus* DNA polymerase (Taq polymerase) and reverse transcriptase. The design of linear DNA oligonucleotide amplification primers is generally accomplished with the aid of a computer program designed for that purpose. Among the available programs that can be utilized are PRIDE (Haas et al., Nucl. Acids Res. 26:3006-3012 1998); OLIGO (Rychlik et al., Nucl. Acids Res 17(21):8543-51 1989); OSP (Hilber et al., OSP: a computer program for choosing PCR and DNA sequencing primers. PCR Methods Appl. 1(2):124-128 1991); Primo (Li et al., Genomics 40(3): 476-85 1997); and Primer Master (Proutski et al., Comput Appl Biosci 12(3):253-5 1996).

Nucleic acid amplification employing PCR is well known, as are assays that include PCR amplification. See U.S. Pat. Nos. 4,683,202, 4,683,195 and 4,965,188 and, generally, PCR PROTOCOLS, a guide to Methods and Applications, Innis et al. eds., Academic Press (San Diego, Calif. (USA) 1990). Homogeneous PCR assays that do not require washing to remove unbound detector reagents or probes and thus can be performed without opening amplification reaction vessels are also well known. Homogeneous PCR assays include both end-point assays, in which amplified product is detected at the end of the amplification reaction, and real-time assays, in which amplified product is detected during some or all of the thermal cycles as the reaction proceeds. See U.S. Pat. Nos. 5,994,056, 5,487,972, 5,925,517 and 6,150,097.

PCR amplification reactions, like other amplification methods referred to above, are generally designed to be symmetric, that is, to make double-stranded amplicons by utilizing a forward primer and a reverse primer that are "matched"; that is, they have melting temperatures that are as close as possible, and they are added to the reaction in equimolar concentrations. A technique that has found limited use for making single-stranded DNA directly in a PCR reaction is "asymmetric PCR." Gyllensten and Erlich, "Generation of Single-Stranded DNA by the Polymerase Chain Reaction and Its Application to Direct Sequencing of the HLA-DQA Locus," Proc. Natl. Acad. Sci. (USA) 85: 7652-7656 (1988); and U.S. Pat. No. 5,066,584. Asymmetric PCR differs from symmetric PCR in that one of the primers is added in limiting amount, typically 1-20 percent of the concentration of the other primer.

A more recently developed non-symmetric PCR amplification method is known as "Linear-After-The-Exponential" PCR or, for short, "LATE-PCR." See Sanchez et al. (2004) PNAS 101: 1933-1938, Pierce et al. (2005) PNAS 102: 8609-8614, and published international patent application WO 03/054233 (3 Jul. 2003), which is incorporated herein by reference in its entirety. LATE-PCR takes into account the actual, concentration-adjusted melting temperatures of PCR primers at the start of amplification, referred to as $Tm_{[0]}$. $Tm_{[0]}$ can be determined empirically, as is necessary when non-natural nucleotides are used, or calculated. A variety of fluorescent probes can be used with LATE-PCR, including, among others: molecular beacons, which are single-strands capable of forming a stem-loop structure that can close when not bound to target thereby bringing near to each other a fluorophore on one end and a quencher on the other end; linear single-stranded probes having a fluorophore on one end and a quencher on the other end; FRET probe pairs, which are two labeled, single-stranded probes that hybridize adjacently on a target sequence, permitting their labels to pass energy between them by FRET; fluorophore-labeled linear probes that FRET with a DNA dye; and linear double-stranded probes in which the fluorophore is on the strand that binds to target and the quencher is on a complementary strand that binds to the probe at an equivalent Tm in the absence of a target.

An undesirable feature of symmetric PCR amplifications is that, following the exponential phase of amplification, fluorescence curves obtained by monitoring replicate amplifications in real time diverge and plateau at different levels. Scatter indicates that replicates do not have the same reaction efficiency and reduces detection accuracy. This is a problem for PCR assays generally, but is particularly undesirable in the case of end-point assays. Scatter among replicates is considerably reduced but still present in LATE-PCR assays and asymmetric PCR assays, both of which have an exponential phase and a linear phase. The scatter in the linear phase in part reflects the scatter in the plateau at the end of the exponential amplification when the limiting primer runs out.

Another significant problem with primer-dependent amplification reactions, including PCR amplifications, is mispriming, which we consider to be manifested in several distinct types: Type 1, mispriming that occurs during preparation of reaction mixtures prior to the start of amplification; Type 2, mispriming that occurs during amplification if the temperature (which in PCR amplifications means the temperature in any thermal cycle) is for any reason reduced below the melting temperature of a primer; and Type 3, mispriming that occurs in the late stages of amplification, including a PCR amplification, that is continued after a high concentration of amplicon has been made. When Type 3 mispriming occurs in LATE-PCR and asymmetric reactions, the 3' end of a single-stranded amplicon primes on another ss-DNA molecule, thereby converting ss-DNA into ds-DNA. Mispriming in a reaction can also result in scatter among replicate reactions. Mispriming includes primer-dimer formation, which can occur during any stage of amplification.

Several approaches have been used to address Type 1 mispriming One approach is to modify the polymerase chemically so that it is inactive until heated to a high temperature such as 95° C. See U.S. Pat. Nos. 5,677,152 and 5,773,258. Another approach is to bind an antibody to the polymerase to inhibit the polymerase until the reaction is heated to a high temperature such as 95° C. to irreversibly denature the antibody. See U.S. Pat. No. 5,338,671. Chemically modified and antibody-bound DNA polymerases are commonly referred to as "hot start" DNA polymerases. Yet another "hot start" approach is to include an aptamer in the reaction mixture. See Doug and Jayasena (1996), J. Mol. Biol. 264: 268-278 and U.S. Pat. No. 6,020,130. An aptamer is a single-stranded oligonucleotide approximately 30 nucleotides in length that binds to a polymerase and inhibits its ability to extend a recessed 3' end at low temperatures. Aptamers are not irreversibly denatured at 95° C., a typical highest temperature for a PCR cycle. Eppendorf-5 Prime, Inc. markets a proprietary ligand that is said to bind to Taq polymerase in a temperature-dependent manner and to inhibit its binding to double-stranded DNA at temperatures below about 50° C. Despite these many attempts, mispriming remains a problem with PCR amplifications.

Another type of mispriming during primer-dependent amplification reactions, including PCR amplifications, is known as primer-dimer formation and primer-dimer amplification. According to this phenomenon one primer hybridizes to the other primer or to another copy of itself and then undergoes extension of the 3' end to generate a small double-stranded amplicon, which can then amplify further or can multimerize and amplify further. Primer-dimer formation can occur in the absence of target.

Quantitative analysis of amplification reactions, including PCR amplifications, has been enabled by real-time detection methods. In PCR amplifications the PCR cycle at which fluorescent signal becomes visible above the threshold cycle or $C_T$ of reactions is indicative of starting target concentrations. End-point analyses are semi-quantitative at best, due in part to scatter among replicates as the reaction exits exponential amplification. Electrophoretic analysis of double-stranded amplicons is semi-quantitative, and may utilize fluorescently labeled primers. End-point analysis utilizing fluorescently labeled probes, either allele-discriminating probes or mismatch-tolerant probes, are also semi-quantitative at best. By reducing scatter and producing single-stranded product, LATE-PCR offers significant improvement in end-point analysis, but scatter among replicates is often not completely eliminated, leaving quantitative and multiplex detection less accurate and more problematic than desired.

Design and construction of multiplex PCR assays often encounters the problem of mispriming, because the use of multiple pairs of primers in a single reaction geometrically increases the number of possible unintended interactions of primers and target sequences or other DNA strands that may be present. Indeed, in symmetric multiplex PCR assays it is very difficult to design all primer pairs to have the same melting temperature, and in a asymmetric or LATE-PCR multiplex PCR assay to design all of the limiting primers to have a single melting temperature and all of the excess primers to have a single melting temperature. It therefore follows that in a multiplex PCR assay the particular annealing temperature used for one or more thermal cycles is not likely to be optimal for all pairs of primers. If the primer annealing step of a PCR cycle is set to permit hybridization of the lowest Tm primer, the reaction will have reduced stringency for primers with Higher Tm's, which increases the chance for mispriming to occur. Moreover, in LATE-PCR assays the limiting primers used (whether in a monoplex or a multiplex) typically have melting temperatures 5° C. or more above the melting temperatures of the excess primers, again making it impossible to match a single primer annealing temperature to the melting temperature of both primers.

A property of DNA polymerases in primer-dependent amplifications, including PCR amplifications, is a nominal amount of selectivity, particularly a nominal ability to discriminate between a target sequence that is perfectly complementary to a primer and a sequence that is perfectly complementary except for a mismatch at the 3' terminal nucleotide of the primer. It has been attempted to take advantage of this nominal selectivity to detect single-nucleotide mutations, or SNPs, by designing primers having their 3' terminal nucleotide complementary to the target nucleotide that is subject to mutation. The amplification assay method known as the amplification refractory mutation system (ARMS) attempts to do that (Newton et al., Nucl. Acids Res. 17, 2503-2516 (1989); Wu et al., Proc. Natl. Acad. Sci. USA 86:2757-2760 (1989)). ARMS assays are prone to generation of false-positive signals due to mispriming and primer-dimer formation. Certain mispriming events may involve a primer that hybridizes incorrectly such that there is a 3' mismatched nucleotide. Primer-dimer formation may also involve a mismatched 3' nucleotide. In the last phase of a LATE-PCR amplification mispriming of a single-stranded amplicon on another single strand in the reaction mixture may also involve a mismatched 3' nucleotide. Therefore, enhancing a polymerase's discrimination against a 3' terminal mismatch can, among other effects, reduce mispriming. Attempts have been made to improve selectivity during amplification beyond the foregoing nominal selectivity by making amplification primers themselves more selective. For example, Tyagi et al. added to the 5' end of a primer a sequence complementary to the 3' end of the primer to form a stem-loop structure wherein the loop and the 3' portion of the stem are complementary to the target strand (U.S. Pat. No. 6,277,607). This approach is not seen to reduce the difficulty, described above, of designing primers for multiples assays. Making primers more selective does not, of course, improve the selectivity of DNA polymerases.

To improve selectivity, an alternative to modifying primers is to affect the DNA polymerase itself. U.S. patent application U.S. Ser. No. 11/242,506 describes a class of reagent additives that somewhat improve product specificity and that greatly reduce or in some cases practically eliminate the effects of mispriming in PCR amplification reactions. This class of reagents is comprised of single oligonucleotides molecules that are able to fold into hairpin structures having a stem and a loop when the temperature is lowered below the melting temperature of the stem. Although the double-stranded stem closes, the nucleotides at the 3' and 5' ends tend to unwind. Therefore, these additive reagents are chemically modified at both their 3' and 5' ends to keep the ends closed. End closure in this way effectively increases the melting temperature of the stem. In the closed configuration these reagent additives interact with DNA polymerase so as to improve selectivity. In the closed configuration they also inhibit polymerase activity of DNA polymerases. While these additives out-perform existing "hot-start" methodologies in all types of PCR and can be used to prevent the accumulation of undesired products, including primer-dimers and misprimed amplicons, both at early stages of the reaction and during LATE-PCR reactions having many cycles (typically 60 cycles and more), they do have their limitations which are inherent to their being comprised of a single oligonucleotide. Specifically, the length of the stem cannot be greater than about 12 nucleotides, because, if it is, and is also chemically modified at its ends, its melting temperature becomes so high that it does not readily open when the PCR is heated to the extension temperature. Even when added at low concentration, hairpin molecules with long stems and high Tm tend to inhibit the reaction. Yet another difficulty inherent to these additives is that they are not linearly symmetric, i.e. one end of the closed hairpin is open while the other end is a loop. As described in U.S. patent application U.S. Ser. No. 11/242,506, molecules with loops comprised of 3-22 nucleotides tend to inhibit amplification more readily than molecules in which the loop is formed by use of a 3 carbon or 6 carbon linker. It would be desirable to have reagents which are structurally symmetrical end-to-end.

Kainz et al. (2000) Biotechniques 28: 278-282 reported that DNA fragments, double-stranded DNA oligonucleotides, having lengths of 16-21 nucleotides can inhibit mispriming that occurs at or just below the optimal annealing temperature of symmetric PCR reactions and thereby prevent amplification of non-specific products. The DNA oligomers are reversibly denatured during the melting step of the PCR cycling. In all cases the assays that Kainz et al. employed revealed the presence of, and inhibition of, mispriming that takes place when the temperature is descending to the optimal annealing temperature after the first melting event at 95° C. This does not address Type 1 mispriming, as Kainz et al. acknowledged, and their data reveal that double-stranded fragments that are only double-stranded when Type 1 mispriming occurs (that is, with melting temperatures >5° C. below the annealing temperature of the reaction) fail to prevent mispriming From Kainz et al. one infers that their method will likely be even more unreliable in multiplex reactions because, as explained above, the annealing temperature cannot be simultaneously be optimized for all pairs of primers. Kainz et al. also acknowledged that, although they did not observe it in their particular experiments, double-stranded DNA oligonucleotides may trigger mispriming, if they become the target for hybridization of one or more primers in the reaction.

SUMMARY

One embodiment is a reaction mixture for a primer-dependent DNA amplification reaction, preferably a PCR amplification reaction, including primer extension by a DNA polymerase for amplifying at least one DNA target sequence, said reaction mixture including at least one primer pair, a thermally stable DNA polymerase and dNTP's, the improvement comprising including in the reaction mixture prior to the start of amplification at least one double-stranded oligonucleotide additive that has terminal regions on each of its strands, that has a hybrid length of 6-50 nucleotides long, that is at least 50% double-stranded at 32° C., and that includes 1-4 modifying groups, preferably two, three or four modifying groups, each covalently attached to a different terminal region, preferably to a terminal nucleotide, said modifying groups being polycyclic moieties that do not have bulky portions that are non-planar, wherein said at least one double-stranded oligonucleotide additive is included at a concentration that is effective for at least one of the functions of suppressing mispriming, increasing polymerase selectivity against hybrids having recessed 3' terminal sequences that are not perfectly complementary, increasing polymerase selectivity against hybrids having recessed 3' terminal sequences that are AT-rich, reducing scatter among replicate reactions, inhibiting polymerase 5' exonuclease activity, and inhibiting polymerase activity; provided that, if the additive is a primer or detection probe for any target sequence, it includes at least three modifying groups.

Another embodiment is a reaction mixture as described in the preceding paragraph that includes a mixture of two such double-stranded additives.

Another embodiment is a reaction mixture as described above wherein the additive includes a first strand that is a primer or probe for said at least one target sequence and a reverse complement strand that is partially complementary to the first strand, and wherein the additive includes three of the described modifying groups.

Another embodiment is primer-dependent amplification of DNA (including cDNA) targets, preferably PCR amplification, using reaction mixtures described above and, where necessary reverse transcribing RNA to obtain the DNA target sequence to be amplified.

Another embodiment is homogeneous detection assays, both real-time and end-point assays, that include such primer-dependent amplifications plus fluorescence detection of amplification products.

Another embodiment is reagent kits containing primers for at least one DNA target sequence, dNTPs, a thermally stable DNA polymerase, and at least one modified double-stranded oligonucleotide additive as describe above.

Another embodiment is such reagent kits that also include at least on fluorescence detection reagent for detecting amplification reaction products homogeneously.

Another embodiment is modified double-stranded oligonucleotides that have terminal regions on each of their strands, that have a hybrid length of 6-50 nucleotides long, that is at least 50% double-stranded at 40° C., preferably, but at least at 32° C., and that include 2-4 modifying groups, each covalently attached to a different terminal region, preferably to a terminal nucleotide, said modifying groups being polycyclic moieties that do not have bulky portions that are non-planar, said modified oligonucleotide being capable of binding to the 5' exonuclease domains of DNA polymerases.

Another embodiment is a primer-dependent DNA amplification reaction mixture including primer extension by a DNA polymerase for amplifying at least one DNA target sequence, said reaction mixture including at least one primer pair, a DNA polymerase and dNTP's, the improvement comprising including in the reaction mixture prior to the start of amplification at least one double-stranded oligonucleotide additive that has a hybrid length of 6-50 nucleotides long, that is at least fifty percent double-stranded at 32° C., that has terminal regions on each of its strands and includes 1-4 modifying groups, each covalently attached to a different terminal region, said modifying groups being polycyclic moieties that do not have bulky portions that are non-planar, wherein said at least one double-stranded oligonucleotide additive is included at a concentration relative to the concentration of said DNA polymerase that is effective for at least one of the functions of suppressing mispriming, increasing polymerase selectivity against hybrids having recessed 3' terminal sequences that are not perfectly complementary, increasing polymerase selectivity against hybrids having recessed 3' terminal sequences that are AT-rich, reducing scatter among replicate reactions, inhibiting polymerase 5' exonuclease activity, and inhibiting polymerase activity; provided that, if the additive is a primer or detection probe for any target sequence, it includes at least three modifying groups.

Another embodiment is an amplification assay that includes amplification and fluorescence detection of single-stranded products of the reaction, double-stranded products of the reaction, or both, either in real time during amplification or end point following amplification, wherein double-stranded products of the reaction are detected with a fluorescent DNA dye, single-stranded products of the reaction are detected with at least one fluorescently labeled hybridization probe, or both.

Another embodiment is a modified double-stranded oligonucleotide that has terminal regions on each of its strands, that has a hybrid length of 6-50 nucleotides long, that is at least fifty percent double-stranded at 32° C., and that includes 2-4 modifying groups, each covalently attached to a different terminal region, said modifying groups being polycyclic moieties that do not have bulky portions that are non-planar, said modified oligonucleotide being capable of inhibiting the 5' exonuclease domains of DNA polymerases. The modified double-stranded oligonucleotide may have from one to four single-stranded overhangs, and, when not hybridized in the double-stranded oligonucleotide structure, it may comprise either one or two single strands that form a stem-loop (hairpin) structure, in which case the stem is 6 or fewer base-pairs long.

DETAILED DESCRIPTION

Figure 1:
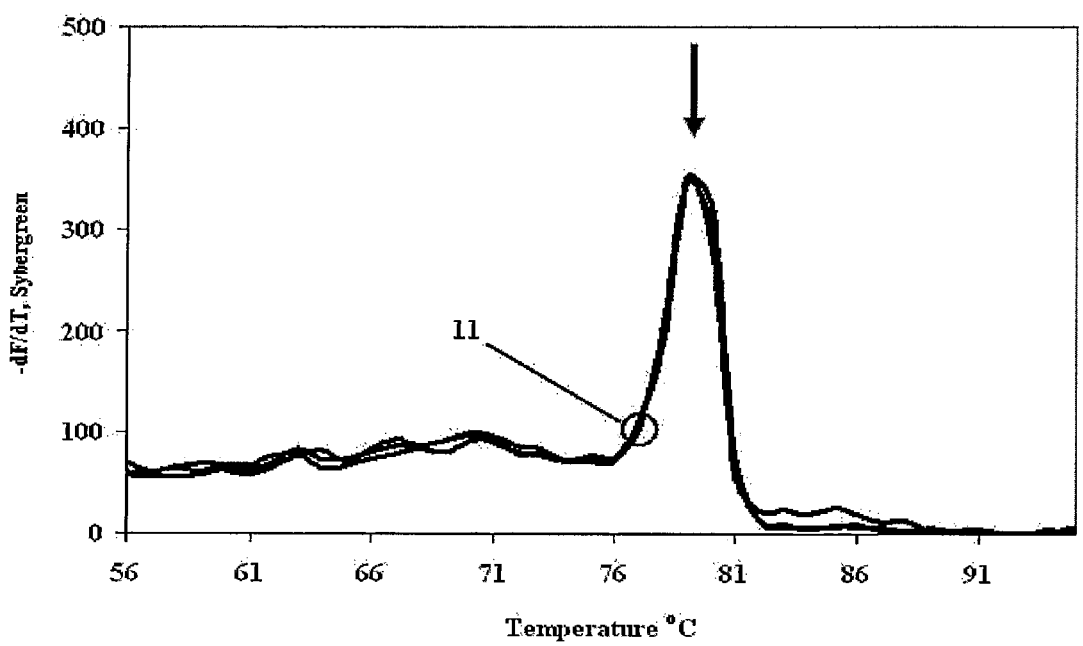
FIG. 1 presents melt curves for replicates of a LATE-PCR amplification described in Example 1 utilizing additive 16 merA at a concentration of 300 nM.

References are made to melting temperatures (Tm) of double-stranded additives, primers and probes. By definition, Tm means the temperature at which a double-stranded oligonucleotide is 50% double-stranded and 50% single-stranded. For additives, Tm means a calculated Tm of a double-stranded oligonucleotide not accounting for any effect of substituent modifiers. Tms of double-stranded additives presented in this specification were calculated according to Markhan and Zuker (2005) DINAMELT web server for nucleic acid melting prediction, *Nucleic Acids Res.* 33:W577-W581, and Markham and Zuker (2008) UNAFOLD: software for nucleic acid folding and hybridization. In Keith, J. M., ed., BIOINFORMATICS, vol. II, *Structure, Functions and Applications*, No. 453 in *Methods in Molecular Biology*, Ch. 1, pages 3-31 (Humana Press, Totowa, N.J. ISBN 978-1-60327-428-9. In utilizing the referenced web server, the following inputs were made: concentration of each strand, in μM, as reported in the Examples; 70 mM for salt concentration; and 3 mM for magnesium concentration. Tms of probes and primers in LATE-PCR amplification reactions the start of amplification are referred to as $Tm_{[0]}$. $Tm_{[0]}$ can be determined empirically, as is necessary when structured probes are used, or calculated according to the "nearest neighbor" method (Santa Lucia, J. (1998) PNAS (USA) 95: 1460-1465; and Allawi, H. T. and Santa Lucia, J. (1997) Biochem. 36: 10581-10594) which is herein incorporated by reference in its entirety using a salt concentration adjustment. In our work, we use 0.07 M monovalent salt concentration, although other concentrations can be used.

References are made to modifying groups being located on terminal regions oligonucleotide strands. By "terminal regions" it is meant attached to a terminal 5' or 3' nucleotide or to an internal nucleotide not more than five, not more than three, or not more than two nucleotides from a 5' or 3' end. In some embodiments, terminal modifiers are attached to a 5' or 3' terminal nucleotide.

References are made to selectivity. By "selectivity" it is meant generally the preference of a DNA polymerase to extend recessed 3' ends when certain conditions are met. Generally speaking, recessed 3' ends bound to a target sequence are thermodynamically unstable, that is they alternately bind to and partially unwind from the strand to which they are hybridized. These ends can be said to be stable when binding to the target is favored by formation of more hydrogen bonds and unstable when they form fewer hydrogen bonds. According to this view, recessed 3' ends that are perfectly complementary to their targets are more stable than recessed 3' ends that are not perfectly complementary to their targets. Similarly, recessed 3' ends that are GC rich are generally more stable than recessed 3' ends that are AT rich, since GC dinucleotide pairs form three hydrogen bonds while AT dinucleotide pairs form two hydrogen bonds.

In accord with this understanding, one type of selectivity is the preference of a DNA polymerase to extend a recessed 3' end of a hybrid when the 3' terminal region, particularly including the terminal 3' nucleotide, of the recessed 3' end is perfectly complementary, that is, is hybridized with no mismatch. Stated another way, this type of selectivity is selectivity against a 3' terminal priming sequence that is not perfectly matched to its target. Selectivity against 3' terminal-region mismatches applies to primer-target hybrids, where it signifies the preference of a polymerase for a primer-target hybrid that is perfectly complementary at the 3' end of the primer over a primer-target hybrid having a mismatch at, for example, the 3' terminal nucleotide. Selectivity against 3' terminal-region mismatches also applies more generally to hybrids having recessed, extendable 3' ends formed by any two DNA strands in an amplification reaction mixture, such as may occur when one amplicon strand hybridizes to (that is, primes on) another amplicon strand.

A second type of selectivity is the preference of a DNA polymerase for a primer (or priming strand) having a 3' terminal region that is GC-rich rather than AT-rich, or stated another way, selectivity against a primer or other priming strand whose terminal region is AT-rich.

For selectivity of either type, the measure of selectivity is the difference ($\Delta C_T$) between the threshold cycle ($C_T$) of the signal from amplification of the non-preferred hybrid, for example the hybrid formed by a primer and a mismatched target and the $C_T$ of the signal from amplification of the preferred hybrid, for example the hybrid formed by a primer and a matched target. Improvement in selectivity due to the use of an additive is the net $C_T$ difference obtained by subtracting the $\Delta C_T$ without any additive from the $\Delta C_T$ that results with the additive.

Additives that reduce mispriming, inhibit DNA polymerase activity, increase DNA polymerase selectivity of either type, inhibit DNA polymerase exonuclease activity, or reduce scatter among replicate reactions, or any combination of the foregoing in primer-dependent DNA amplification reactions and nucleic acid detection assays employing such reactions, including PCR amplification reactions and PCR amplification assays can be included.

Chemical reagents that are soluble in DNA amplification buffer and include from one to four or from two to four, covalently bound moieties, which are referred to as modifying groups or, for short, modifiers, suppress mispriming and enhance polymerase selectivity for hybrids between primers and fully complementary target sequences. The covalently bound modifying groups are polycyclic (including but not limited to aromatic) moieties which, if bulky, are planar and can be configured to bind to a DNA polymerase having an exonuclease domain (active or inactivated) so as to suppress mispriming and enhance polymerase selectivity for hybrids between primers and fully complementary target sequences.

In some embodiments, the quencher Dabcyl can be used as a modifying group for these reagents.

These polycyclic moieties can be solubilized by attaching them to double-stranded oligonucleotides. Certain double-stranded oligonucleotides with from 1-4 polycyclic moieties, as described above, can be useful as additives for reducing mispriming, inhibiting DNA polymerase activity, increasing DNA polymerase selectivity, inhibiting DNA polymerase exonuclease activity, reducing scatter among replicates, or any combination of the foregoing in primer-dependent DNA amplification reactions and nucleic acid detection assays employing such reactions, including PCR amplification reactions and PCR amplification assays. The modified double-stranded oligonucleotides may comprise natural nucleotides, that is, they may be DNA, RNA, or mixtures of DNA and RNA. The modified double-stranded oligonucleotides may also comprise non-natural nucleotides, for example, LNA's and 2' O-methyl ribonucleotides. The amplification reactions may be symmetric or non-symmetric, including asymmetric PCR amplification reactions and, preferably, LATE-PCR reactions.

Figure 18A:
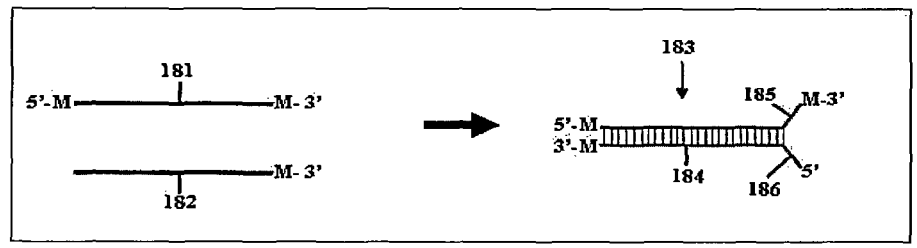
FIG. 18A is a schematic depiction of a modified double-stranded additive according to this invention formed from two linear (random coil) oligonucleotides and having single-stranded overhangs.
Figure 18B:
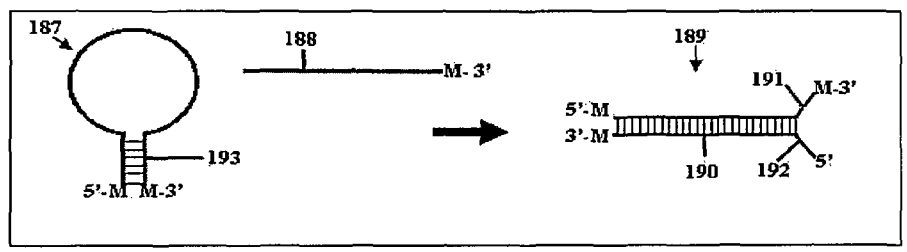
FIG. 18B is a schematic depiction of a modified double-stranded additive as in FIG. 18A, but formed from one linear oligonucleotide and one hairpin-forming oligonucleotide.
Figure 18C:
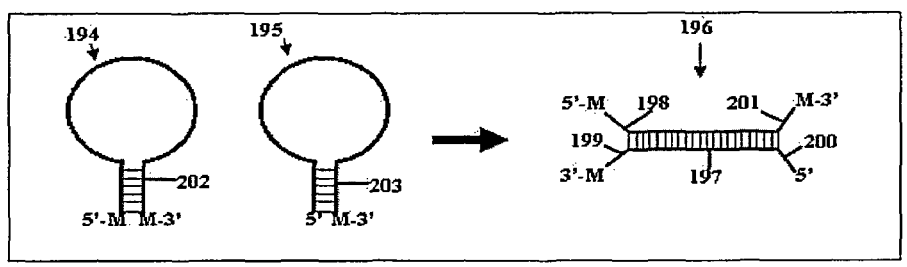
FIG. 18C is a schematic depiction of a modified double-stranded additive as in FIG. 18A, but formed from two hairpin-forming oligonucleotides.

The additives can be modified linear double-stranded DNA oligonucleotides in which the complementary nucleic acid strands are from 6-50, preferably 12-30, and more preferably 16-26, nucleotides in length. The modified double-stranded oligonucleotides may be blunt ended or may contain short overhangs of 1-8 nucleotides, preferably 1-5 nucleotides, on one or both ends. FIGS. 18A-18C depict several different embodiments with non-complementary terminal regions in the strands at one or both ends of an additive's double-stranded region. For purposes of illustration, all the constructions are shown with three modifying groups, M, having a particular placement, but it will be appreciated that embodiments such as these are not limited to the placement shown or to the inclusion of three modifier groups. FIG. 18A shows two partially complementary, random coil oligonucleotides 181, 182 that hybridize to form double-stranded additive 183, which includes double-stranded region 184 and single-stranded overhangs 185, 186. The melting temperature, Tm, of hybrid 184 can be adjusted by changing its length and GC content. FIG. 18B similarly shows two partially complementary oligonucleotides 187, 188 that hybridize to form double-stranded additive 189, which includes double-stranded region 190 and single-stranded overhangs 191, 192. Overhangs 191, 192 may comprise sequences that do not hybridize to one another even at low temperatures. Alternatively, the overhangs may comprise sequences that hybridize to one another only at low temperatures (Tm below the Tm of double-stranded region 184, as determined by degree of complementarity and GC content). The embodiment depicted in FIG. 18B differs from the embodiment shown in FIG. 18A in that one ologonucleotide, namely, oligonucleotide 187, when not hybridized to oligonucleotide 188, assumes a hairpin structure that includes a double-stranded stem 193 up to six nucleotides in length. FIG. 18C similarly shows two partially complementary oligonucleotides 194, 195 that hybridize to form double-stranded additive 196, which includes double-stranded region 197 and single-stranded overhangs 198-201. In the embodiment shown in FIG. 18C both oligonucleotides 194 and 195, when not hybridized to one another, assume hairpin structures that include stems 202 and 203, respectively. Examples 16 and 17 utilize the structures shown in FIG. 18C. For additives in which either or both strands form a hairpin, or stem-loop, structure, the Tm of each stem is higher than the Tm of the double-stranded region, to ensure formation of the hairpin during use, but not so high as to prevent formation of the double-stranded conformation of the additive in a reasonable period of time when the temperature of the reaction is decreased during use. In some embodiments, in which neither oligonucleotide strand serves as an amplification primer or as a probe, both 3' ends are blocked to prevent extension by a DNA polymerase. Blocking may be achieved by covalently linking a modifying group to the 3' terminal nucleotide of a strand or otherwise blocking extension, as, for example, by including a 3' terminal phosphate group. Additives can include double-stranded oligonucleotides that are at least 50% double-stranded at 32° C., which is as high a temperature as is likely to be encountered during assembly of an amplification reaction mixture.

From 1-4 modifying groups, preferably 2, 3 or 4 groups, are included in the linear double-stranded oligonucleotides. The modifiers are covalently attached to additive strands in their terminal regions, that is, at a terminal nucleotide or at a nucleotide that is not more than five, preferably not more than two, nucleotides from a terminal nucleotide. Some embodiments utilize modifiers attached to terminal nucleotides of the double-stranded oligonucleotides. The modifiers can be covalently linked to oligonucleotide strands. Covalent linking of modifying groups is well known in the art for incorporating fluorophores and quenchers, for example.

The modifying groups can be moieties that are polycyclic, including but not limited to polyaromatic, and, if bulky, have an overall planar aspect. Examples include digoxigenin, a plant steroid; coumarin, a bicyclic aromatic; QSY-21, a small polyaromatic compounds used as quenchers, that are not planar. Fulvic and humic acids are believed to be included. In some embodiments, the modifying group is the well-known quencher Dabcyl, which is polyaromatic, bulky and planar. Thus, modifying groups can be polycyclic moieties that do not have bulky portions that are non-planar, and preferably are polyaromatic.

Additives can include a linear double-stranded DNA oligonucleotide with various possible configurations of one, two, three and four modifying groups. With one terminal modifying group, there are four possible configurations: the modifier may be attached to the 3' or 5' terminal nucleotide of either strand. With two terminal modifying groups, there are six possible configurations; with three terminal modifying groups there are four possible configurations; and with four modifying groups there is only one possible configuration. Attachment of modifiers to internal nucleotides of terminal regions creates additional possible configurations. In all cases in which a strand is not a primer and a modifying group is not attached to a strand's 3' terminal nucleotide, that nucleotide is otherwise blocked, as by a phosphate group (identified in sequences in the Examples as "p").

In certain embodiments, one strand serves also as a primer, and its 3' terminus is not blocked. In certain other embodiments, one strand serves as a detection probe, in which case its 3' end can be blocked, for example by a terminal modifying group, a terminal fluorophore, or a terminal phosphate group. For primer embodiments, a single-stranded amplification primer can be converted into an additive by including a single-stranded oligonucleotide that is complementary to the primer, which we call the reverse complement sequence, so that it forms a double-stranded hybrid with the primer. The hybrid can function as an additive when it is double-stranded. The hybrid can include three modifiers, such as Dabcyl groups. The Tm of the reverse complement sequence to the primer strand can be designed to be 5-30° C., preferably 15-25° C., lower than the Tm of the primer strand to its amplification target sequence. To achieve the difference in Tm's, the reverse complement sequence may be rendered partially complementary to the primer strand by making it either shorter or mismatched at one or more nucleotide, or both. For probe embodiments, a labeled, single-stranded hybridization probe can be converted to an additive similarly to the conversion of a primer and has a Tm that is similarly lower than the Tm of the probe-target hybrid. Preferred probe embodiments include a probe strand having a fluorophore and a quencher and a reverse complement sequence having two terminal quenchers.

Primer-dependent amplification reaction mixtures for amplifying at least one DNA or cDNA target can be included. The reaction mixtures include at least one of the foregoing additives as well as target nucleic acid and amplification reagents that include primers, a DNA polymerase, dNTP's and, generally, amplification buffer. If the amplification mixture is for an amplification assay that includes both amplification and homogeneous detection of double-stranded amplification products, single-stranded amplification products, or both, the reaction mixture can include at least one reagent for product detection, preferably fluorescence detection. Preferred reagents for detecting double-stranded amplification products are DNA dyes, such as SYBR Green. Preferred reagents for detecting single-stranded products are fluorescently labeled detection probes whose hybridization to single-stranded products causes a detectable fluorescent signal change or whose hybridization to single-stranded products during amplification leads to a detectable fluorescent signal change. Numerous homogeneous detection reagents are known in the art, and any suitable detection reagent or reagents can be used. Other reagents can also be used. If target nucleic acid that is included is an RNA target sequence, the reaction mixture will include reverse transcriptase.

Reaction mixtures can include multiple primer pairs for multiple targets for multiplex amplifications and assays. Example 5 illustrates a reaction mixture for a duplex LATE-PCR assay for two target sequences that includes two primer pairs and a fluorescent probe for each amplified product. Example 8 illustrates a reaction mixture for a highly multiplexed amplification, a twelve-plex that contains twelve primer pairs for twelve different targets. If an additive includes one of the primer strands, the reaction mixture can further include the appropriate reverse complement sequence. Reaction mixtures can be PCR reaction mixtures, and in some embodiments LATE-PCR reaction mixtures. Reaction mixtures may include a combination, or mixture, of two additives. Such a mixture may comprise four strands or, if two additives share a common strand, three strands. Reaction mixtures can include at least one modified, double-stranded additive at a total concentration of up to 2000 nM, preferably up to 1000 nM and more preferably up to 600 nM. If the reaction mixture includes a mixture of additives, the total concentration of additives can remain as stated.

Methods for primer-dependent amplification of one or more DNA or cDNA target sequences and primer-dependent amplification of one or more DNA or cDNA target sequences with homogeneous detection of amplification products (that is, amplification assays with homogeneous detection) utilizing reaction mixtures described above are provided. Amplification methods and amplification assay methods may include isothermal amplification reactions or thermal cycling amplification reactions. In one embodiment, the amplification method can PCR and in some embodiments, LATE-PCR. The additive or combination of additives selected to be used in a particular amplification or amplification assay, and its or their amount(s), depends on the effect desired and on the temperatures to be utilized during amplification. Isothermal amplifications may include only a reaction mixture preparation temperature, typically room temperature, followed by an isothermal amplification reaction at a single reaction temperature, for example, 37° C. PCR and other thermal cycling amplification methods include a reaction mixture preparation temperature followed by numerous thermal cycles that include a primer annealing temperature (annealing temperature), a primer extension temperature (extension temperature), and a strand denaturation temperature (melting temperature). Although the annealing temperature and the extension temperature may be the same, it is more common for the annealing temperature to be 5-20 degrees Celsius (° C.) below the extension temperature. LATE-PCR assays may further include a low-temperature detection step in some or all of the thermal cycles, during which the temperature of the reaction mixture is reduced below the annealing temperature to permit low-temperature probes to bind to their target sequences. Amplification reactions may be interrupted at an intermediate point for performing some operation that may include low temperature (below the annealing temperature), after which the amplification reaction can be resumed. Amplifications may take advantage of other ways of reducing mispriming. For example, the DNA polymerase that is used may be a hot-start polymerase. Further, the primers that are used may be designed to have AT-rich 5' ends, including where necessary by adding extensions. Additionally or alternatively, the 3' ends of primers can be designed to be either GC-rich or AT-rich so as to alter polymerase inhibition in amplifications and amplification assays. Products of amplification reactions can be suitable for sequencing, including but not limited to dideoxy sequencing.

Amplification assays may include real-time homogeneous detection of single-stranded products, double-stranded products, or both, at multiple times during amplification of DNA target sequences, for example, during some or all cycles of a PCR amplification reaction. As stated above, fluorescence detection can be used. Alternatively, amplification assays may include homogeneous detection at end-point following completion of an amplification reaction. Detection may include melting amplification products and detecting fluorescence change as a function of temperature. Detection may be qualitative or quantitative. For targets that are RNA, assays can include reverse transcription.

Reagent kits for performing amplifications and amplification assays are provided. Such kits can include reagents needed to prepare reaction mixtures, including primers for at least one target sequence, dNTPs, a DNA polymerase, and at least one modified double-stranded additive, as described above. Kits for amplification assays can also include at least one detection reagent, such as, a DNA fluorescent dye or a fluorescently labeled hybridization probe. Amplification kits and amplification assay kits may also include reagents for sample preparation, for example, cell lysing reagents, reagents for nucleic acid isolation, and reverse transcriptase. Amplification assay kits may include control target sequences and primers for their amplification.

Selection of an additive or mixture of additives can take into account their properties of DNA polymerase inhibition, selectivity against 3' terminal primer mismatches, selectivity against AT-rich primer 3' terminal regions, inhibition of polymerase exonuclease activity, mispriming suppression, and reduction of scatter among replicates. An additive's effect depends, in turn, on the inherent properties of the additive, its concentration, its melting temperature, and its concentration. For example, inherent polymerase inhibition tends to increase with the number of modifiers included in the additive, and the effective inhibition of an additive increases with its concentration. Selectivity against a 3' terminal primer mismatch has been found to correlate with blocking exonuclease activity of DNA polymerases that have that activity or at least have an exonuclease site. This may be due to blocking the exonuclease site of the enzyme by the additive.

Additives can be added to amplification reaction mixtures in concentrations that are effective for one or more of the functions of suppressing mispriming, increasing polymerase selectivity against hybrids having recessed 3' terminal sequences that are not perfectly complementary, increasing polymerase selectivity against hybrids having recessed 3' terminal sequences that are AT-rich, reducing scatter among replicate reactions, inhibiting polymerase 5' exonuclease activity, and inhibiting polymerase activity. Because additives interact with DNA polymerases, the concentration required will vary with the concentration of DNA polymerase that is included in an amplification reaction mixture. Determination of the additive concentration required to be effective for one or more of the foregoing functions, as well a determination of an optimum concentration, can be determined routinely by trying several concentrations in the amplification reaction or amplification assay for which an additive is intended, as demonstrated in the Examples below. Example 3, for instance, reports empirical trials of several additives at several concentrations to determine the effects of the additives at various concentrations to aid in selection of a preferred additive, to ascertain the effective concentration, and to determine an optimum concentration for a particular purpose in a particular LATE-PCR assay. For Taq DNA polymerases, which are the most commonly used polymerases for amplification reactions and assays, a typical polymerase concentration can be 1.25 units in 25 microliters (μl0r ul) of reaction mixture. In some embodiments, no more than 2000 nanomolar (nM) of additive is required, in some embodiments, no more than 1000 nM, and in some embodiments, not more than 600 nM. For Tfi DNA polymerases, which can be included in reaction mixtures at higher concentrations than Taq DNA polymerases, the same concentrations of additives are generally effective.

For an additive to act as a "hot start" reagent, it is preferred that the additive nearly or completely inhibit the polymerase activity of the polymerase being used, for example, Taq DNA polymerase, at temperatures below the reaction temperature of an isothermal amplification and below the annealing temperature of a thermal cycling reaction such as PCR. For this purpose, the additive can have a high inhibitory effect on polymerase activity and a melting temperature (Tm) that is at least 32° C. and equal to or below, preferably, 1-15° C. below, more preferably 1-5° C. below, the isothermal reaction temperature or the PCR, and at a concentration sufficiently high to completely or at least substantially inhibit the polymerase activity. As additives are not irreversibly denatured by being melted apart at temperatures above their Tm, the additives will function during the isothermal reaction of PCR thermal cycling every time the temperature is lowered sufficiently for the additive to become double-stranded, for example, during a low-temperature detection step, as is sometimes used in a LATE-PCR assay.

An additive can also act to reduce mispriming and increase polymerase selectivity at the reaction temperature of an isothermal amplification or at temperatures above the annealing temperature of a PCR amplification, particularly at the extension temperature. For this purpose, an additive can have low to modest inhibitory effect on polymerase activity and a melting temperature that is not more than 2° C. below, preferably at least equal to, and more preferably above, the isothermal reaction temperature or the PCR extension temperature, and at a concentration that is only as high as necessary to achieve the desired effect without unduly inhibiting the efficiency of the reaction. Here again, because the additives are not irreversibly denatured during the strand-melting step of PCR cycles, the additives can function to increase polymerase selectivity during every PCR cycle as the temperature is lowered for the strand-melting temperature to the annealing temperature or below.

Additives may be used singly or in combination. A mixture of two modified double-stranded oligonucleotides may include four strands or, if the two additives share a common strand, three strands. Three-strand mixtures insert one less strand into a reaction mixture, which can be advantageous in embodiments wherein the additive is neither a primer nor a probe for any target sequence in an amplification reaction mixture. Using additives in combination imparts flexibility of design. For example, to suppress Type I mispriming, one may include a first additive that, by its inherent nature, Tm and concentration, is very inhibitory of polymerase activity below the primer annealing temperature of an amplification reaction, but that is single-stranded during amplification so as not to inhibit the polymerization reaction. In combination with such an additive, to suppress Type II mispriming and where applicable, Type III mispriming during amplification, one may include an additive that is double-stranded during primer annealing but that minimally inhibits polymerase activity during primer extension.

Oligonucleotide reagents that interact directly with a DNA polymerase enzyme used in either an isothermal DNA amplification reaction or a thermal cycling DNA amplification reaction, such as a PCR reaction, are provided. Oligonucleotide reagents can act in amplification reactions during all steps in which they are double-stranded. They can have the effect of both suppressing mispriming and increasing polymerase selectivity, including the preference of the DNA polymerase to extend recessed 3' ends that are perfectly complementary to the strands to which they hybridize in comparison to recessed 3' ends that are imperfectly complementary to the strands to which they hybridize. Mispriming may be considered according to different types. Type I is mispriming that occurs whenever the temperature of the reaction mixture is below the primer annealing temperature. It occurs during preparation of reaction mixtures prior to the start of amplification. It may also occur during amplification, if the temperature is reduced below the primer annealing temperature. Type II is mispriming that occurs during amplification whenever the temperature of the reaction mixture is at or above the primer annealing temperature but below the melting temperature of a primer that is present. Type III is mispriming that occurs during amplification that continues after a high concentration of amplification product (amplicon) has been made. Yet another manifestation of mispriming is primer-dimer formation, wherein one primer hybridizes to another primer or to itself and then undergoes extension to generate a short double-stranded amplicon, which can then amplify further or even multimerize and amplify further. It is useful to divide an amplification reaction into stages to consider mispriming possibilities. Mispriming creates an amplifiable product, so a mispriming event that occurs early in an amplification reaction will be amplified almost as if it were a target molecule. The following general description is for PCR reactions, but persons skilled in the art will appreciate its application to other amplification reactions. This general description of PCR is for illustration purposes only and is not intended to limit the types of amplication reactions that can be used.

Pre-Stage: Reagents are prepared and mixed at 25° C. or lower (for example, on-ice). The concentration of primers is highest during the Pre-Stage, which typically lasts for minutes. Usually, the number of targets is low or very low during Pre-Stage, and some or all of those targets may be single-stranded, depending on how the sample was prepared and whether or not it is a cDNA. Indeed, synthesis of cDNA using an enzyme such as reverse transcriptase is also a part of Pre-Stage when the reaction mixture used for cDNA synthesis also contains primers and a DNA polymerase, since these components of the reaction mixture can misprime under the conditions required cDNA synthesis, typically 5-30 minutes at temperatures in the range of 40-60° C. The Pre-Stage is terminated by heating to high temperature, for example, 95° C., to denature all double-stranded DNA in the reaction mixture. If the DNA polymerase has been added in an inactivated form, for example, antibody-bound DNA polymerase, this heating step activates the polymerase, a process known as "hot start."

Type I mispriming occurs during the Pre-Stage. Chances of Type I mispriming are enhanced, if the DNA polymerase is not a hot-start enzyme and if no other inhibitor of polymerase activity is included in the reaction mixture. Also, Type I mispriming occurs, if the hot-start modification of the polymerase or added inhibitors used to block polymerase activity fail to do so completely. Both primer-dimer formation and Type I mispriming are favored during the Pre-Stage because the temperature is low. Products of Pre-Stage mispriming will be amplified.

Early-Stage: This stage of the reaction is typically 10-15 thermal cycles of a PCR amplification. The thermal profile of each cycle of 3-step PCR includes a strand-melting temperature, a primer annealing temperature, and primer extension temperature. For 2-step PCR, primer annealing and primer extension are performed at the same temperature. The amount of time allotted for each step in the thermal cycles is typically seconds long. During the first and second thermal cycles primers first anneal to their target sequences within the full-length target and are intended to selectively extend only when on fully complementary target sequences. Primers anneal to and extend on both strands of the target and, if all goes perfectly, generate and then exponentially amplify two complementary strands of defined length. The tendency of product strands to hybridize to each other is low, because their concentrations are low.

Type II mispriming can occur during the Early-Stage if primers extend on allelic targets to which they are not fully complementary. It is not atypical for primers to have Tms several degrees or even more above the annealing temperature, which invites Type II mispriming Shorter annealing times and higher annealing temperatures (relative to the primer Tms) are more stringent than longer annealing times and lower annealing temperatures and therefore decrease Type II mispriming and increase polymerase selectivity. Products of Type II mispriming can be amplified during the remainder of amplification. Hot-start polymerase modifications do not apply here, because the first heating to high temperature irreversibly inactivates the hot-start antibody or enzyme alkylation. Thermally stable inhibitors, including those described here, will be functional during the first and subsequent annealing steps, because they are not irreversibly denatured by high temperature.

Middle-Stage: This stage of a PCR reaction is typically comprised of 10-25 thermal cycles and includes melting, primer annealing, and primer extension. The amount of time allotted for each step in the thermal cycle is typically seconds long. Primers anneal to and extend on both strands of the target and, under optimal conditions generate and then exponentially amplify two complementary strands of defined length that is determined by primer pairs.

In the case of real-time symmetric PCR assays, Middle-Stage typically includes product detection during either the annealing step or the extension step of the reaction. In the case of LATE-PCR reactions, the Middle-Stage may include product detection at a temperature that is lower than the annealing temperature and occurs after the extension step. Fluorescent signals using a hybridization probe typically become detectable late in the exponential phase of both symmetric and LATE-PCR.

Toward the end of the Middle-Stage in symmetric PCR, the concentration of the exponentially accumulating product strands grows high enough for hybridization of product strands during the primer-annealing step. Exponential amplification slows down and plateaus, because, it is believed, the polymerase binds to the double-stranded product of the reaction. In the case of LATE-PCR, the limiting primer runs out and terminates the exponential phase of the reaction before the concentration of the product strands becomes high enough to slow the reaction.

In LATE-PCR amplifications that include a low-temperature detection step, Type I and Type II mispriming can occur in the Middle-Stage, just as in the Early Stage. This is particularly a risk during the low temperature detection step in real-time LATE-PCR. Type III mispriming can also occur during the Middle Stage as the concentration of product strands increases. Mispriming of any type, whether during Pre-Stage, Early-Stage or Middle-Stage results in scatter among replicate reactions, which is particularly manifest as exponential amplification slows down.

Late-Stage: The Late-Stage of amplification is generally found only in LATE-PCR because symmetric PCR has reached plateau and been terminated by this stage. This stage of a LATE-PCR amplification is typically comprised of 10-25 thermal cycles that include steps of melting, primer annealing (excess primer only), and primer extension (excess primer only). The amount of time allotted for each step in the thermal cycle is typically seconds long. Each excess primer anneals to and extends on the extension product made by extension of its corresponding limiting primer (its Limiting-Primer Strand) and, if all goes perfectly, efficiently generates the Excess-Primer Strand, which accumulates linearly until it begins to out-compete the excess primer itself. Thus, LATE-PCR reactions slow down but do not plateau as do symmetric PCR reactions.

In the case of real-time LATE-PCR assays, this stage may include product detection at the primer annealing temperature or at a temperature that is lower than the annealing temperature and occurs after the extension phase. Fluorescent signals using a hybridization probe typically increase with approximately linear kinetics during this stage.

Type III mispriming can occur during the Late-Stage after a number of linear cycles, because the 3' end of the Excess Primer strand can misprime anywhere along another molecule of the Excess Primer strand. Thus, the probability of Type III mispriming increases as: 1) the concentration of single-stranded product increases; 2) the number of different single-stranded products in a multiplex reaction increases; 3) the temperature of the reaction is lowered; 4) the 3' ends, or bases near the 3' ends of the Excess Primer Strands are GC-rich and hybridize (misprime) more readily. Type III mispriming results in conversion of single-stranded DNA back into double-stranded DNA, which we refer to as "product evolution" (although products are incomplete or abnormal). Product evolution is manifest as a sudden late increase in the fluorescence using dyes that detect double-stranded products (an increase in slope after plateau), or a sudden decrease in fluorescence from probes that detect single-stranded DNA. Thus, Type III mispriming is similar to Type II mispriming in that the error can occur above the annealing temperature, but Type III mispriming is also similar to Type I mispriming in that the error can occur below the annealing temperature. Type II mispriming can, of course, occur during this stage as well, as can Type I mispriming, if a low-temperature step is included.

End-Stage: End-Stage in LATE-PCR does not involve additional amplification because double-stranded products are no longer melted apart. End-Stage is a post-amplification stage in which some operation is carried out. Most commonly the temperature is lowered below the annealing temperature to permit probe target hybridization (signal generation=anneal signal) and then the temperature is raised over time to melt probe-target complexes apart (loss of signal=melting). We refer to this as "Probe Anneal-Melt Analysis". Probe Anneal-Melt Analysis at End-Stage can be carried with or without real-time analysis during LATE-PCR amplification. Typically Probe Anneal-Melt Analysis after a Late-Stage of 10-15 cycles generates quantitative information about the number of target copies present at the start of the reaction.

Typically, mispriming does not occur during End-Stage or, if it does, it is not followed by additional amplification needed to make products of mispriming visible. And, as shown in Example 10, it is possible using the "ColdStop" protocol to carry out Probe Anneal-Melt Analysis during Late-Stage, then to resume amplification for additional cycles until End-Stage is reached, at which time Probe Anneal-Melt Analysis can be repeated. As shown in Example 10, there is less scatter among replicates when real-time analysis is not used before Probe Anneal Melt Analysis, because the frequency of Type III mispriming is reduced by omission of a detection step in each thermal cycle.

Although not intending to be bound by any theory, we theorize that modified double-stranded oligonucleotides, as described herein, interact directly with DNA polymerases to suppress all types of mispriming, that is, Type I, Type II, Type III and primer-dimers. We believe that the additives, when double-stranded, preferentially bind to the 5' exonuclease domains of DNA polymerases but also bind to the polymerase domains of DNA polymerases, if added in sufficient concentration to more than saturate the 5' exonuclease domains. Empirically, 300-600 nM concentration of additive per 1.25 Units of Taq DNA polymerase in a 25 µL reaction volume can be sufficient to saturate both the 5' nuclease domain and the polymerase domain.

Although not intending to be bound by any theory, we theorize that by saturating both domains at temperatures below the primer annealing temperature, additives, as described herein, prevent Type I mispriming by effectively shutting down the polymerase by a combination of mass action and binding due to the modifying groups. At temperatures above the primer annealing temperature, additives can be used in concentrations which do not saturate both the 5' exonuclease domain and the polymerase domain. At these temperatures, additives preferentially bind to and selectively inhibit the activity of the 5' exonuclease domain while leaving the polymerase domain largely free to carry out extension of correctly hybridized primers. By selectively binding to the 5' exonuclease domain, additives increase the selectivity of the polymerase domain by an allosteric effect.

Although not intending to be bound by any theory, we theorize that modifying groups, for example Dabcyl groups, contribute to the functioning of additives in ways that can be used in selecting one or more additives for a particular purpose. Even one 3' terminal modifying group can suppress mispriming that is potentially caused by the additive itself. However, 3' terminal modifying groups, whether one or two on a double-stranded oligonucleotide, do not function to increase polymerase selectivity against a mismatch at the 3' terminus of a primer. On the other hand, 5' terminal modifying groups, particularly two 5' modifying groups, can significantly enhance that polymerase selectivity. Inclusion of modifiers on both strands at one end of the double-stranded oligonucleotide (that is, one 5' modifier and one 3' modifier) can significantly enhance that selectivity even if the double-stranded oligonucleotide is not blunt-ended. Having two modifiers on both ends of a double-stranded oligonucleotide can be better for selectivity enhancement than having two modifiers on just one end, but double-stranded oligonucleotides with four modifying groups tend to lower the efficiency of the polymerization reaction more than do double-stranded oligonucleotides with one, two or three modifying groups. We theorize that the cause for this is that additives with four modifying groups bind more efficiently to polymerase domains than do additives with fewer modifying groups.

Suppression of Type I Mispriming

Additives include double-stranded oligonucleotides that are modified by the addition of 1, 2, 3 or 4 modifying groups, for example Dabcyl modifying groups, at or near the termini of the strands, that is, in the terminal regions of the strands. In some embodiments, there are 2-4 such groups, and in some embodiments, the groups are covalently attached to terminal nucleotides. In the Examples, additives as described herein, whether single additives or mixtures, are denoted by the prefix "EP" to distinguish them from other additives described for purposes of comparison. Example 1 demonstrates that additives suppress Type I mispriming without causing additional mispriming. In this example, a LATE-PCR amplification that produced incorrect product (product other than that defined by the primer pair, as determined by melt analysis) was used. Production of the wrong product indicates Type I mispriming. Two different additives comprising unmodified double-stranded oligonucleotides having the same length (16 nucleotides) but different sequences were tried as control additives in this amplification. One, 16 merA, added at a concentration of at least 300 nM caused the reaction to produce the correct product (FIG. 1). The other, 16 merB, did not (FIG. 2), even when added at concentrations of 600 nM or 1000 nM, and in fact caused mispriming. This inconsistency was in accord with the teaching of Kainz et al. that double-stranded oligonucleotides could suppress mispriming or could cause mispriming. The assay was repeated with additives that were modifications of the mispriming-causing oligonucleotide, 16 merB, the modifications being the inclusion of either one or two terminal Dabcyl modifiers. Inclusion of a single Dabcyl modifier, additive EP048 (FIG. 3) or additive EO049 at 600 nM concentration, suppressed mispriming as compared to 16 merB (FIG. 2), including mispriming caused by the unmodified oligomer. Inclusion of two Dabcyl modifiers, additive EP027, did so at only 300 nM concentration and gave quite an improvement when added at only 100 nM concentration (FIG. 4). As shown by the kinetic analysis of reactions containing additive EP027 at different concentrations (FIG. 5), additive EP027 at 300 nM concentration eliminated scatter among replicates, and 300 nM was judged to be the optimum concentration in this assay.

The assay of Example 1 was repeated with several other unmodified double-stranded oligonucleotides having lengths from 12 to 30 nucleotides. Results, reported in Example 1, confirmed that unmodified oligonucleotides were inconsistent regarding suppressing or causing Type I mispriming. As reported in Example 1, the assay was also repeated with a number of double-stranded oligonucleotides having lengths in the range of 8-22 nucleotides and having two modifiers that were Dabcyl, two modifiers that were digoxigenin, four modifiers that were Dabcyl, or four modifiers that were digoxigenin. Results confirmed that additives, as described herein, suppressed Type I mispriming. These results also demonstrate the influence of Tm for additives. (In this application the Tm of an additive means the calculated Tm of its unmodified double-stranded sequence, as defined above. Modifiers tend to increase actual Tm slightly, perhaps 1-2° C., which the reader can take into account). To suppress Type I mispriming, it is preferred that additives remain double-stranded up to, or nearly up to, the primer annealing temperature and the primer Tm's. In Example 1, the primer annealing temperature for the first 10 cycles was 55° C. While good results were obtained in all cases at 600 nM concentration with additives having Tms ranging from 37° C. to 63° C. in Example 1, it was only additive EP021, the additive with the lowest Tm, that did not also give good results at 300 nM. The additives that performed best at concentrations of 100 nM and 50 nM had Tm's of at least 60° C. For suppression of Type I mispriming in PCR amplification reactions, additives can have Tms of at least 32° C., more typically at least 50° C., and more preferably at least 60° C.

Figure 6:
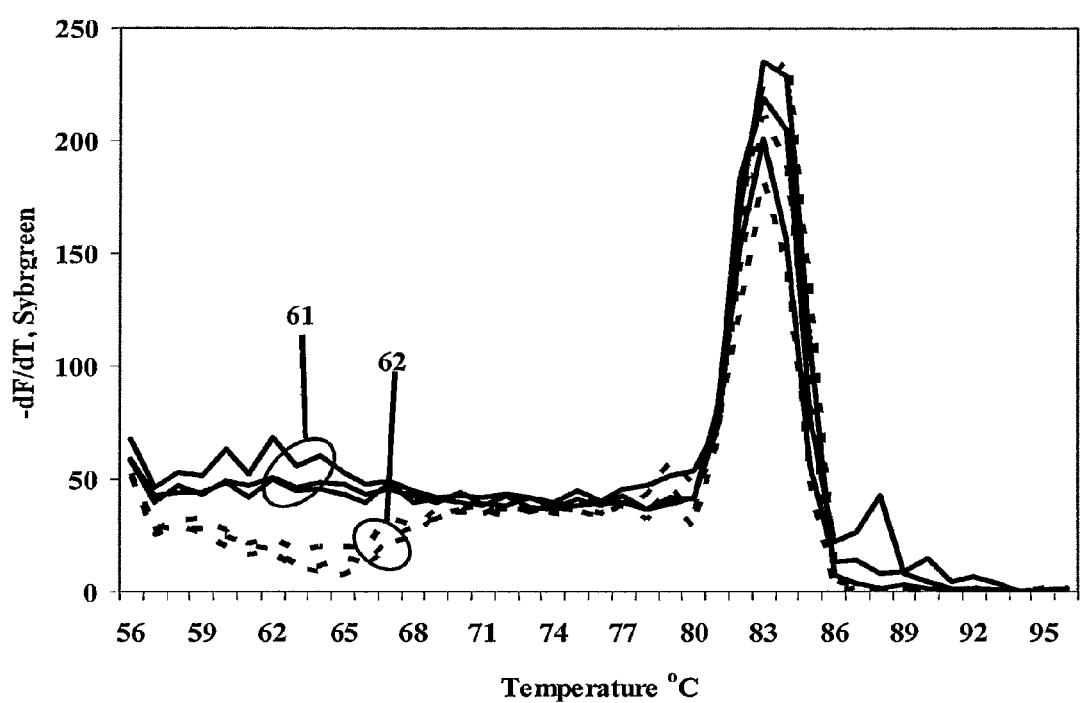
FIG. 6 presents melt curves for replicates of a LATE-PCR amplification described in Example 2 utilizing additive 22 merA at a concentration of 100 nM and additive EP003 at a concentration of 100 nM.

As a further check on the consistency with which additives as described herein suppress Type I mispriming, we performed a LATE-PCR assay for a different target sequence using different primers. In this assay, as reported in Example 2, we compared twelve additives to the unmodified double-stranded oligonucleotide, oligonucleotide 22 merA, that performed well in the assay of the first part of Example 1. The additives all had lengths of 22 nucleotides, several different sequences, and several different configurations of two, three or four terminal Dabcyl modifiers. All were at least as good as additive 22 mer A in suppressing mispriming at 300 nM concentration, and nearly half did so at a lower concentration of only 100 nM. FIG. 6 is melt curves for additive EP003 and additive 22 merA, showing that only the additive suppressed mispriming at 100 nM concentration.

Example 9 illustrates a quantitative LATE-PCR assay to measure polymerase activity of a DNA polymerase prior to the first thermal cycle. This same assay can be used to quantify and compare the DNA polymerase inhibitory capacities of additives, which can be assayed over a broad range of concentrations, temperatures, and incubation times. The initial reaction mixture includes a high concentration of two oligonucleotides (62 and 75 base pairs, respectively) capable of annealing to each other at their 3' ends to form a hybrid that is 27 base pairs long and has a calculated Tm of 60° C. They also have priming sites at their 5' ends. Amplification primers are not included in the initial reaction mixture. The thermal profile of the reaction begins with an isothermal soak at 50° C. for 10 minutes. During this step the overlapping oligonucleotides can prime themselves, that is, hybridize and be extended by active DNA polymerase. To the extent that this occurs, there will be created copies of a double-stranded target for the primers, which are added to the reaction mixture prior to thermal cycling. Inhibition of the activity of the polymerase activity during the long incubation at 50° C. will reduce the number of copies of target formed during this step.

After the long 50° C. incubation, high Tm primers are added, and a 2-step LATE-PCR amplification is performed to amplify whatever targets had been made. The primer annealing temperature use for amplification (72° C.) is well above the Tm of the overlapping nucleotides so that additional double-stranded targets are not generated. In this assay, the number of cycles required to generate a detectable level of product (observed with either SYBR Green or a probe to the Excess-Primer-Strand) depends on how many full length strands were generated during the initial isothermal incubation of the partially complementary oligomers. This, in turn, depends on how active the DNA polymerase was during isothermal incubation due to the presence/absence of any potential enzyme inhibitor(s), such inhibitors, of known composition and concentration, having been added to the reaction mixture when it was first assembled on ice and prior to addition of the overlapping oligonucleotides.

Figure 13:
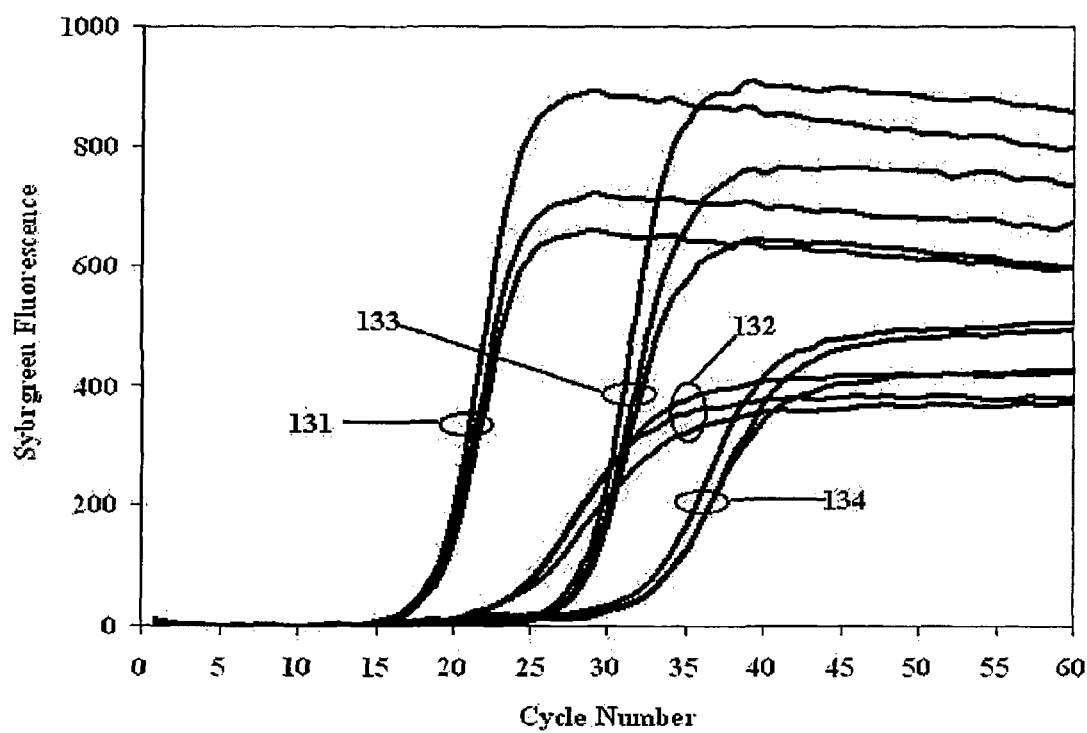
FIG. 13 is a graph of SYBR Green fluorescence as a function of amplification cycle number for replicates of a LATE-PCR amplification described in Example 9 utilizing Taq DNA polymerase with no additive, Taq DNA polymerase and antibody with no additive, Taq DNA polymerase with additive EP046 at a concentration of 600 nM, and Taq DNA polymerase and antibody with additive EP046 at a concentration of 600 nM.

We tested additives in this quantitative assay, including additives having Tm's at or below the 50° C. incubation temperature (EP020, Tm 50° C.; EP022, Tm 45° C.) and an additive having a Tm substantially above the incubation temperature (EP046, Tm 67° C.). The additives having the lower Tm's would have been at least substantially single-stranded during the 50° C. incubation, while high-Tm additive EP046 would have been double-stranded. Incorporation of the low-Tm additives into the reaction mixture resulted in no delay of the $C_T$, but incorporation of EP046 at a concentration of 600 nM did delay the $C_T$, whether the polymerase was Taq or Taq-plus-antibody. Kinetic curves for additive EP046 are shown in FIG. 13. FIG. 13 reveals that in the absence of any DNA polymerase inhibitor the 3' ends of the overlapping oligonucleotides hybridized to each other and extended. Addition of the antibody with the polymerase for hot-start partially inhibited Type I mispriming, by about 1000-fold, but further addition of 600 nM EP046 inhibited Type I mispriming an additional 10-fold.

Figure 19A:
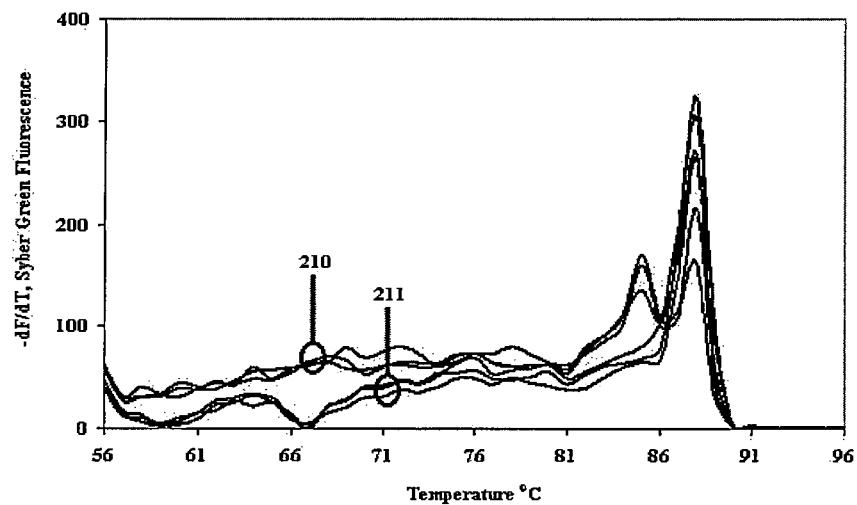
FIG. 19A presents melt curves for products of LATE-PCR amplifications with Taq polymerase plus antibody, with and without additive SL04, as described in Example 16.
Figure 19B:
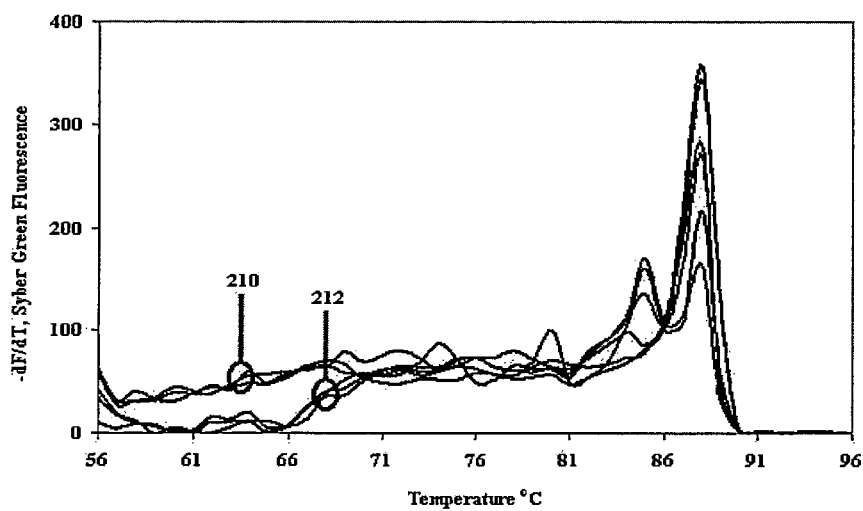
FIG. 19B presents melt curves for products of LATE-PCR amplifications with Taq polymerase plus antibody, with and without additive SL07, as described in Example 16.
Figure 19C:
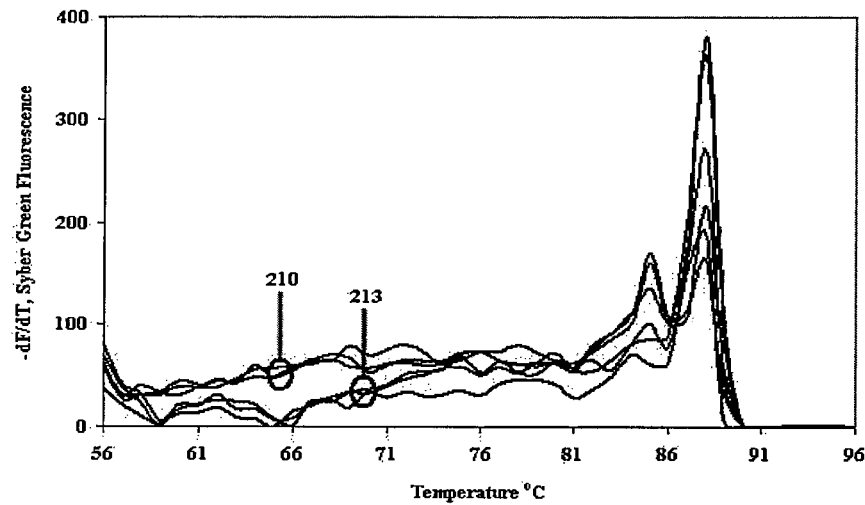
FIG. 19C presents melt curves for products of LATE-PCR amplifications with Taq polymerase plus antibody, with and without additive SL08, as described in Example 16.

Example 16 reports similar tests with additives having single-stranded overhangs six nucleotides in length and a double-stranded region of 22 base pairs. The additives all contained the same strand sequences but differed in the number and placement of modifiers, which were Dabcyl groups in the example. Both individual strands were hairpin-forming as depicted in FIG. 18C. The method of the tests included and isothermal soak at 50° C. for one minute (rather than for 10 minutes as in Example 9), followed by incubation on ice and then the LATE-PCR amplification. Melt-curve analysis showed that additives with two modifiers (FIG. 19A) and three modifiers (FIGS. 19B, 19C) reduced generation of incorrect product, and the additive with four modifiers (FIG. 19D) completely suppressed its generation.

Example 20 reports a test according to Example 9 that more strictly isolates Type I mispriming during the Pre-Stage. By using an additive that becomes single-stranded at the PCR annealing/extension temperature, possible Type II mispriming is eliminated. Based on the results reported in Example 20, we conclude that: a) hot-start antibody does not suppress DNA synthesis completely and that most products generated in the presence of the antibody result from Type I mispriming; b) products synthesized during incubation on ice are largely the result of Type I mispriming; c) additive EP010 acts to increase the specificity of product extension on ice, and because most products generated on ice are the result of Type I mispriming, EP010 inhibits most primer extension events on ice. Because melt curves of the amplified product containing additive EP010 (FIG. 23E) show that the double-stranded form is no longer present at 72° C., the temperature at which primer annealing and extension was carried out during amplification, the effects of EP010 observed in Example 20 are entirely due to the activity of EP010 during incubation at 50° C. and on ice, prior to the start of amplification. The same analysis of the additives used in Example 9 revealed that they have melt peaks (not shown) that are higher than that of EP010 and, therefore, the effects of the additives in Example 9 are due not strictly to steps prior to amplification, but also to steps during amplification.

Suppression of Type II Mispriming and Increasing Polymerase Selectivity in PCR Reactions Additives can suppress Type II mispriming and increase the selectivity of DNA polymerase for hybridized 3' terminal nucleotides of primers. To determine the selectivity against a mismatch at the 3' terminal nucleotide of the limiting primer during amplification in a LATE-PCR assay, we amplify a target that is perfectly complementary to both primers (matched target), and we separately amplify a target that is perfectly complementary to the excess primer but that contains a single mismatch to the 3' terminal nucleotide of the limiting primer. Alternately, as described below and demonstrated in Example 19, a 3' terminal mismatch can be created by use of a blocker oligonucleotide. We detect double-stranded product by DNA dye. "Selectivity" is the difference ($\Delta C_T$) between the $C_T$ of the signal from amplification of the mismatched target and the $C_T$ of the signal from amplification of the matched target. When performed on a sample containing no additive, this assay can demonstrate the basic selectivity of the polymerase for the primer/matched-target over primer/mismatched target, as well as the basic efficiency of amplification of the primer/matched target. For Taq DNA polymerase, the $\Delta C_T$ can be less than two amplification cycles. Improvement in selectivity caused by an additive is the gain in $\Delta C_T$ resulting from the inclusion of the additive in the amplification reaction mixture.

We tested unmodified double-stranded oligonucleotide and a number of additives in this selectivity assay. Results of assays run in triplicate are reported in Example 3. The $C_T$ differences ($\Delta C_T$) that are reported are the improvement in selectivity based on averages of the three replicates. Unmodified double-stranded oligonucleotide 22 merA, despite having a Tm slightly above the primer annealing temperature of the assay, improved the basic selectivity of the Taq DNA polymerase itself by fewer than two $C_T$ units at concentrations up to 300 nM. We tested numerous additives having the same length, 22 nucleotides, with various configurations of two, three, or four Dabcyl modifiers. As reported in Example 3, most configurations of two, three, or four Dabcyl modifiers improved the selectivity of the polymerase substantially, thereby reducing its tendency for Type II mispriming. As further reported in Example 3, we also tested three other modifiers useful in additives and fluorescein (FAM), not useful as a modifying group in additives. In at least some double-stranded oligonucleotides, each of the modifiers digoxigenin, coumarin and the quencher QSY 21 significantly improved selectivity as compared to additive 22 merA and as compared to a 22 nucleotide-long oligonucleotide with four FAM modifiers.

As reported in Example 17, we similarly tested amplification with various amounts of three additives having a double-stranded region of 22 base pairs and single-stranded overhangs six nucleotides in length. The sequences of the additives are given in Example 16. The additives comprised two strands that were hairpin-forming, as shown in FIG. 18C. Such additives with two and three Dabcyl groups as modifiers showed moderate improvement in selectivity ($\Delta C_T$) of greater than three $C_T$ units. The largest gain in selectivity was achieved with the additive having four Dabcyl groups as modifiers, namely, greater than six $C_T$ units.

Additives can also suppress Type II mispriming and increase polymerase selectivity in conventional symmetric PCR amplifications. Example 11 reports a symmetric PCR assay for two target sequences, one that was perfectly complementary to both primers and one that was perfectly complementary to one primer but contained a mismatch opposite the 3' terminal nucleotide of the other primer. The assay was run with no additive in the reaction mixture and also with a combination of two additives in the reaction mixture. That combination, designated EP043, included two double-stranded oligonucleotides with Dabcyl modifiers at combined concentration of 300 nM. In the assay of Example 11 the combination of Platinum Taq DNA polymerase, a hot-start DNA polymerase, and a highly discriminating allele-specific primer pair preferentially amplified the matched target by 7.84 $C_T$ values relative to the mismatched target. This detection specificity would be equivalent to detection of 1 matched target in an excess of 229 mismatched targets (i.e., 0.43% intended target) in a theoretical mixed population of both DNA targets. In comparison, addition of additive EP043 to the same symmetric PCR assay increased the specificity in favor of the matched target by another 4.75 $C_T$ values to 12.59 $C_T$ values, which would be equivalent to detection of 1 matched target in an excess of 6,615 mismatched targets (i.e., 0.02%), corresponding to a 26.7-fold increase in detection specificity.

In the experiment reported in Example 5, we performed a series of LATE-PCR amplifications with no additive, with a low-Tm additive, EP020 (Tm 51° C.), and with a higher-Tm additive, EP013 (Tm 62° C.). The experiment included the use of different primer annealing temperatures to test the amplification reaction under highly stringent conditions (high annealing temperature), moderately stringent conditions, and rather unstringent conditions (low annealing temperature as compared to the primer Tm's). Mispriming problems typically worsen as stringency is reduced. The assays were duplex assays for two target sequences, each having its own primer pair and its own detection probe.

The probes were molecular beacon probes that fluoresced upon hybridization to correct amplicons. Kinetic curves of probe fluorescences over the first 50 cycles are reported in FIGS. 9A-9F.

Figure 9A:
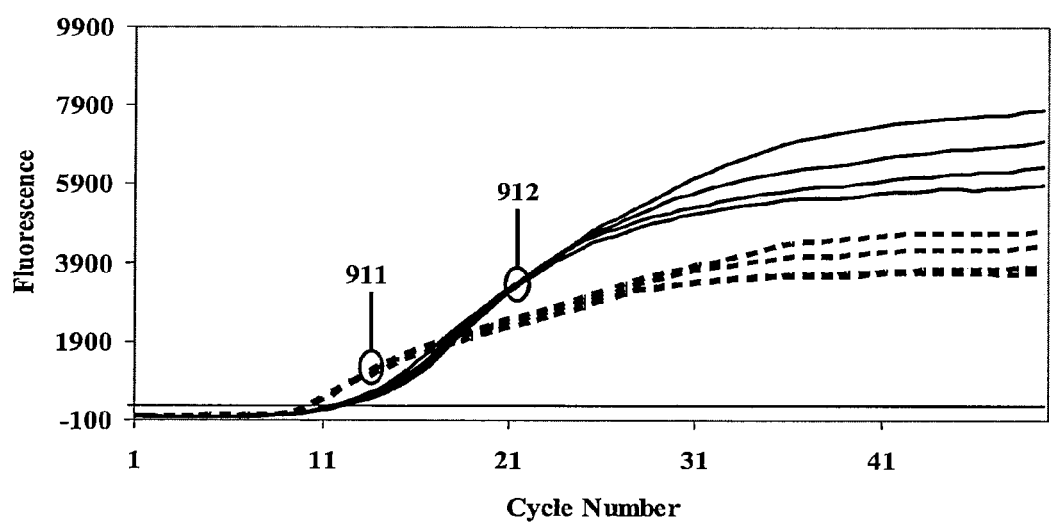
FIG. 9A is a graph of fluorescences from two probes as a function of amplification cycle number for replicates of a LATE-PCR duplex amplification described in Example 5 utilizing no additive and an annealing temperature of 65° C.
Figure 9B:
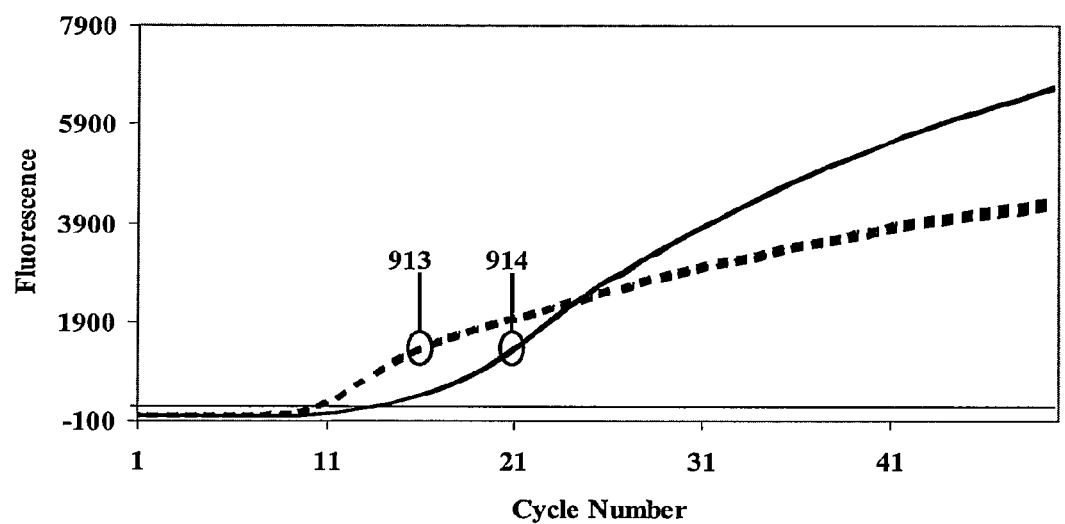
FIG. 9B is a graph of fluorescences from two probes as a function of amplification cycle number for replicates of a LATE-PCR duplex amplification described in Example 5 utilizing additive EP020 at a concentration of 400 nM and an annealing temperature of 65° C.
Figure 9C:
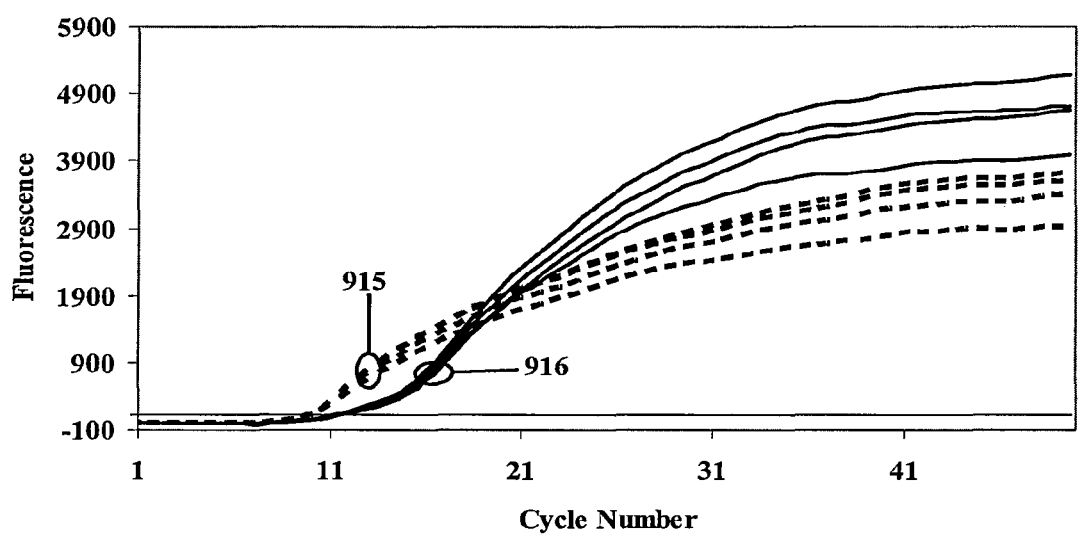
FIG. 9C is a graph of fluorescences from two probes as a function of amplification cycle number for replicates of a LATE-PCR duplex amplification described in Example 5 utilizing additive EP020 at a concentration of 400 nM and an annealing temperature of 60.7° C.
Figure 9D:
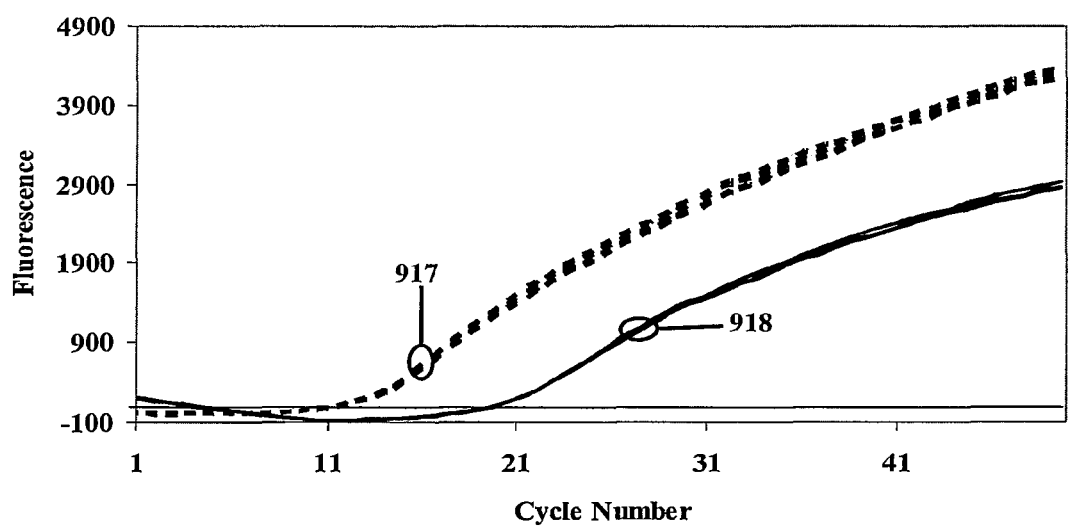
FIG. 9D is a graph of fluorescences from two probes as a function of amplification cycle number for replicates of a LATE-PCR duplex amplification described in Example 5 utilizing additive EP013 at a concentration of 300 nM and an annealing temperature of 66. ° C.
Figure 9E:
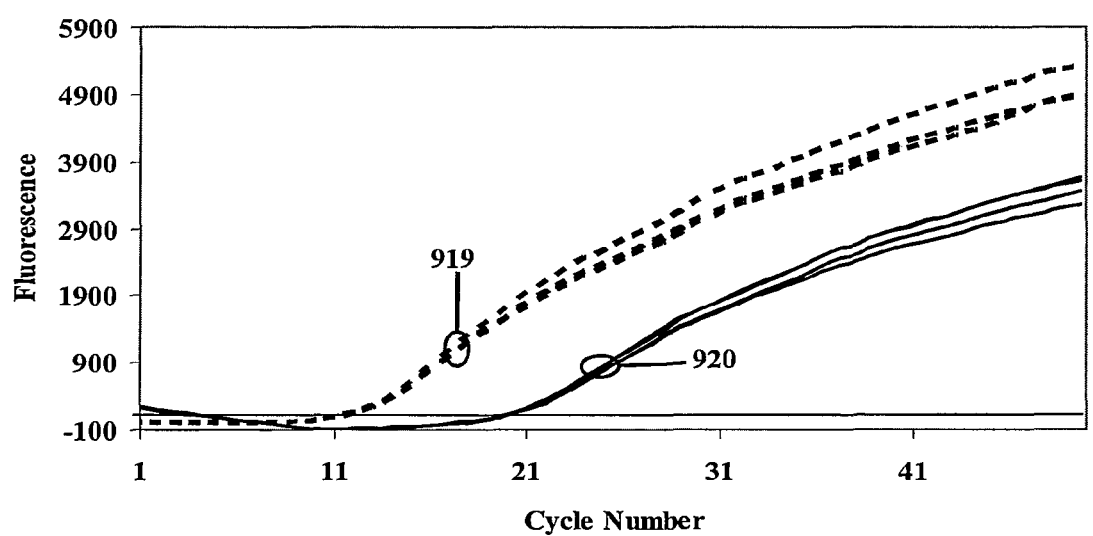
FIG. 9E is a graph of fluorescences from two probes as a function of amplification cycle number for replicates of a LATE-PCR duplex amplification described in Example 5 utilizing additive EP013 at a concentration of 300 nM and an annealing temperature of 64.2° C.
Figure 9F:
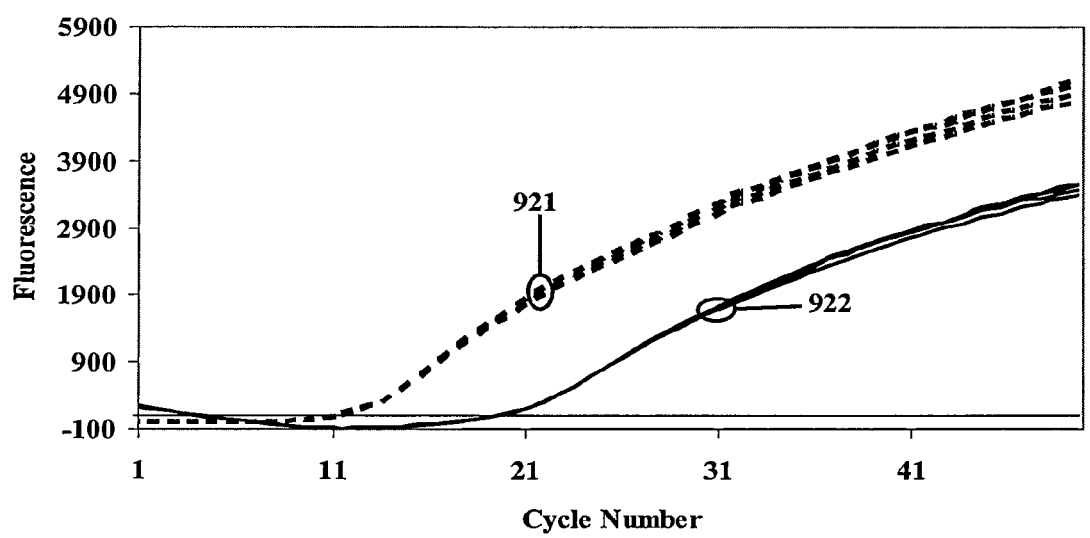
FIG. 9F is a graph of fluorescences from two probes as a function of amplification cycle number for replicates of a LATE-PCR duplex amplification described in Example 5 utilizing additive EP013 at a concentration of 300 nM and an annealing temperature of 60.7° C.

FIG. 9A shows that in this amplification reaction, Platinum Taq DNA polymerase, a hot-start polymerase, was not able to suppress Type I and Type II mispriming even under stringent conditions: 65° C. annealing temperature for all cycles. In contrast, both additives were able to do so (FIGS. 9B and 9D) at the concentrations used. With low stringency during the first 20 cycles (annealing temperature 60.7° C.), low-Tm additive EP020, which was not double-stranded at the annealing temperature, did not suppress Type II mispriming during amplification (FIG. 9C), but higher-Tm additive EP013 did (FIG. 9F). This shows that to suppress a type of mispriming occurring at a particular temperature, the additive should be double-stranded at that temperature. Comparison of FIGS. 9D-9F shows that with additive EP013 the least scatter among replicates was achieved using a stringent annealing condition for the first 20 cycles (66.5° C.), and that scatter was less at the least stringent condition (60.7° C.) than at an intermediate stringency (64.2° C.). This latter result is explained by the fact that the concentration of double strands, that is the functional concentration of the additive, was higher at the lower annealing temperature, illustrating the interrelationship between additive concentration and primer annealing temperature. It will be noted from FIGS. 9D-9F that with additive EP013, one target sequence amplified significantly less efficiently in the reaction than the other product sequence. We found that the difference could be much reduced by increasing the limiting primer concentration for the less efficient amplification from 50 nM to 100 nM.

Suppression of Type III Mispriming

Additives can suppress Type III mispriming Example 13 reports an experiment in which a LATE-PCR reaction was carried out to 65 cycles, long enough for Type III mispriming to occur and generate long double-stranded products resulting from the priming of one amplicon strand by another amplicon strand. We tested amplification with no additive; amplification with an additive having a Tm very close to the 58° C. primer annealing temperature (additive EP047, Tm 59.1° C.); and with a mixture of additives in which we replaced a minor amount, only about one-tenth, of additive EP047 with an additive that is double-stranded at temperatures above the annealing temperature. In this example, we used a higher Tm additive having a Tm (67.4° C.) substantially above the annealing temperature. A melt curve for three replicate amplifications with no additive showed that after 65 cycles of amplification the detected products had higher Tm's than the intended product, indicating that product evolution occurred. Kinetic curves showed that during the plateau phase there occurred a rise in the SYBR signal, also indicating that product evolution occurred. When the 5' end of the limiting primer was modified by the addition of a pair of A-nucleotides, the result remained the same: the melt curves showed products having higher Tm's than the desired amplicon. Inclusion of EP047 at 600 nM concentration with the unmodified limiting primer helped a little: it delayed product evolution by several cycles, and some detected products in two of three replicates had the correct Tm. Inclusion of EP047 at 600 nM and the use of the modified limiting primer decreased product evolution significantly and prevented it entirely in one of three replicates. Inclusion of additive mixture EP043 at 600 nM total concentration when used with the unmodified limiting primer decreased product evolution significantly and prevented it entirely in one of three replicates. Inclusion of EP043 at 600 nM and use of the modified limiting primer significantly decreased product evolution and prevented it entirely in two of three replicates. Thus, low concentrations of additives that are designed to have a Tm above the primer annealing temperature can suppress Type III mispriming. Further, the effect can be enhanced, if the 3' ends of amplicon strands are rendered AT-nucleotide rich, which can be accomplished, where necessary, by modification of the 5' ends of limiting primers.

Example 15 includes a no-additive control amplification assay for an RNA target sequence that showed severe Type III mispriming. It also shows that inclusion of additives, both double-stranded oligonucleotides and four-strand mixtures of double-stranded oligonucleotides, can suppress the Type III mispriming seen in the control. Example 15 demonstrates that additives, reaction mixtures, and methods do not inhibit reverse transcriptase used to convert RNA target into cDNA target.

Multiplexing

Figure 12:
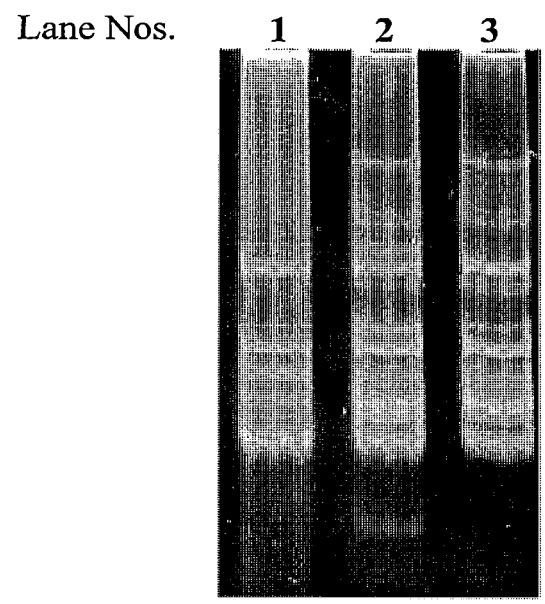
FIG. 12 is an electrophoretic gel showing products of a 12-plex LATE-PCR amplification described in Example 8 starting with 1000 copies of mitochondrial genomic DNA (target sequences) with no additive, with additive EP011 at a concentration of 300 nM, and with additive EP011 at a concentration of 600 nM.

Additives can enable highly multiplexed reaction for numerous target sequences with numerous primer pairs. Example 8 reports a 12-plex reaction, that is, multiplexed amplification of twelve target sequences using twelve primer pairs in a single reaction mixture. The amplification reaction was a LATE-PCR amplification of 65 cycles. The target sequences were included as human mitochondrial genomic DNA, which was included in the reaction mixtures with starting copy numbers of 1000, 100 and 10. In addition to a control amplification with no additive, additive EP011 was included in the reaction mixtures at concentrations of 300 nM and 600 nM. Following amplification, the reaction mixture was subjected to electorphoretic separation to ascertain whether or not the twelve intended products were made. In addition, dideoxy sequencing was performed to evaluate the amplicons. A photograph of the electrophoretic gel, FIG. 12, shows that amplification starting with 1000 copies, but with no additive, failed to produce the intended set of twelve products, but amplification starting with 1000 copies plus additive EP011 at 300 nM and 600 nM concentrations did produce the twelve products. The gel revealed that in this reaction EP011 at 300 nM concentration did not completely suppress mispriming, as evidenced by a band of lightweight product. Mispriming products were not seen in the gel when additive EP011 was included in the reaction mixture at 600 nM concentration. As a further analysis on this last product, it was sequenced. Sequencing results showed that a sufficient amount of each of the twelve amplicons had been generated to permit dideoxy sequencing by the simplified Dilute 'N' Go protocol. That was found not to be the case when the starting numbers of target were reduced to 100 and 10 copies. The results with 1000 copies of mitochondrial DNA show that mispriming was suppressed successfully both prior to amplification and during amplification.

Additive Mixtures

Figure 5:
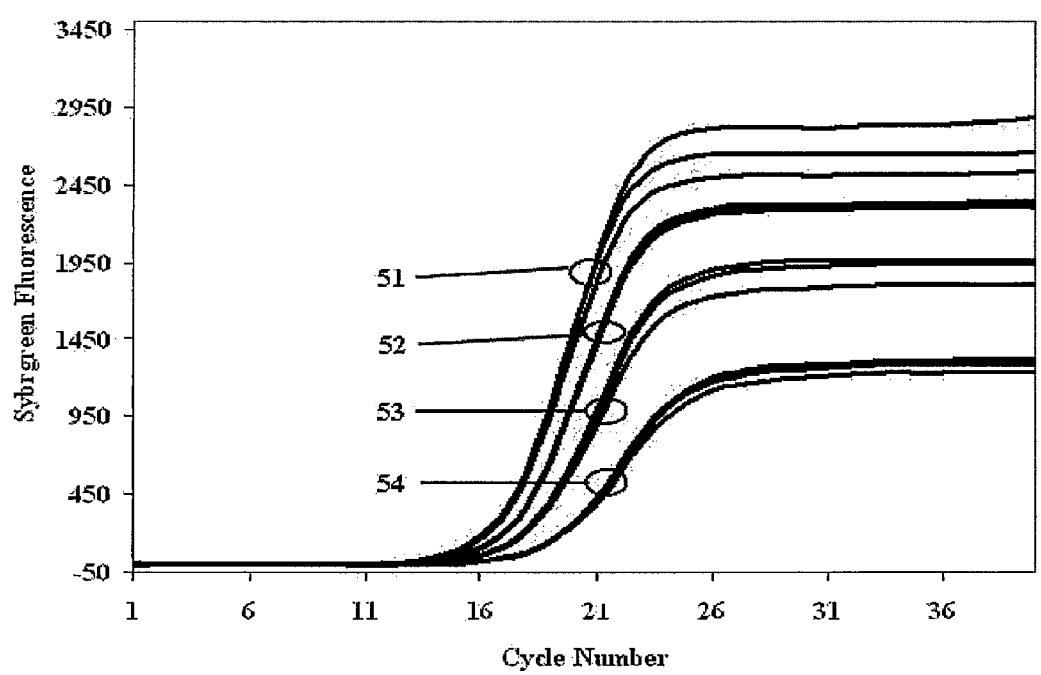
FIG. 5 is a graph of SYBR Green fluorescence as a function of amplification cycle number for replicates of a LATE-PCR amplification described in Example 1 utilizing additive EP027 at concentrations of 100, 300, 600 and 1000 nM.

A mixture of additives, additive mixture EP043, is discussed above in connection with Example 13. A reason to use a mixture can be understood by reference to Example 1, for example. The results show that suppression of Type I mispriming typically requires a moderately high concentration of additives. The kinetic curves in FIG. 5 show, however, that efficiency of the polymerization reaction tends to decrease as one increases the concentration of an additive having a Tm significantly above the primer annealing temperature. Yet Example 13 shows that a high-Tm additive can be needed to suppress Type III mispriming. A mixture of additives can be designed to suppress both types of mispriming while minimizing the reduction in amplification efficiency. In one embodiment, use a mixture that includes a higher concentration (300 nM to 1000 nM) of an additive that has a Tm close to the annealing temperature and a lower concentration (25 nM to 300 nM) of an additive that is double-stranded at temperatures above the annealing temperature, specifically, an additive that has a Tm several degrees above the annealing temperature (or the higher annealing temperature, if two are used in the reaction) can be used to suppress both types of mispriming. A mixture of additives may comprise four different strands, that is, two double-stranded additives that do not share a common strand. Alternatively, a mixture of additives may comprise three strands, that is, two double-stranded additives that share a common strand. The latter approach reduces the number of different strands included in an amplification mixture.

We tested mixtures of additives in the polymerase selectivity assay described in Example 3, both mixtures of unmodified double-stranded oligonucleotides and mixtures of additives. Experimental results are reported in Example 4. The mixtures tested were all three-strand mixtures in which two additives share a common strand. The mixtures all included a high-Tm additive having a Tm of 67.4° C., several degrees above the primer annealing temperature, which in this experiment was 62° C., and a low-Tm additive having a Tm in the range of 57.4-59.1° C., that is, slightly below the annealing temperature. Two of the mixtures, additive 041 and additive 042, contained unmodified double-stranded oligonucleotides. Both mixtures with unmodified oligonucleotides improved selectivity of the polymerase only relatively slightly, less than two amplification cycles, when added at concentrations of 75 nM for the higher Tm hybrid and 325 nM for the lower Tm hybrid. We also tested four mixtures of additives. In two (EP041, EP042), both double-stranded oligonucleotides contained three Dabcyl modifiers; in one (EP043), the higher Tm oligonucleotide contained three Dabcyls, while the lower Tm oligonucleotide contained four Dabcyls; and in one (EP045), both oligonucleotides contained four Dabcyls. All four mixtures improved selectivity more than did additives 041 and 042. FIGS. 7A-7D and 8A-8D are kinetic curves for mixtures EP043 and EP045, respectively, at the same total concentration of 600 nM but with the amount of the higher Tm hybrid varying from 25 nM to 100 nM. These curves reveal inhibition caused by additives and also scatter among replicates. The $\Delta C_T$ results and the kinetic curves taken together show that for each mixture there may be an optimum amount of the higher Tm hybrid in the mixture. For mixture EP043, (a) even the lowest concentration (25 nM) of the high-Tm component increases polymerase selectivity, (b) polymerase selectivity is not increased more by increasing the proportion of the high-Tm component up to 100 nM, and (c) none of the formulations significantly inhibits the efficiency of amplification of the primer to its matched target. For mixture EP045, (a) even the lowest concentration (25 nM) of the high-Tm component increases polymerase selectivity to a greater extent than EP043, (b) polymerase selectivity increases in proportion of the concentration of the high-Tm component, (c) all of the formulations inhibit the efficiency of amplification of the primer to its matched target, and (d) the extent of inhibition increases with the proportion of the high-Tm component. We judged the optimal formulation of mixture EP043 to be 75/600/525 nM, and we judged the optimal formulation of mixture EP045 to be 50/600/550 nM, as these formulations had low scatter among replicates.

Figure 21A:
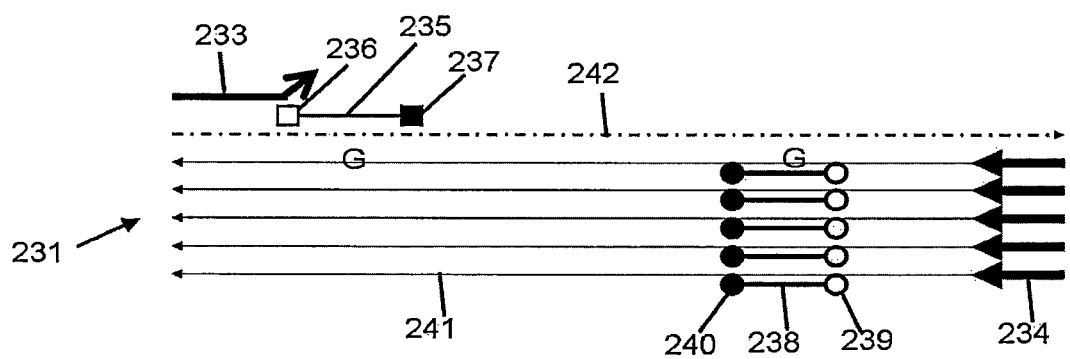
FIG. 21A is a schematic representation showing the action of a blocker oligonucleotide to create a 3' terminal mismatch between a limiting primer and a target to which the primer is perfectly complementary.
Figure 21B:
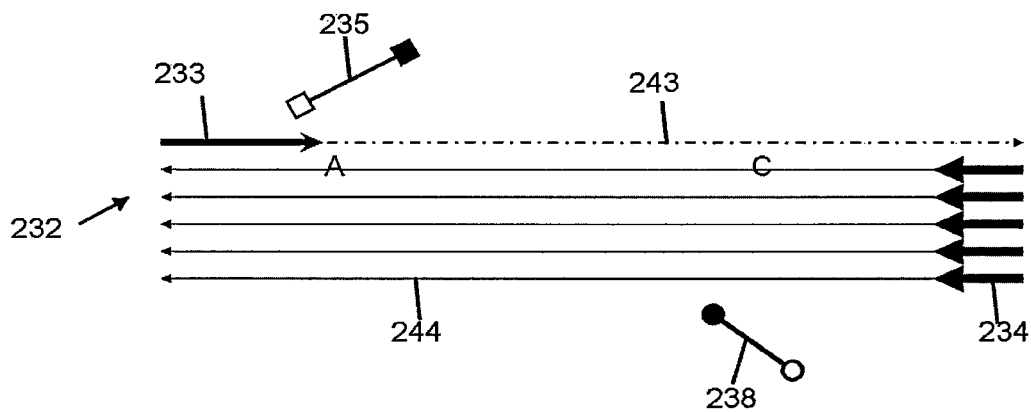
FIG. 21B is a schematic representation showing the action of a blocker oligonucleotide to create a 3' terminal mismatch between a limiting primer and a target to which the primer is perfectly complementary.

We also tested, in Example 19, additive mixture EP043 in an assay in which a 3' terminal mismatch is created by use of a blocker oligonucleotide. The scheme for that assay is illustrated generally in FIG. 21A and FIG. 21B. FIGS. 21A, 21B depict two double-stranded targets 231, 232, which differ by one base pair (either a G or an A in the excess-primer strand) shortly downstream from the binding site for limiting primer, arrow 233. The binding site for the excess primer, arrow 234, is also conserved between the two targets. Oligonucleotide blocker 235 is complementary to, and binds to, target 231 (FIG. 21A), which is the "mismatched" target to be selected against. Blocker 235 is allele-discriminating and mismatched against target 232 (FIG. 21B) and does not bind to it. Accordingly, primer 233 binds fully to target 232 and is extended, but the 3' terminus of primer 233 cannot bind to target 231, preventing extension. In FIG. 21A dashed line 242 is the limiting primer strand that would be created were primer 233 extended. In FIG. 21B dashed line 243 is the limiting primer strand created by extension of primer 233. Blocker 235 is shown with a terminal fluorophore 236 and a terminal quencher 237, but all that is required is that blocker 235 have a blocked 3' terminal nucleotide so as not to be extendable by a DNA polymerase during amplification. In the particular embodiment shown in FIGS. 21A, 21B, targets 231, 232 are shown to differ by another base pair (either a G in excess primer strand 241 in FIG. 21A or a C in excess primer strand 244 in FIG. 21B) downstream from blocker 235 and downstream from excess primer 234. A sequence-specific probe 238, labeled with fluorophore 239 and quencher 240, binds to the product of amplification of target 231 (the "mismatched" target) but not to the product of amplification of target 232, and signals upon hybridization. Probe 238 is optional in the sense that it is not used to enhance polymerase selectivity. It can be used, for example, for a melt analysis of the amplification product. Example 19 shows that in the case of induced-Type II mis-priming, when the additive reduces amplification efficiency, amplification is delayed in a thermal-cycle-dependent manner, and when the magnitude of the enhancement of selectivity due to the presence of an additive is also thermal-cycle dependent, the apparent enhancement of selectivity needs to be corrected for the thermal-cycle-dependent decrease in efficiency. A way to make that correction using a series of target dilution reactions in the presence of the blocker plus the presence/absence of the additive is demonstrated in Example 19.

We utilized additive mixture EP043 in the 12-plex of Example 8, discussed above, to see if sufficient amounts of all twelve products could be generated for sequencing. For these experiments we modified the limiting primer by adding AT-rich tails, and we extended the amplification reaction from 65 cycles to 80-90 cycles. With these modifications, all twelve intended products were successfully made in amounts needed for sequencing when additive mixture EP043 was included at strand concentrations of 50/600/550 nM and the starting amount of genomic mitochondrial DNA was only 100 copies or 10 copies. These results show that mispriming was prevented successfully prior to and during amplification, despite the fact that the extended length of the amplification presented a severe test for suppression of Type III mispriming.

In Example 12 we tested mixture EP043 at 600 nM total concentration in LATE-PCR amplification reactions that differed in the 3' end of the limiting primers. One reaction included a limiting primer having a GC-rich 3' end (GGC). The other reaction included a limiting primer having at AT-rich 3' end (AAG). As compared to a no-additive control, inclusion of additive EP013 (three Dabcyl modifiers, Tm 60° C.) in the amplification with the primer having the GC-rich 3' end resulted in relatively little reduction in efficiency of polymerization ($C_T$ delay of 4 cycles). As compared to a no-additive control, however, inclusion of the same additive at the same concentration with the primer having the AT-rich 3' end resulted in a significantly greater reduction in efficiency ($C_T$ delay of 11 cycles). In both reactions, which were continued for 70 cycles, additive EP013 significantly reduced scatter among four replicates as compared to the no-additive control.

ColdStop Protocol and all Types of Mispriming

Figure 14A:
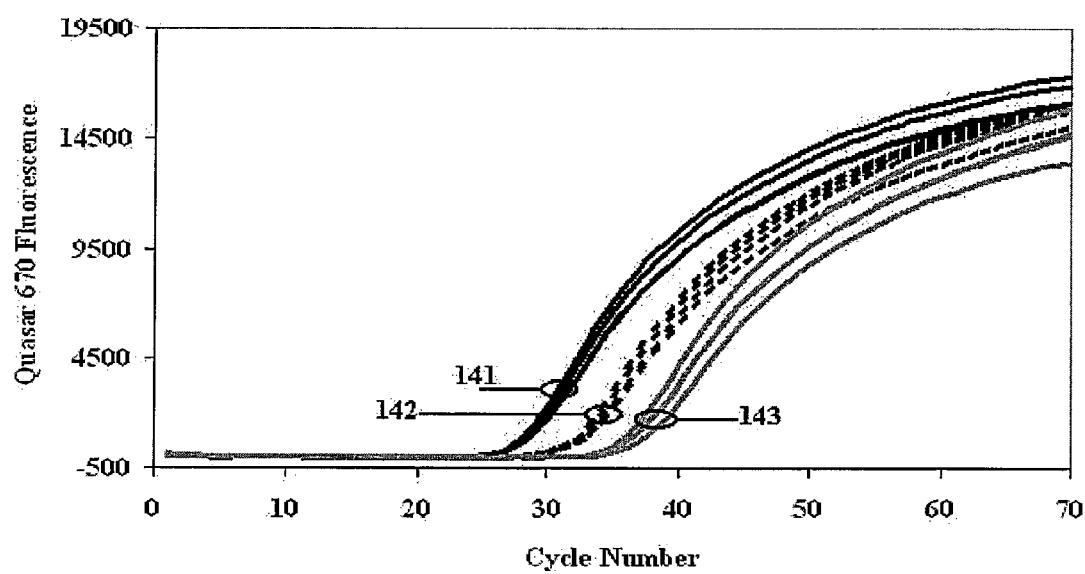
FIG. 14A is a graph of fluorescence from a probe as a function of amplification cycle number for replicates of a LATE-PCR amplification with a low-temperature detection step described in Example 10 utilizing additive EP010 at a concentration of 600 nM, starting with 1000, 100 and 10 copies of target.

The likelihood of Type II mispriming is enhanced by the inclusion of a low-temperature detection step in PCR cycles for real-time detection. Type III mispriming is enhanced by lengthening a LATE-PCR amplification to generate single-stranded product. We have tested a protocol that we refer to as "ColdStop" in which, as a replacement for real-time, low-temperature detection, the amplification reaction is interrupted at one or several intermediate points in order to perform an operation that may include a low-temperature step. Example 10 illustrates a "ColdStop" protocol in which that operation is a melt analysis. The amplification in Example 10 is a 2-step LATE-PCR amplification of 70 cycles using a hybridization probe for fluorescence detection. Additive EP010 was tested at a concentration of 600 nM. For purposes of comparison, an amplification was performed with real-time detection. For real-time detection a low-temperature detection step (60° C.) was added following each annealing/extension step of the amplification cycles. Probe fluorescence as a function of thermal cycles is shown in FIG. 14A, which shows a moderate scatter among replicates for the amplifications starting with 1000, 100, and 10 copies of the target sequence. FIG. 14A also shows the curves for the three amounts of initial target beginning to converge by cycle 70. The inclusion of real-time, low temperature detection increased the chance for Type II mispriming. We repeated the amplification for all three starting copy numbers with no real-time low-temperature detection but with an interruption after 40 cycles to perform a melt beginning at 45° C. Then we resumed amplification to conclusion after 70 cycles, at which time a second melt was performed. The melt curves for the first melt are presented in FIG. 14B. The replicates for the three different starting amounts of target are clearly distinguishable and show little scatter. The melt curves for the second melt are presented in FIG. 14C. By cycle 70 the curves for the three levels of initial target amount have converged, and little scatter is detected.

Figure 14B:
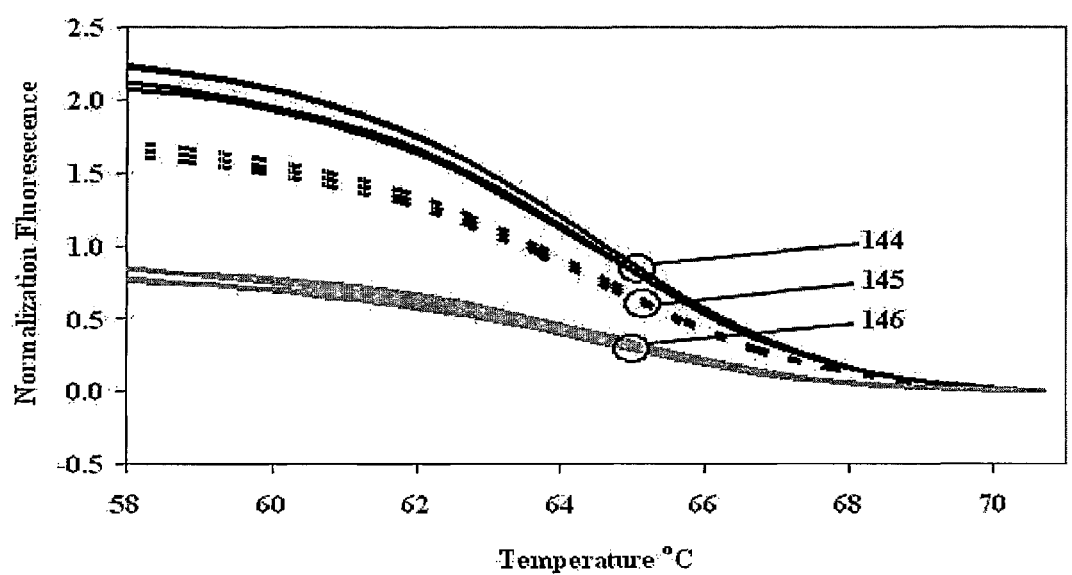
FIG. 14B presents melt curves for probe-amplicon hybrids after 40 cycles of a LATE-PCR ColdStop amplification described in Example 10 utilizing additive EP010 at a concentration of 600 nM. starting with 1000, 100 and 10 copies of target.
Figure 14C:
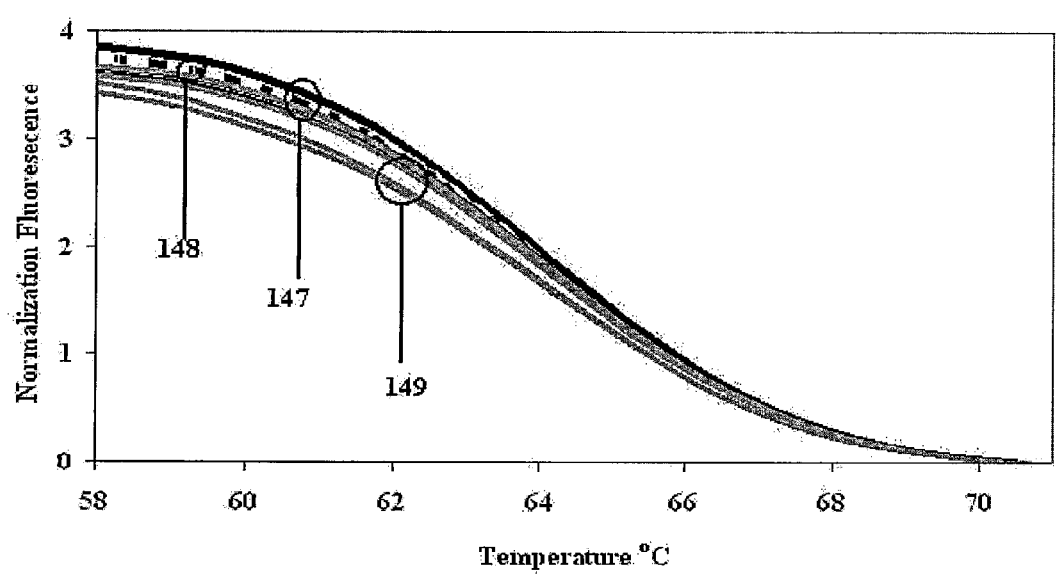
FIG. 14C presents melt curves for probe-amplicon hybrids after 70 cycles of a LATE-PCR ColdStop amplification described in Example 10 utilizing additive EP010 at a concentration of 600 nM. starting with 1000, 100 and 10 copies of target.

To interpret the results shown in FIGS. 14B and 14C, the following are noted. If mispriming takes place due to a low-temperature interruption, single-stranded DNA will be converted into double-stranded DNA, and the amount of single-stranded product will decrease between cycles 40 and 70. That did not happen. If mispriming occurs during the interruption after 40 cycles, scatter among the replicates will increase between cycle 40 and 70. That did not happen. If mispriming occurs during the interruption, the amount of single-stranded product generated from the differing amounts of initial target would fail to equalize after 70 cycles. That did not happen. Comparison of FIG. 14A, FIG. 14B and FIG. 14C indicates that additive EP046 completely suppressed all types of mispriming in this "ColdStop" amplification. The "ColdStop" protocol with a single interruption eliminates any low-temperature step prior to cycle 40 and after cycle 41. This reduces the chances for Type II and Type III mispriming during all but cycle 41. The first melt includes a lengthy time at a temperature below the primer annealing temperature (in this example, about 15 minutes), and so increased the likelihood of mispriming during the melt (which would include one extension of misprimed 3' ends), in exchange for eliminating a low-temperature step in other cycles. That trade-off may help to reduce scatter among replicates. It will be appreciated a "ColdStop" protocol can be used to screen additive compositions and concentrations for their effects on mispriming.

Inhibition of 5' Exonuclease Activity of DNA Polymerase

Additives can be effective to inhibit the 5' exonuclease activity of DNA polymerases that possess that activity, for example Taq DNA polymerase and Tfi (+) DNA polymerase. (This effect is not applicable to DNA polymerases not having that activity, such as the Klenow fragment, which does not possess a 5' exonuclease domain, and Tfi(−) DNA polymerase, which contains a 5' exonuclease domain that is modified to render it inactive.) We developed the assay reported in Example 6 as a primer-independent means to gage the inhibitory effects of additives on the 5' exonuclease activity of DNA polymerases. In that assay, a non-extendable probe that is dual labeled with a fluorophore and a quencher is hybridized to a target without primers being included in the reaction mixture. The reaction mixture is then subjected to thermal oscillation in which the temperature is cycled between 45° C. and 60° C. forty-five times, during which probe fluorescence is detected in real time. Probe cleavage leads to increased fluorescence indicative of 5' exonuclease activity of the polymerase. Several additives were tested in this assay at a concentration of 300 nM and compared to a control assay that included probe but no target. In the control assay no hybrid was formed, and the probe was not cleaved. In an assay containing probe and target but no additive, a large increase in fluorescence resulted. In assays containing probe, target and an additive, fluorescence increase was markedly reduced compared to the assay with target but no additive, showing substantial inhibition of 5' nuclease activity. Additives EP004 and EP001, that have three and four covalently linked Dabcyl groups respectively, completely inhibited primer-independent 5' exonuclease cleavage of the probe. Additive EP008, that has a covalently linked Dabcyl group on each of its 5' nucleotides, also completely inhibited primer-independent 5' exonuclease activity in this assay. In comparison, additive EP009, that has a covalently linked Dabcyl group on each of its 3' nucleotides, only partially inhibited primer-independent 5' exonuclease activity in this assay. The results show that the Dabcyl modifier groups on double-stranded oligonucleotides can enhance inhibition of the 5' exonuclease activity in a position-dependent manner. Dabcyl groups on both 5' ends of the additive are preferred, and three and four Dabcyl groups are preferred over two Dabcyl groups. Addition experiments demonstrated consistent results for Tfi(+) DNA polymerase.

Figure 20:
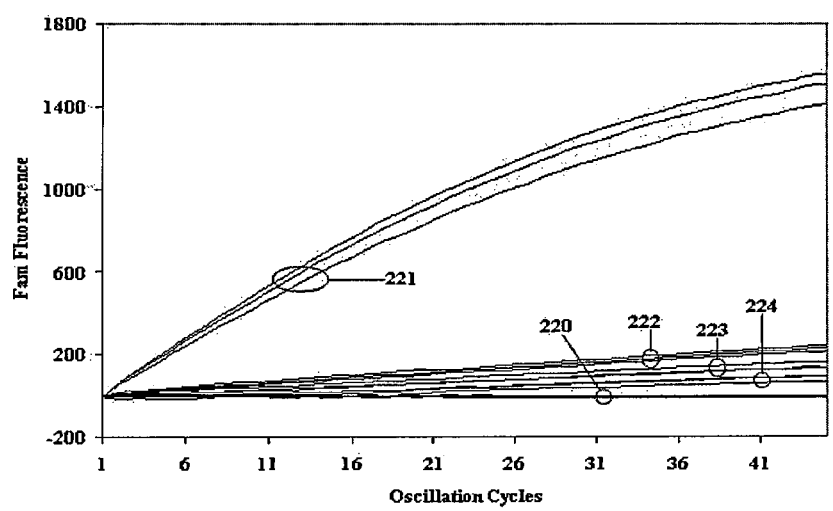
FIG. 20 is a graph of probe fluorescence as a function of the number of temperature oscillation cycles for a primer-independent probe-cleavage assay described in Example 18 utilizing additive SLOG at different concentartions.

As reported in Example 18, we performed the temperature-oscillation assay of Example 6 with various amounts of three additives having a single-stranded region of 22 base pairs and single-stranded overhangs six nucleotides in length. The sequences of the additives are given in Example 16. The additives comprised two strands that were hairpin-forming, as shown in FIG. 18C. Such additives included two, three or four Dabcyl groups as modifiers. As shown in FIG. 20, the additive with two Dabcyl modifiers inhibited primer-independent 5' exonuclease activity of Taq DNA polymerase in a concentration-dependent manner, with concentrations of 200 nM and 400 nM largely inhibiting activity and a concentration of 600 nM nearly completely inhibiting activity. The tested additives with three and four modifiers also inhibited primer-independent 5' exonuclease activity of the polymerase in a concentration-dependent manner but to a somewhat lesser degree than the results shown in FIG. 20.

Figure 11A:
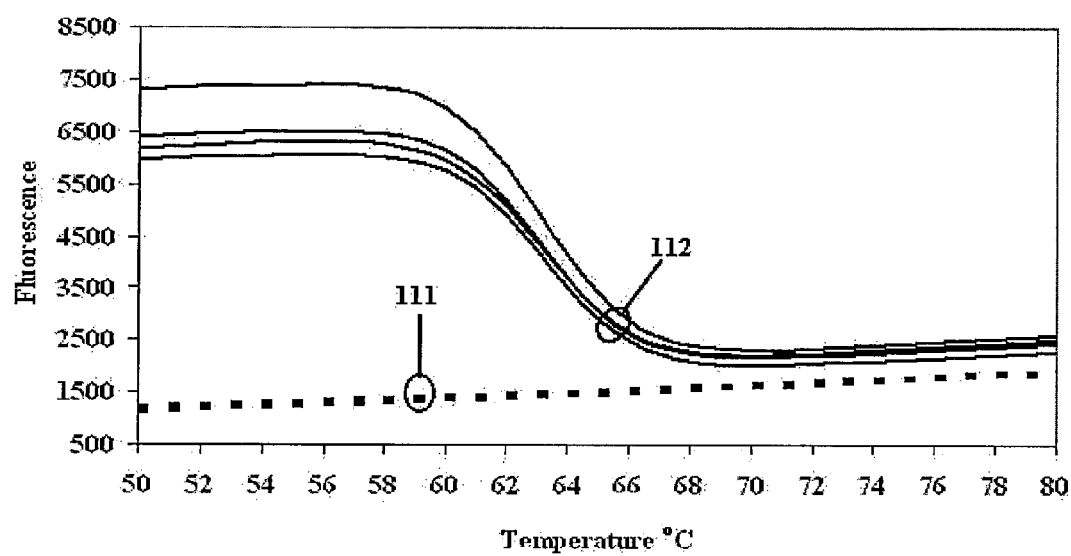
FIG. 11A presents melt curves for probe-amplicon hybrids resulting from replicates of a LATE-PCR amplification described in Example 7 with no additive, and for probe alone.
Figure 11B:
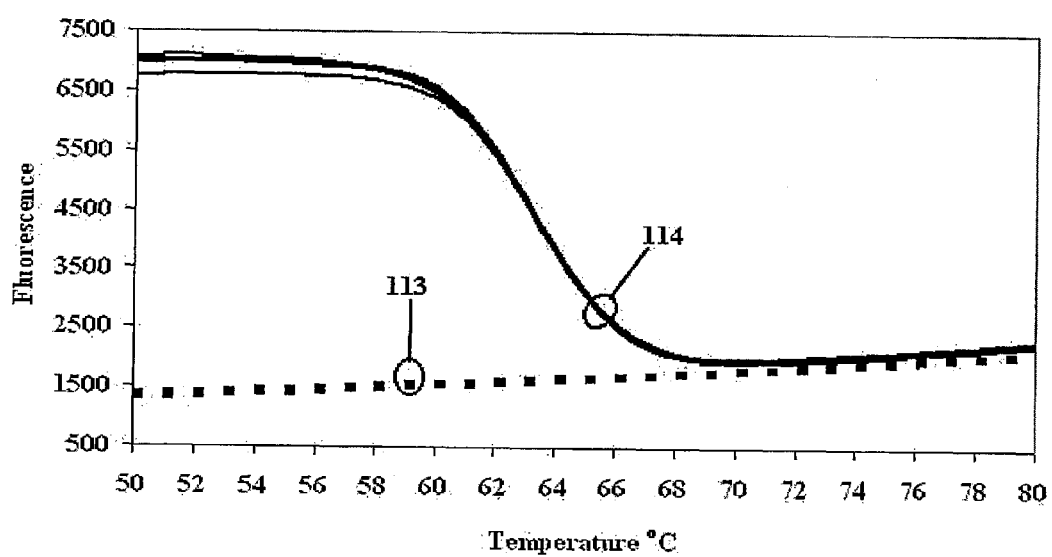
FIG. 11B presents melt curves for probe-amplicon hybrids resulting from replicates of a LATE-PCR amplification described in Example 7 with additive EP013 at 600 nM concentration, and for probe alone.

To gage inhibition of 5' nuclease activity during PCR amplification, we subjected probes and amplicons resulting from the LATE-PCR amplification described in Example 5 to hybridizing conditions followed by melt analysis. A reaction mixture of probe alone was also subjected to melt analysis. The experiment is reported in Example 7, and melt curves are presented in FIGS. 11A and 11B. Comparison of fluorescence from the probe alone and the amplification with no additive in FIG. 11A shows some probe molecules were cleaved: fluorescence from the amplification reaction did not fall to the level of probe fluorescence after melting was completed. FIG. 11B shows probe cleavage due to 5' nuclease activity of the polymerase (in this case Taq DNA polymerase) was inhibited when the amplification reaction mixture included additive EP013 at a concentration of 600 nM: fluorescence from the amplification reaction fell to the level of probe fluorescence after melting was completed.

Additive as a PCR Primer

Example 14 demonstrates an additive in the form of a PCR primer. To convert a typical excess primer for a LATE-PCR amplification into an additive that suppresses Type I mispriming, two things were done: first, a modifying group, in this case a Dabcyl group, was added to the 5' terminus of the primer; and second, a reverse complement strand that was partially complementary to the excess primer and that had both a 5' terminal Dabcyl group and a 3' terminal Dabcyl group was included in the reaction mixture at a concentration of 100, 200 or 300 nM. The Tm of the hybrid formed by the excess primer and the reverse complement strand was reduced relative to the Tm of the hybrid formed by the excess primer and the target sequence by introducing several mismatches into the reverse complement strand (alternatively, the length of the reverse complement strand could have been reduced). The hybrid formed by the excess primer and the reverse complement strand included three modifying groups. Melt analysis of double-stranded amplification products showed that inclusion of the reverse complement sequence in the reaction mixture at a concentration of 200 nM or 300 nM resulted in the expected amplicon with little-to-no other products, and the melt curves showed little scatter among replicates. In contrast, amplification without the reverse complement sequence in the reaction mixture resulted in a mixture of intended amplicon and lower Tm products, and the melt curves showed scatter among replicates.

The foregoing examples are meant to illustrate certain preferred embodiments of additives, reaction mixtures, and methods according and should not be construed as exhaustive or limiting. Numerous variations are possible and would be apparent to one of skill in the art. For example, amplification methods other than PCR may be utilized, and additives may be modified versions of molecules other than double-stranded DNA molecules. Other variations will be apparent to persons skilled in the art.

EXAMPLES

Example 1

Suppression of Type I Mispriming

LATE-PCR assays were performed using a single pair of primers and a single target to generate double-stranded and single-stranded amplicons. Double-stranded products were characterized by melting analysis at the end of amplification. Reaction components other than double-stranded oligonucleotides, and reaction conditions were as follows.

```
Limiting Primer.
                                           (SEQ ID No. 1)
5' CCTGGATTATGCCTGGCACCAT Excess Primer.
                                           (SEQ ID No. 2)
5' CCTTGATGACGCTTCTGTATCTA Target.
                                           (SEQ ID No. 3)
5' CCTGGATTATGCCTGGCACCATTAAAGAAAATATCATCTTTGGT

GTTTCCTATGATGAATATAGATACAGAAGCGTCATCAAAG
```

LATE-PCR amplifications were carried out in 25 ul volume consisting of 1×PCR buffer (Invitrogen, Carlsbad, Calif.), 3 mM $MgCl_2$, 250 nM dNTPs, 50 nM of limiting primer, 1000 nM of excess primer, 0.24×SYBR Green (Invitrogen, Carlsbad, Calif.), 1.25 units of Taq DNA polymerase (Invitrogen, Carlsbad, Calif.) with approximately 1000 genomes of human genomic DNA (Sigma-Aldrich, St. Louis, Mo.). Amplification reactions were run in a triplicate set for each additive, utilizing the additive at concentrations of 50, 100, 300, 600, and 1000 nM, along with a no-additive reaction.

The thermal profile conditions for these reactions were as follows: 95° C./10 s-55° C./30 s-70° C./30 s for 10 cycles followed by 95° C./10 s-50° C./30 s-70° C./30 s for 40 cycles followed by a melt starting at 55° C. with 1° C. increments at 30 s intervals to 97° C.

Reactions were analyzed at the end of 50 cycles by a melt curve analysis using the first derivative of SYBR Green fluorescence (−dF/dT, SYBR) of double-stranded DNA product. In addition, the kinetics of production of double-stranded product (SYBR intensity reading as a function of thermal cycles) was analyzed for certain reactions.

A. 16 mers

Each of the following additives that were 16 nucleotides long was included in the starting reaction mixture (terminal blocker $C_3$ is a three-carbon linker chain):

```
16merA.
                                           (SEQ ID No. 4)
5' CACGACCTCGCCGACC (C3)

(C3) GTGCTGGAGCGGCTGG 5'

16merB.
                                           (SEQ ID No. 5)
5' CACGACCTCGCTGACC (C3)

(C3) GTGCTGGAGCGACTGG 5'
```

EP048: 16 merB with one Dabcyl at 3' end of top strand (SEQ. ID No. 6)
EP049: 16 merB with one Dabcyl at 3' end of bottom strand (SEQ ID No. 7)
EP027: 16 merB with two Dabcyls—one at 3' end of each strand (SEQ ID No. 8)

With no additive, the amplification generated products other than the "correct" product, that is, other than the double-stranded product (amplicon) defined by the primers. The melt curves for the three replicate amplification reactions containing additive 16 merA at 300 nM concentration is shown in FIG. 1, with the intended product identified by the downward-pointing arrow. Circle 11 is the curves for the three replicates. This amplification was judged to be very good, because (1) the correct product was made to the general exclusion of incorrect products, and (2) the three replicates were quite consistent (overlapping curves). The same result was obtained with higher concentrations of 16 merA. At lower concentrations (50 nM, 100 nM), large amounts of incorrect products were found, and the three replicates were inconsistent.

Figure 2:
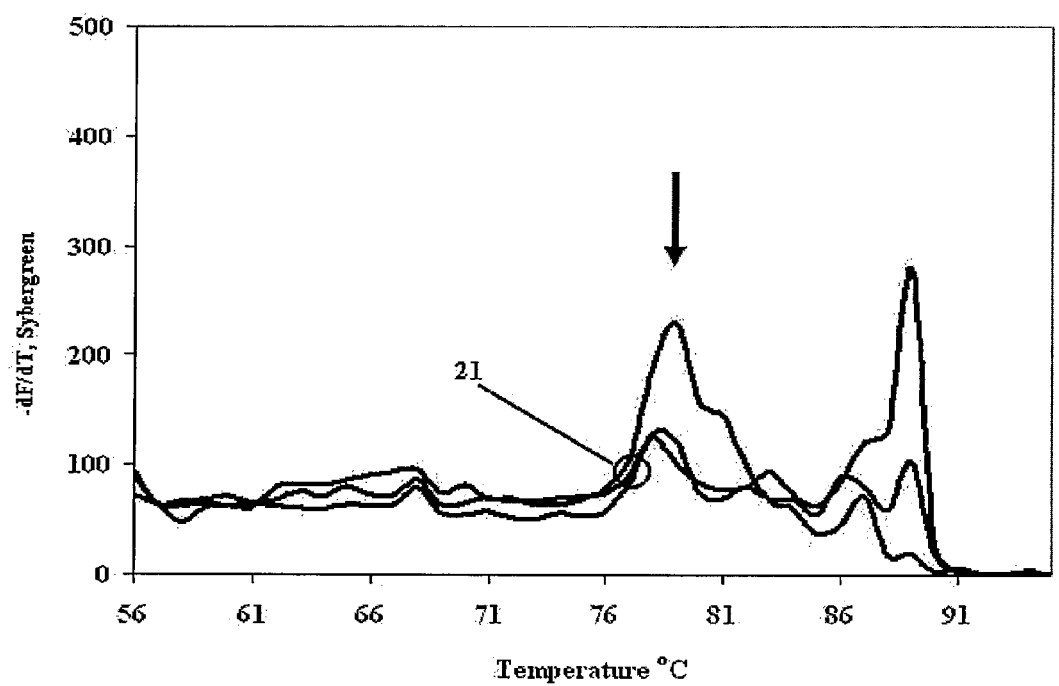
FIG. 2 presents melt curves for replicates of a LATE-PCR amplification described in Example 1 utilizing additive 16 merB at a concentration of 300 nM.

The melt curve for additive 16 merB at 300 nM concentration is shown in FIG. 2. Circle 21 is the curves for the three replicates. This amplification was judged quite unacceptable, because large amounts of incorrect products were found, and the three replicates were inconsistent. At none of the concentrations utilized was the amplification found to generate correct product to the general exclusion of incorrect products, and in none were the replicates highly consistent. The incorrect products differed significantly from the incorrect products obtained with no additive, indicating that additive 16 merB caused mispriming.

Figure 3:
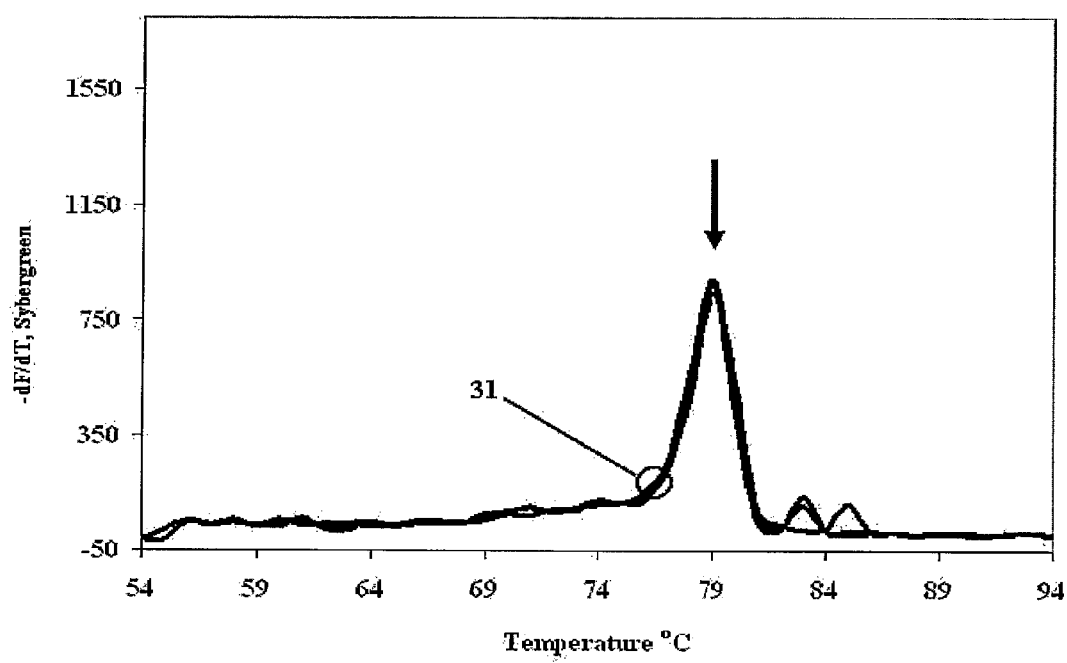
FIG. 3 presents melt curves for replicates of a LATE-PCR amplification described in Example 1 utilizing additive EP049 at a concentration of 600 nM.
Figure 4:
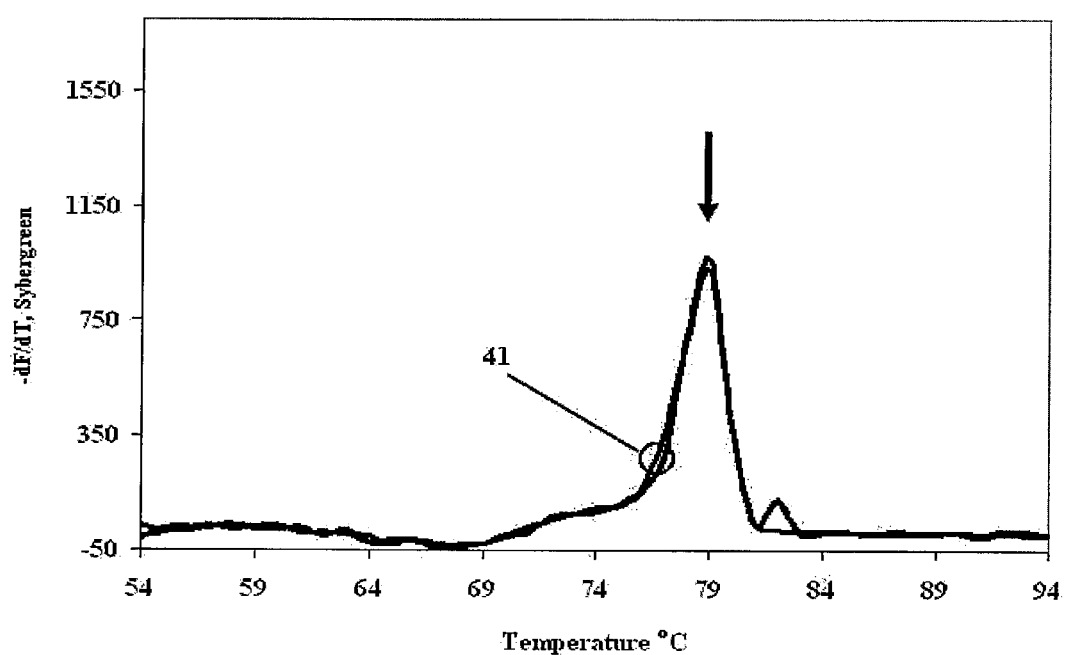
FIG. 4 presents melt curves for replicates of a LATE-PCR amplification described in Example 1 utilizing additive EP027 at a concentration of 100 nM.

The melt curve for additive EP049 at 600 nM concentration is shown in FIG. 3, with the intended product identified by the downward-pointing arrow. Circle 31 is the curves for the three replicates. This amplification was judged to be very good, because (1) the correct product was made to the general exclusion of incorrect products, and (2) the three replicates were quite consistent (overlapping curves). The same result was obtained with higher concentrations, but lower concentrations were not consistent among the replicates and yielded incorrect products. Additive EP048 showed more consistent product at concentrations of 100 and 600 nM, indicating that both strands were capable of mispriming.

The melt curve for additive EP027 at 100 nM concentration is shown in FIG. 4, with the intended product identified by the downward-pointing arrow. Circle 41 is the curves for the three replicates. This amplification was judged to be good rather than very good, because (1) the correct product was made to the general exclusion of incorrect products, and (2) the three replicates were reasonably consistent, with minor variability among the curves. At higher concentration of this additive, the results were judged very good, because the three replicates were quite consistent. At 50 nM, however, significant incorrect products were made, and the replicates were not consistent.

Kinetic analysis of amplifications with EP027 are shown in FIG. 5. Circle 51 is the three replicates at a concentration of 100 nM; circle 52 is the three replicates at a concentration of 300 nM; circle 53 is the three replicates at a concentration of 600 nM; and circle 54 is the three replicates at a concentration of 1000 nM. At 100 nM concentration, there was scatter among the three replicates in the plateau region. The three reactions containing 300 nM had entirely overlapping kinetics and higher efficiency than reactions containing 600 or 1000 nM. Therefore, 300 nM of EP027 was the optimal amount in this assay.

B. Other Additives

Several additives consisting of double-stranded oligonucleotides without added modifiers, and having lengths of 12, 18, 20, 22 and 24 nucleotides were tested in the assay of this example at concentrations of 50, 100, 300, 600 and 1000 nM. As with the 16 mers discussed in Part A, results were inconsistent. Of three different 12 mer's tested, for example, one failed to produce the correct product at all concentrations, one produced the correct product only at 1000 nM concentration, and one produced correct product at concentrations of 600 nM and higher. Of eight longer oligonucleotides tested, half produced significant amounts of incorrect products even at the highest concentrations of 600 and 1000 nM. Only three produced the correct product to the general exclusion of incorrect products at 300 nM concentration, and none did so at lower concentrations. We judged additive 22 merA to be the best in this assay (terminal blocker p is a phosphate):

```
22merA.
                                    (SEQ ID No. 9)
5' GGAGCAAAATAGCAATGAGGTAp pCCTCGTTTTATCGTTACTCCAT 5'
```

Several additives consisting of double-stranded oligonucleotides that included either two or four terminal modifiers and had lengths of 8, 11 and 22 nucleotides were also tested. The modifiers were either Dabcyl or digoxigenin (DIG):

```
Additive EP010.
                                    (SEQ ID No. 10)
5' Dabcyl GGTCAGATGAAAATGATACGTG Dabcyl Dabcyl CCAGTCTACTTTTACTATGCAC Dabcyl 5'

Additive EP018.
                                    (SEQ ID No. 11)
5' GGTCAGATGAAAATGATACGTG Dabcyl Dabcyl CCAGTCTACTTTTACTATGCAC 5'

Additive EP020.
                                    (SEQ ID No. 12)
5' Dabcyl GAAATAAAATAAAAATAAAATA Dabcyl Dabcyl CTTTATTTTATTTTTATTTTAT Dabcyl 5'

Additive EP021.
                                    (SEQ ID No. 13)
5' Dabcyl CAGCCGGC Dabcyl Dabcyl GTCGGCCG Dabcyl 5'

Additive EP022.
                                    (SEQ ID No. 14)
5' Dabcyl CCGCCGGC Dabcyl Dabcyl GGCGGCCG Dabcyl 5'

Additive EP023
                                    (SEQ ID No. 15)
5' Dabcyl GCGTACGCAGG Dabcyl Dabcyl CGCATGCGTCC Dabcyl 5'

Additive EP024.
                                    (SEQ ID No. 16)
5' Dabcyl GCGTACGAAGG Dabcyl Dabcyl CGCATGCTTCC Dabcyl 5'

Additive EP026.
                                    (SEQ ID No. 17)
5' DIG GGAGCAAAATAGCAATGAGGTA DIG

DIG CCTCGTTTTATCGTTACTCCAT DIG 5'

Additive EP028.
                                    (SEQ ID No. 18)
5' Dabcyl TGAGAGATGAAAATGATCGAGT Dabcyl Dabcyl ACTCTCTACTTTTACTAGCTCA Dabcyl 5'

Additive EP029.
                                    (SEQ ID No. 19)
5' GGTCAGATGAAAATGATACGTG DIG

DIG CCAGTCTACTTTTACTATGCAC 5'
```

All of this group of additives produced the correct product to the general exclusion of other products at a concentration equal to or less than 600 nM. All but one (EP021) did so at a concentration of 300 nM or less. Additive EP028 did so at a concentration of 100 nM, and additive EP010 did so at a concentration of 50 nM.

Example 2

Suppression of Type I Mispriming

Unmodified double-stranded oligonucleotide 22 merA, which was judged to be the best unmodified additive in Example 1, and several Dabcyl-modified oligonucleotides were used in an assay for a different target with different primers. Each additive was separately added to a LATE-PCR amplification reaction mixture prior to the start of amplification at concentrations of 100 and 300 nM. Reactions were analyzed at the end of 50 cycles by a melt curve analysis using the first derivative of SYBR Green fluorescence (−dF/dT, Sybr) of double-stranded DNA product. In addition, the kinetics of production of double-stranded product (Sybr intensity reading as a function of thermal cycles) was analyzed for certain reactions. Reaction components other than double-stranded oligonucleotides, and reaction conditions were as follows.

```
Limiting Primer.
                                       (SEQ ID No. 20)
5' AAATTGCGTCATTGTTTCACAGGGCCA Excess Primer.
                                       (SEQ ID No. 21)
5' AATCTGGGTGGTGGTCATAC Target.
                                       (SEQ ID No. 22)
5' AATCTGGGTGGTGGTCATACAGGTCATCACTGTAAAATTCTTTGA

ACTTTTCTGTATATATCTTTGAAAATTTTGGAAAAAAAATGTTGG

AAAACTTAAAAGGCTGTTGCTTTGCTCATATTGGCGGTACATAT

ACAAAAGTGGAAAGGATGAGATTGATTGGCATGGCCCTGTGAA

ACAATGACGCAATTT
```

LATE-PCR amplifications were carried out in 25 ul volume consisting of 1× Invitrogen PCR buffer (Invitrogen, Carlsbad, Calif.), 3 mM MgCl$_2$, 250 nM dNTPs, 50 nM of limiting primer, 1000 nM of excess primer, 0.24×SYBR Green (Invitrogen, Carlsbad, Calif.), 1.25 units of Taq DNA polymerase (Invitrogen, Carlsbad, Calif.) with approximately 1000 genomes of human genomic DNA (Sigma-Aldrich, St. Louis, Mo.). The thermal profile conditions for these reactions were as follows: 25° C. for 30 minutes followed by 95° C./10 s-62° C./20 s-70° C./20 s for 50 cycles followed by a melt starting at 55° C./30 s with 1° C. increments for 42 cycles. (The abbreviation "s", as in 20 s, is "seconds".) All reactions analyzed at the end of 50 cycles using the first derivative of SYBR Green fluorescence (melt curve analysis) of double-stranded DNA product.

The following additives were tested:

```
Additive 22merA.
                                       (SEQ ID No. 9)
5' GGAGCAAAATAGCAATGAGGTAp pCCTCGTTTTATCGTTACTCCAT 5'

Additive EP001.
                                       (SEQ ID NO. 23)
5' Dabcyl GGAGCAAAATAGCAATGAGGTA Dabcyl Dabcyl CCTCGTTTTATCGTTACTCCAT Dabcyl 5'

Additive EP002.
                                       (SEQ ID No. 24)
5' Dabcyl GGAGCAAAATAGCAATGAGGTA Dabcyl pCCTCGTTTTATCGTTACTCCAT Dabcyl 5'

Additive EP003.
                                       (SEQ ID No. 25)
5' GGAGCAAAATAGCAATGAGGTA Dabcyl Dabcyl CCTCGTTTTATCGTTACTCCAT Dabcyl 5'

Additive EP004.
                                       (SEQ ID No. 26)
5' Dabcyl GGAGCAAAATAGCAATGAGGTAp Dabcyl CCTCGTTTTATCGTTACTCCAT Dabcyl 5'

Additive EP005.
                                       (SEQ ID No. 27)
5' Dabcyl GGAGCAAAATAGCAATGAGGTA Dabcyl Dabcyl CCTCGTTTTATCGTTACTCCAT 5'

Additive EP006.
                                       (SEQ ID No. 28)
5' Dabcyl GGAGCAAAATAGCAATGAGGTAp Dabcyl CCTCGTTTTATCGTTACTCCAT 5'

Additive EP007.
                                       (SEQ ID No. 29)
5' GGAGCAAAATAGCAATGAGGTA Dabcyl pCCTCGTTTTATCGTTACTCCAT Dabcyl 5'

Additive EP008.
                                       (SEQ ID No. 30)
5' Dabcyl GGAGCAAAATAGCAATGAGGTAp pCCTCGTTTTATCGTTACTCCAT Dabcyl 5'

Additive EP009.
                                       (SEQ ID No. 31)
5' GGAGCAAAATAGCAATGAGGTA Dabcyl Dabcyl CCTCGTTTTATCGTTACTCCAT 5'

Additive EP020.
                                       (SEQ ID No. 12)
5' Dabcyl GAAATAAAATAAAAATAAAATA Dabcyl Dabcyl CTTTATTTTATTTTTATTTTAT Dabcyl 5'

Additive EP052.
                                       (SEQ ID No. 32)
5' Dabcyl GGAGCAAAATAGCAATGAGGTA Dabcyl pCCTCGTTTTATCGTTACTCCAT 5'

Additive EP053.
                                       (SEQ ID No. 33)
5' GGAGCAAAATAGCAATGAGGTAp Dabcyl CCTCGTTTTATCGTTACTCCAT Dabcyl 5'
```

The double-stranded oligonucleotide 22 merA at 300 nM concentration was judged to be very good, because (1) the correct product was made to the general exclusion of incorrect products, and (2) the three replicates were quite consistent (overlapping curves). That was not the case for 22 merA at 100 nM concentration, however, because one of the replicates did not generally exclude incorrect products. All of the Dabcyl-containing additives were judged to be very good at 300 nM as well. Five of them (EP001, EP002, EP003, EP004 and EP005) were also judged to be very good at 100 nM concentration. FIG. 6 shows the melt curves for the three replicate reactions with additive EP003 and with additive 22 merA at 100 nM concentration. Circle 61 is the three replicates of additive 22 merA. Circle 62 is the three replicates of additive EP003.

Example 3

Type II Mispriming and Polymerase Selectivity

We performed a LATE-PCR assay in which we amplified a target that was complementary to both primers (matched target), and in which we separately amplified a target that was complementary to the excess primer but that contained a single mismatch to the 3' terminal nucleotide of the limiting primer. We detected double-stranded product in real time, that is, during the primer annealing portion of every PCR cycle, by a DNA dye, in this case SYBR Green. Selectivity against a 3' terminal mismatch in the presence of an additive at any concentration is the difference between the threshold cycle ($C_T$) of the signal from amplification of the mismatched target and the $C_T$ of the signal from amplification of the matched target ($\Delta C_T$). Amplification reactions were run in triplicate. The $C_T$ differences are calculated using averages of the three replicates. The effectiveness of an additive for improving selectivity of a DNA polymerase is the $C_T$ difference with the additive minus the $C_T$ difference without any additive. Under the heading "Selectivity" in this and subsequent Examples, we report the improvement in the $C_T$ difference resulting from the use of an additive, in $C_T$ units, that is, as a $\Delta C_T$.

The sequences of the primers and single-stranded targets are as follows:

```
Limiting Primer.
                                    (SEQ ID NO. 34)
5'CGTAAGATTACAATGGCAGGCTCCAGT Excess Primer.
                                    (SEQ ID NO. 35)
5'GCCCAAGTTTTATCGTTCTTCTCA Matched Target (A).
                                    (SEQ ID No. 36)
5' CGTAAGATTACAATGGCAGGCTCCAGAAGGTTCTAA

GTGCCATGATACAAGCTTCCCAATTACTAAGTATGC

TGAGAA GAACGATAAAACTTGGG

Mismatched Target (T).
                                    (SEQ ID No. 37)
5'CGTAAGATTACAATGGCAGGCTCCAGTAGGTTCTA

AGTGCCATGATACAAGCTTCCCAATTACTAAGTATGCTG

AGAAGAACGATAAAACTTGGGCAA
```

The underlined and bolded nucleotide is the nucleotide whose complement in the excess strand will either match or mismatch the 3' terminal nucleotide of the limiting primer.

The LATE-PCR amplifications were carried out in triplicate (three replicate assays) in 25 ul volume consisting of 1× Invitrogen PCR buffer (Invitrogen, Carlsbad, Calif.), 3 mM $MgCl_2$, 250 nM dNTPs, 50 nM of limiting primer, 1000 nM of excess primer, 0.24×SYBR Green (Invitrogen, Carlsbad, Calif.), 1.25 units of Platinum Taq DNA polymerase (Invitrogen, Carlsbad, Calif.) with approximately 1000 single-stranded target A (matched) or T (mismatched). The thermal profile conditions for these reactions were: 95° C. for 3 minutes followed by 95° C./5 s-62° C./20 s-72° C./30 s for 60 cycles. For this and other assays containing two targets, we run a control amplifications using the excess primer, which is perfectly complementary to both targets, and a control limiting primer that is also perfectly complementary to both targets, to ensure that the starting copy numbers of both targets are the same, in which case the $C_T$'s for both targets is the same. (If the control amplifications reveal that the starting copy numbers are not the same, one has two choices: either reformulate or, if the $C_T$ difference is slight—as was the case in all Examples reported here, correct the observed $C_T$ values to adjust for the difference.)

Where Tm is reported, that is the calculated melting temperature of the double-stranded additive without modifiers. Tm's of double-stranded additives presented in this specification were calculated according to Markhan and Zuker (2005) DINAMELT web server for nucleic acid melting prediction, *Nucleic Acids Res.* 33:W577-W581, and Markham and Zuker (2008) UNAFOLD: software for nucleic acid folding and hybridization. In Keith, J. M., ed., BIOINFORMATICS, vol. II, *Structure, Functions and Applications*, No. 453 in *Methods in Molecular Biology*, Ch. 1, pages 3-31 (Humana Press, Totowa, N.J. ISBN 978-1-60327-428-9.

A. No Additive

This assay was run with no additive. SYBR Green signals were detected in real time, that is, during the primer annealing portion of all PCR cycles. The fluorescence intensity readings as a function of amplification cycle number show that the enzyme has a modest inherent selectivity for the matched target. When additives were tested in this assay, a no-additive control was also included, and the $C_T$ difference between matched and mismatched target sequences for the no-additive control was subtracted from the $C_T$ difference between matched and mismatched target sequences for the additive to arrive at the selectivity improvement numbers ($\Delta C_T$) presented.

B. Double-Stranded Additive with No Modifier.

The following 22-nucleotide long double-stranded oligonucleotide, denominated "22 merA", in which the 3' terminus of each strand was capped with a phosphate (p) to prevent extension by the DNA polymerase, was utilized as the additive at three different concentrations:

```
22mer A.
                                    (SEQ ID NO. 9)
5' GGAGCAAAATAGCAATGAGGTAp pCCTCGTTTTATCGTTACTCCAT 5'
```

The results for selectivity ($C_T$ for mismatched target minus $C_T$ for matched target) are shown in Table 1.

TABLE 1

| Additive | Length (NT's) | Tm, ° C. | Concentration, nM | Selectivity, $\Delta C_T$ |
|---|---|---|---|---|
| 22merA | 22 | 63.1 | 100 | 0.1 |
|  |  |  | 200 | 1.2 |
|  |  |  | 300 | 1.8 |

C. Double-Stranded Additives with Two Dabcyl Modifiers.

The double-stranded oligonucleotide 16 mer B described in Example 1 (SEQ ID No. 5) was modified with two Dabcyls by placing a Dabcyl at the 5' end of the top strand and a Dabcyl at the 3' end of the bottom strand (additive EP050, SEQ ID No. 38); and by placing a Dabcyl at the 3' end of the top strand and a Dabcyl at the 5' end of the bottom strand (additive EP051, SEQ ID No. 39). The double-stranded oligonucleotide 22 merA described in part B above (SEQ ID No. 9) was modified by placing a Dabcyl on the 5' end of the top strand and a Dabcyl on the 3' end of the bottom strand (additive EP006, SEQ ID No. 28); by placing a Dabcyl on the 3' end of the top strand and a Dabcyl on the 5' end of the bottom strand (additive EP007, SEQ ID No. 29); by placing a Dabcyl on the 5' end of each strand (additive EP008, SEQ ID No. 30); by placing a Dabcyl on the 3' end of each strand (additive EP009, SEQ ID No. 31); by placing a Dabcyl on each end of the top strand (additive EP052, SEQ ID No. 32); and by placing a Dabcyl on each end of the bottom strand (additive EP053, SEQ ID No. 33). Sequences of these additives are given below, and results for selectivity are presented in Table 2.

```
Aditive EP050.
                                          (SEQ ID No. 38)
5' Dabcyl CACGACCTCGCTGACC (C3)

Dabcyl GTGCTGGAGCGACTGG 5'

Additive EP051.
                                          (SEQ ID No. 39)
5' CACGACCTCGCTGACC Dabcyl pGTGCTGGAGCGACTGG Dabcyl 5'

Additive EP006.
                                          (SEQ ID No. 28)
5' Dabcyl GGAGCAAAATAGCAATGAGGTAp Dabcyl CCTCGTTTTATCGTTACTCCAT 5'

Additive EP007.
                                          (SEQ ID No. 29)
5' GGAGCAAAATAGCAATGAGGTA Dabcyl pCCTCGTTTTATCGTTACTCCAT Dabcyl 5'

Additive EP008.
                                          (SEQ ID No. 30)
5' Dabcyl GGAGCAAAATAGCAATGAGGTAp pCCTCGTTTTATCGTTACTCCAT Dabcyl 5'

Additive EP009.
                                          (SEQ ID No. 31)
5' GGAGCAAAATAGCAATGAGGTA Dabcyl Dabcyl CCTCGTTTTATCGTTACTCCAT 5'

Additive EP052.
                                          (SEQ ID No. 32)
5' Dabcyl GGAGCAAAATAGCAATGAGGTA Dabcyl pCCTCGTTTTATCGTTACTCCAT 5'

Additive EP053.
                                          (SEQ ID No. 33)
5' GGAGCAAAATAGCAATGAGGTAp Dabcyl CCTCGTTTTATCGTTACTCCAT Dabcyl
```

TABLE 2

| Additive | Length (NT's) | Tm, ° C. | Concentration, nM | Selectivity, Δ $C_T$ |
|---|---|---|---|---|
| EP050 | 16 | 62.8 | 200 | 1.6 |
|  |  |  | 300 | 2.9 |
|  |  |  | 400 | 5.5 |

TABLE 2-continued

| Additive | Length (NT's) | Tm, ° C. | Concentration, nM | Selectivity, Δ $C_T$ |
|---|---|---|---|---|
| EP051 | 16 | 62.8 | 200 | 1.1 |
|  |  |  | 300 | 2.7 |
|  |  |  | 400 | 1.8 |
| EP006 | 22 | 63.1 | 100 | 3.5 |
|  |  |  | 300 | 8.3 |
|  |  |  | 600 | 12.0 |
| EP007 | 22 | 63.1 | 100 | 3.5 |
|  |  |  | 300 | 7.3 |
|  |  |  | 600 | 11.5 |
| EP008 | 22 | 63.1 | 100 | 1.7 |
|  |  |  | 300 | 5.8 |
|  |  |  | 600 | 9.7 |

D. Additives with Three Dabcyl Modifiers.

The double-stranded oligonucleotide 22 merA described in part B above (SEQ ID No. 9) was modified by placing a Dabcyl on each end of the top strand and on the 5' end of the bottom strand (additive EP002, SEQ ID No. 24); by placing a Dabcyl on the 3' end of the top strand and on each end of the bottom strand (additive EP003, SEQ ID No. 25); by placing a Dabcyl on the 5' end of the top strand and on each end of the bottom strand (additive EP004, SEQ ID No. 26); and by placing a Dabcyl on each end of the top strand and on the 3' end of the bottom strand (additive EP005, SEQ ID No. 27). Sequences of the additives are given below and results are presented in Table 3.

```
Additive EP002.
                                          (SEQ ID No. 24)
5' Dabcyl GGAGCAAAATAGCAATGAGGTA Dabcyl pCCTCGTTTTATCGTTACTCCAT Dabcyl 5'

Additive EP003.
                                          (SEQ ID No. 25)
5' GGAGCAAAATAGCAATGAGGTA Dabcyl Dabcyl CCTCGTTTTATCGTTACTCCAT Dabcyl 5'

Additive EP004.
                                          (SEQ ID No. 26)
5' Dabcyl GGAGCAAAATAGCAATGAGGTAp Dabcyl CCTCGTTTTATCGTTACTCCAT Dabcyl 5'

Additive EP005.
                                          (SEQ ID No. 27)
5' Dabcyl GGAGCAAAATAGCAATGAGGTA Dabcyl Dabcyl CCTCGTTTTATCGTTACTCCAT 5'
```

TABLE 3

| Additive | Length (NT's) | Tm, ° C. | Concentration, nM | Selectivity, Δ $C_T$ |
|---|---|---|---|---|
| EP002 | 22 | 63.1 | 100 | 4.2 |
|  |  |  | 200 | 7.1 |
|  |  |  | 300 | 9.2 |
| EP003 | 22 | 63.1 | 100 | 2.1 |
|  |  |  | 200 | 5.6 |
|  |  |  | 300 | 8.2 |
| EP004 | 22 | 63.1 | 100 | 5.0 |
|  |  |  | 200 | 6.6 |
|  |  |  | 300 | 11.9 |
| EP005 | 22 | 63.1 | 100 | 5.9 |
|  |  |  | 200 | 9.3 |
|  |  |  | 300 | 7.8 |

E. Additives with Four Dabcyl Modifiers.

Several double-stranded oligonucleotides were modified with four terminal Dabcyl modifiers:

```
Additive EP022.
                                      (SEQ ID No. 153)
5' Dabcyl CGCCGCGC Dabcyl Dabcyl GCGGCGCG Dabcyl 5'

Additive EP020.
                                       (SEQ ID No. 12)
5' Dabcyl GAAATAAAATAAAAATAAAATA Dabcyl Dabcyl CTTTATTTTATTTTTATTTTAT Dabcyl 5'

Additive EP001.
                                       (SEQ ID NO. 23)
5' Dabcyl GGAGCAAAATAGCAATGAGGTA Dabcyl Dabcyl CCTCGTTTTATCGTTACTCCAT Dabcyl 5'

Additive EP028.
                                (SEQ ID Nos 154 and 155)
5' Dabcyl TGAGAGATGAAAATCATCGAGT Dabcyl Dabcyl ACTCTCACTTTTTACTAGCTCA Dabcyl 5'
```

Results are shown in Table 4.

TABLE 4

| Additive | Length (NT's) | Tm, ° C. | Concentration, nM | Selectivity, Δ $C_T$ |
|---|---|---|---|---|
| EP0022 | 8 | 42.8 | 600 | 1.2 |
| EP0020 | 22 | 47.7 | 600 | 0.9 |
| EP001 | 22 | 63.1 | 100 | 7.1 |
|  |  |  | 200 | 9.5 |
| EP028 | 22 | 60.6 | 300 | 10.0 |

F. Additives with Different Modifiers.

Several double-stranded oligonucleotides were modified with modifiers other than Dabcyl. Three modifiers, digoxigenin (DIG), coumarin (CMN), QSY 21 (QSY), were shown to be useful in additives, and one, fluorescein (FAM), was not. Sequences of the oligonucleotides were as follows:

```
Additive EP026.
                                       (SEQ ID No. 17)
5' DIG GGAGCAAAATAGCAATGAGGTA DIG

DIG CCTCGTTTTATCGTTACTCCAT DIG 5'

Additive EP029.
                                       (SEQ ID No. 40)
5' GGTCAGATGAAAATGATACGTG DIG

DIG CCAGTCTACTTTTACTATGCAC 5'

Additive EP031.
                                       (SEQ ID No. 41)
5' CMN GGTCAGATGAAAATGATACGTG CMN

CMN CCAGTCTACTTTTACTATGCAC CMN 5'

Additive EP033.
                                       (SEQ ID No. 42)
5' QSY GGTCAGATGAAAATGATACGTG QSY

QSY CCAGTCTACTTTTACTATGCAC QSY 5'

Additive F032.
                                       (SEQ ID No. 43)
5' FAM GGTCAGATGAAAATGATACGTG FAM

FAM CCAGTCTACTTTTACTATGCAC FAM 5'
```

Results are shown in Table 5.

TABLE 5

| Additive | Length (NT's) | Tm, ° C. | Concentration, nM | Selectivity, Δ $C_T$ |
|---|---|---|---|---|
| EP026 | 22 | 63.1 | 300 | 3.8 |
| EP029 | 22 | 63.1 | 300 | 0.9 |
| EP031 | 22 | 63.1 | 200 | 3.2 |
| EP033 | 22 | 63.1 | 200 | 3.4 |
| F032 | 22 | 63.1 | 200 | 0.9 |

Example 4

Type II Mispriming and Polymerase Selectivity with Additive Mixtures

Combinations of two additives can be added to the reaction mixture as four strands, that is, as a mixture of two different double-stranded oligonucleotides. Alternatively, two additives can share a common strand and, thus, be added to the reaction mixture as three strands. This example reports results obtained in the assay reported in Example 3 using three-strand versions of mixtures, including a control mixture having no modifiers. For two additives that share a common strand, we write the common strand in the middle, the strand whose hybrid with the middle strand has the higher melting temperature on top, and the strand whose hybrid with the middle strand has the lower melting temperature on the bottom. We write the strand concentrations, in nM, as top/middle/bottom. We write the Tm's of the two hybrids (° C.) as upper/lower. Melting temperatures were adjusted either by shortening the bottom strand or introducing mismatches into the bottom strand (mismatched nucleotides are underlined). The additives tested were:

```
Additive 041.
                                       (SEQ ID No. 44)
pCCTCGTCTGATCGTGACTCCAT 5'

5' GGAGCAGACTAGCACTGAGGTAp pTCTGATCGTGACTCCAT 5'

Additive EP041.
                                       (SEQ ID No. 45)
Dabcyl CCTCGTCTGATCGTGACTCCAT Dabcyl 5'

5' GGAGCAGACTAGCACTGAGGTA Dabcyl

Dabcyl TCTGATCGTGACTCCAT Dabcyl 5'

Additive 042.
                                (SEQ ID Nos 46 and 156)
pCCTCGTCTGATCGTGACTCCAT 5'

5' GGAGCAGACTAGCACTGAGGTAp pCCTGGTCTGATTGTGACTCCAT 5'

Additive EP042.
                                (SEQ ID Nos 47 and 157)
Dabcyl CCTCGTCTGATCGTGACTCCAT Dabcyl 5'

5' GGAGCAGACTAGCACTGAGGTA Dabcyl

Dabcyl CCTGGTCTGATTGTGACTCCAT Dabcyl 5'
```

-continued
Additive EP043.
(SEQ ID No. 48)
5' GGAGCAGACTAGCACTGAGGTA Dabcyl

Dabcyl CCTCGTCTGATCGTGACTCCAT Dabcyl 5'

5' Dabcyl AGACTAGCACTGAGGTA Dabcyl

Additive EP045.
(SEQ ID No. 49)
5' Dabcyl GGAGCAGACTAGCACTGAGGTA Dabcyl

Dabcyl CCTCGTCTGATCGTGACTCCAT Dabcyl 5'

5' Dabcyl AGACTAGCACTGAGGTA Dabcyl

Results are shown in Table 6, along with the strand concentrations and the Tm's of the unmodified hybrid of the upper two strands and the lower two strands. Numbers for improvement in selectivity over a no-additive control ($\Delta C_T$) were calculated as described in Example 3.

TABLE 6

| Additive | Tm(Upper/Lower, (° C.) | Concentrations, nM | Selectivity, $\Delta C_T$ |
|---|---|---|---|
| 041 | 67.4/59.0 | Top 75<br>Mid. 400<br>Bot. 325 | 1.7 |
| EP041 | 67.4/59.0 | Top 75<br>Mid. 400<br>Bot. 325 | 4.8 |
| 042 | 67.4/57.4 | Top 75<br>Mid. 400<br>Bot. 325 | 1.9 |
| EP042 | 67.4/57.4 | Top 75<br>Mid. 400<br>Bot. 325 | 6.8 |
| EP043 | 67.4/59.1 | Top 25<br>Mid. 600<br>Bot. 575 | 2.4 |
|  |  | Top 50<br>Mid. 600<br>Bot. 550 | 2.9 |
|  |  | Top 75<br>Mid. 600<br>Bot. 525 | 2.2 |
|  |  | Top 100<br>Mid. 600<br>Bot. 500 | 3.3 |
| EP045 | 67.4/59.1 | Top 25<br>Mid. 600<br>Bot. 575 | 5.0 |
|  |  | Top 50<br>Mid. 600<br>Bot. 550 | 6.9 |
|  |  | Top 75<br>Mid. 600<br>Bot. 525 | 7.7 |
|  |  | Top 100<br>Mid. 600<br>Bot. 500 | 10.8 |

Figure 7A:
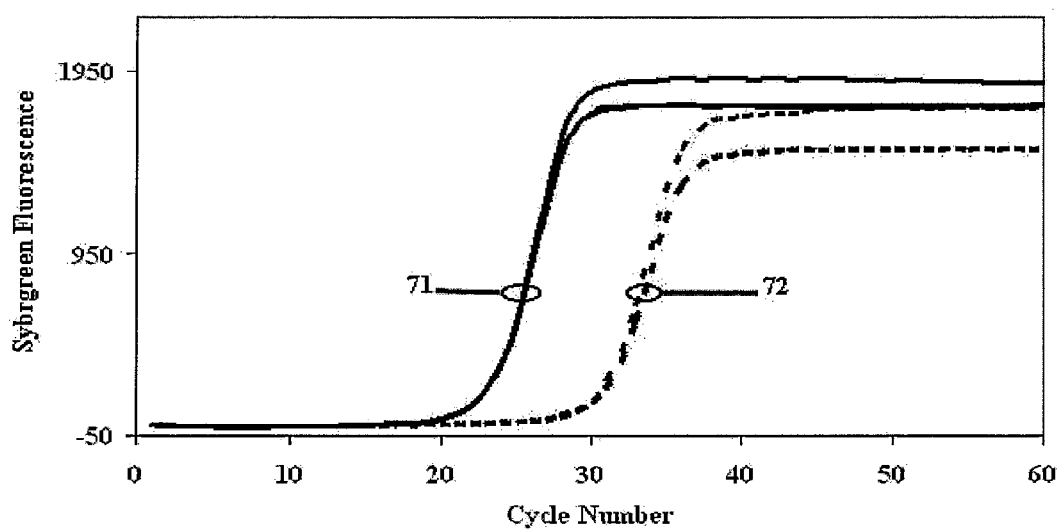
FIG. 7A is a graph of SYBR Green fluorescence as a function of amplification cycle number for replicates of a LATE-PCR amplification described in Example 4 utilizing three-strand additive mixture EP043 at a total concentration of 600 nM and strand concentrations of 25/600/575 nM.
Figure 7B:
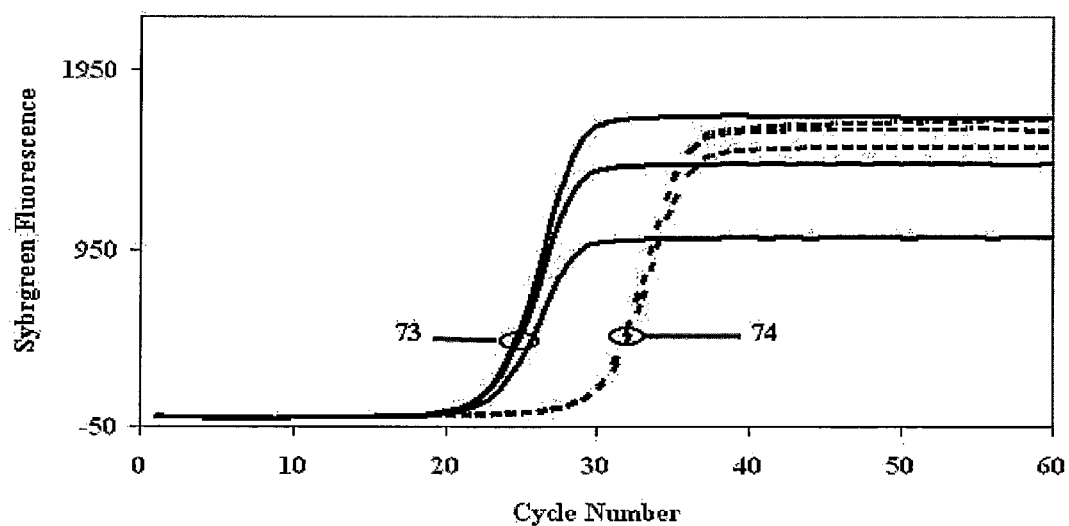
FIG. 7B is a graph of SYBR Green fluorescence as a function of amplification cycle number for replicates of a LATE-PCR amplification described in Example 4 utilizing three-strand additive mixture EP043 at a total concentration of 600 nM and strand concentrations of 50/600/550 nM.
Figure 7C:
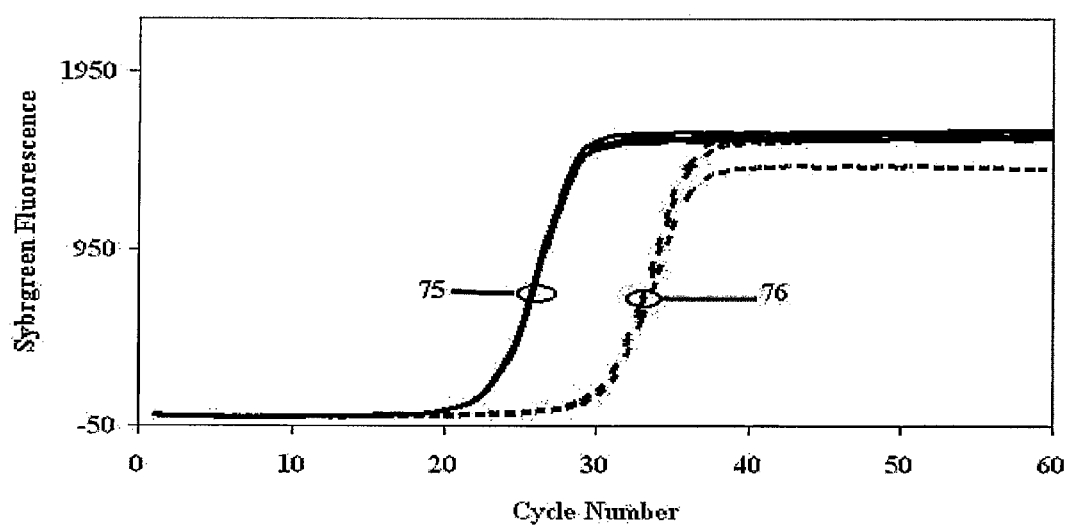
FIG. 7C is a graph of SYBR Green fluorescence as a function of amplification cycle number for replicates of a LATE-PCR amplification described in Example 4 utilizing three-strand additive mixture EP043 at a total concentration of 600 nM and strand concentrations of 75/600/525 nM.
Figure 7D:
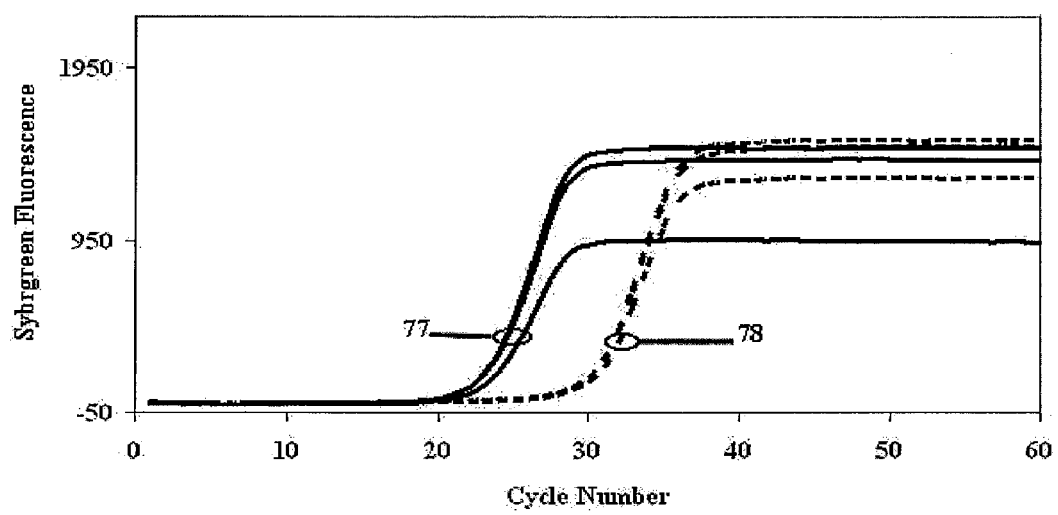
FIG. 7D is a graph of SYBR Green fluorescence as a function of amplification cycle number for replicates of a LATE-PCR amplification described in Example 4 utilizing three-strand additive mixture EP043 at a total concentration of 600 nM and strand concentrations of 100/600/500 nM.

Kinetic analysis of amplification reactions with additives EP043 and EP045 are shown in FIGS. 7A-7D and FIGS. 8A-8D, respectively. These figures present fluorescence intensity readings from SYBR Green dye as a function of LATE-PCR cycle number for different concentrations of additive. FIG. 7A presents the results with additive EP043 having strand concentrations (upper/middle/lower strands) of 25/600/575 nM. In FIG. 7A, circle 71 is the three replicates for the matched target, and circle 72 is the three replicates for the mismatched target. FIG. 7B presents the results with additive EP043 having strand concentrations (upper/middle/lower strands) of 50/600/550 nM. In FIG. 7B, circle 73 is the three replicates for the matched target, and circle 74 is the three replicates for the mismatched target. FIG. 7C presents the results with additive EP043 having strand concentrations (upper/middle/lower strands) of 75/600/525 nM. In FIG. 7C, circle 75 is the three replicates for the matched target, and circle 76 is the three replicates for the mismatched target. FIG. 7D presents the results with additive EP043 having strand concentrations (upper/middle/lower strands) of 100/600/500 nM. In FIG. 7D, circle 77 is the three replicates for the matched target, and circle 78 is the three replicates for the mismatched target.

Figure 8A:
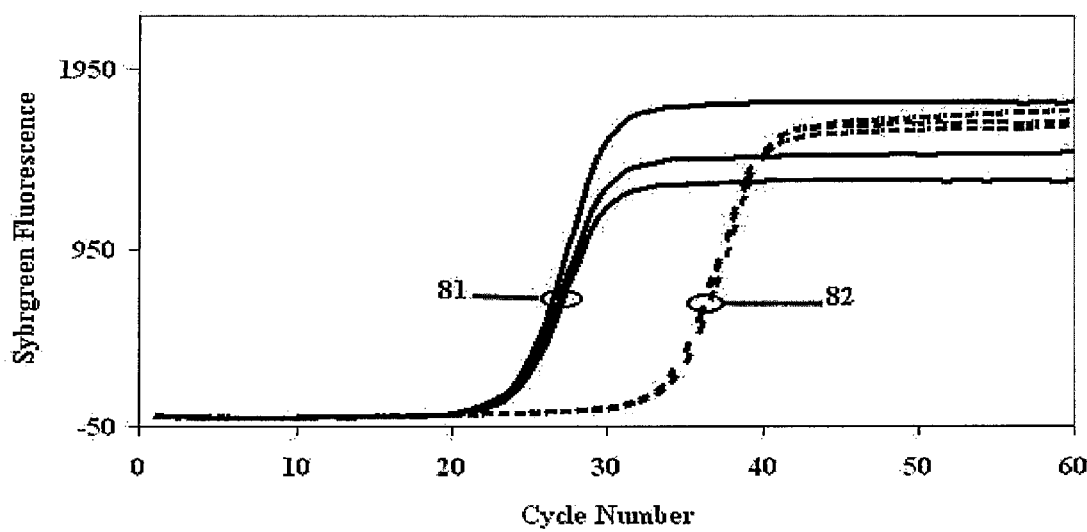
FIG. 8A is a graph of SYBR Green fluorescence as a function of amplification cycle number for replicates of a LATE-PCR amplification described in Example 4 utilizing three-strand additive mixture EP045 at a total concentration of 600 nM and strand concentrations of 25/600/575 nM.
Figure 8B:
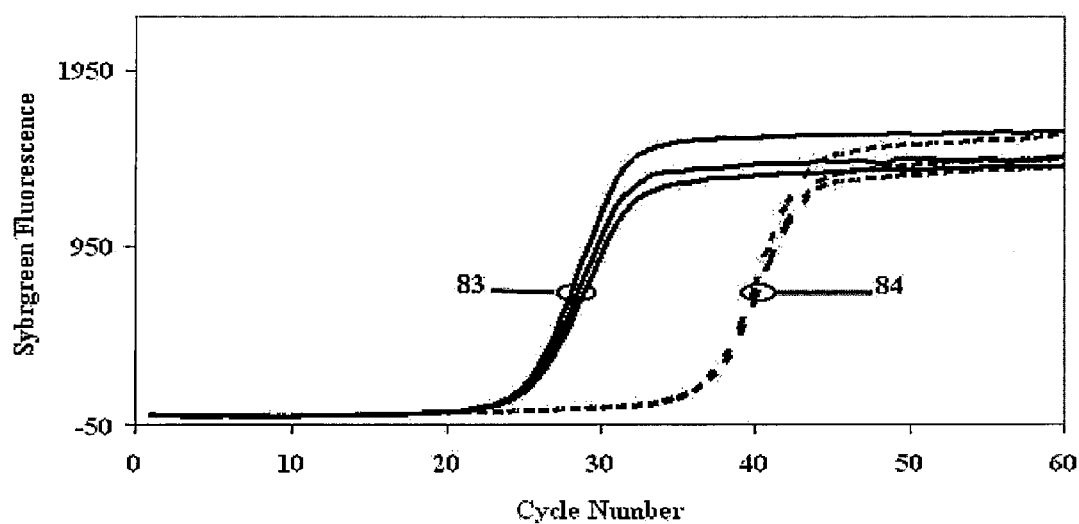
FIG. 8B is a graph of SYBR Green fluorescence as a function of amplification cycle number for replicates of a LATE-PCR amplification described in Example 4 utilizing three-strand additive mixture EP045 at a total concentration of 600 nM and strand concentrations of 50/600/550 nM.
Figure 8C:
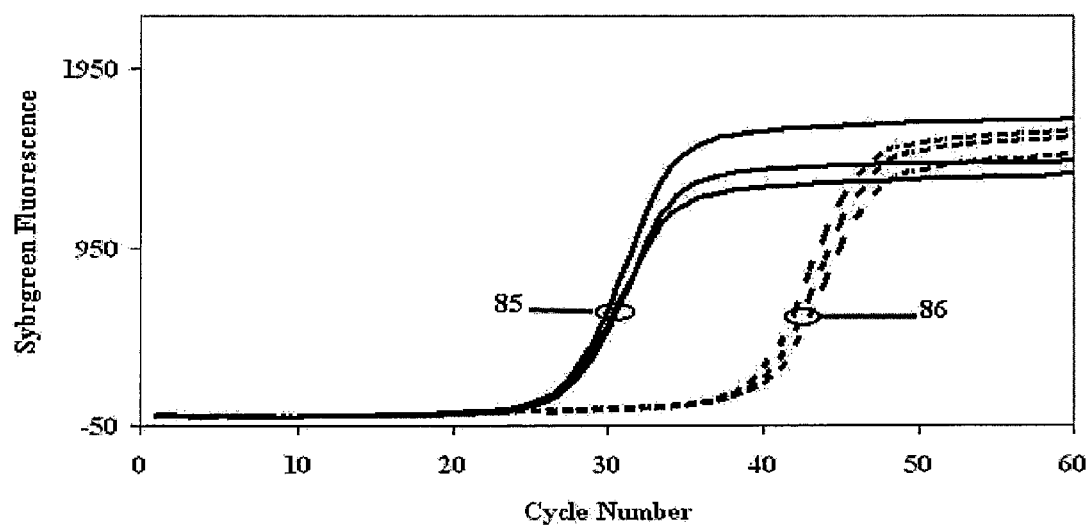
FIG. 8C is a graph of SYBR Green fluorescence as a function of amplification cycle number for replicates of a LATE-PCR amplification described in Example 4 utilizing three-strand additive mixture EP045 at a total concentration of 600 nM and strand concentrations of 75/600/525 nM.
Figure 8D:
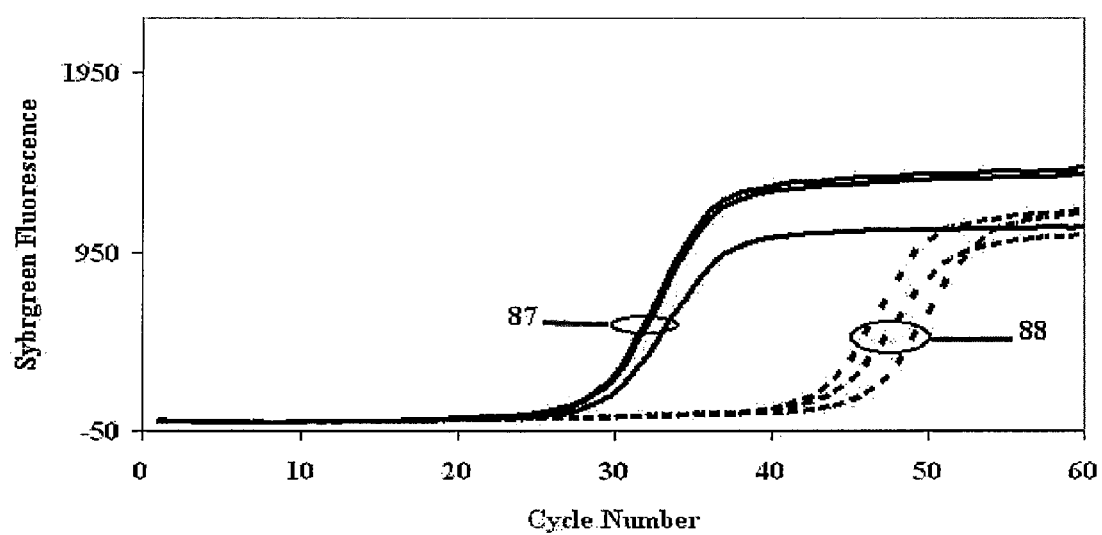
FIG. 8D is a graph of SYBR Green fluorescence as a function of amplification cycle number for replicates of a LATE-PCR amplification described in Example 4 utilizing three-strand additive mixture EP046 at a total concentration of 600 nM and strand concentrations of 100/600/500 nM.

FIG. 8A presents the results with additive EP045 having strand concentrations (upper/middle/lower strands) of 25/600/575 nM. In FIG. 8A, circle 81 is the three replicates for the matched target, and circle 82 is the three replicates for the mismatched target. FIG. 8B presents the results with additive EP045 having strand concentrations (upper/middle/lower strands) of 50/600/550 nM. In FIG. 8B, circle 83 is the three replicates for the matched target, and circle 84 is the three replicates for the mismatched target. FIG. 8C presents the results with additive EP045 having strand concentrations (upper/middle/lower strands) of 75/600/525 nM. In FIG. 8C, circle 85 is the three replicates for the matched target, and circle 86 is the three replicates for the mismatched target. FIG. 8D presents the results with additive EP045 having strand concentrations (upper/middle/lower strands) of 100/600/500 nM. In FIG. 8D, circle 87 is the three replicates for the matched target, and circle 88 is the three replicates for the mismatched target.

Example 5

Suppression of Type I and Type III Mispriming in a Duplex Reaction

A duplex LATE-PCR reaction was run in triplicate with two DNA targets, a primer pair for each target, and a molecular beacon hybridization probe for each target. Each reaction mixture contained the following primers and probes.

For First Target Sequence:

Excess primer.
(SEQ ID No. 50)
5' TGTCATCTTCTGTCCCTTCCCAGAAA

Limiting primer.
(SEQ ID No. 51)
5' ACTGTCCCAGAATGCAAGAAGCCCAGACG

Probe for First Amplicon.
(SEQ ID No. 52)
5' BHQ-1 CCGTAGCTGCCCTGG' Cal Red 610

For Second Target Sequence:

Excess primer.
(SEQ ID No. 53)
5' GCACAGTTACAGTATTCCAGCAGACTCA

Limiting primer.
(SEQ ID No. 54)
5' TCAGTGGTGGCAGTGGTAGTGGTGGC

Probe for Second Amplicon.
(SEQ ID No. 55)
5' BHQ-2 TCAGTGGTGGCAGTGGTAGA Quasar 670

LATE-PCR reaction mixtures included 1× Platinum Taq buffer (Invitrogen, Carlsbad, Calif.), 3 mM MgCl2, 0.25 nM dNTPs, 50 nM each limiting primer, 1000 nM each excess primer, and 500 nM each detection probe, 1.25 units Platinum Taq polymerase (Invitrogen, Carlsbad, Calif.) and 1000 genomes equivalents of human DNA in a volume of 25 ul. Different reaction mixtures contained no additive, additive EP020 at 400 nM concentration, or additive EP013 at 300 nM concentration.

The LATE-PCR amplification reaction thermal profile conditions were 20 cycles of 95° C./10 s, annealing at the temperature specified below for 10 s, and 72° C./10 s; followed by 50 cycles at 95° C./10 s, 65° C./10 s, 72° C./10 s, and fluorescent signal detection at 54° C./20 s. Amplification was carried out in a Bio-Rad IQ-5 Multicolor Real-Time PCR Detection System (Bio-Rad, Hercules, Calif.) using the temperature gradient function that permits multiple amplification temperature profiles with different annealing temperatures to be run in the same instrument.

```
Additive EP020.
                                            (SEQ ID No. 12)
5' Dabcyl GAAATAAAATAAAAATAAAATA Dabcyl Dabcyl CTTTATTTTATTTTTATTTTAT Dabcyl 5'

Additive EP013.
                                            (SEQ ID No. 56)
5' Dabcyl GGTCAGATGAAAATGATACGTGp Dabcyl CCAGTCTACTTTTACTATGCAC Dabcyl 5'
```

Six assays were run. They had the following additives and initial annealing temperature (first 20 cycles):
Reaction 1: No additive, annealing temperature: 65° C.
Reaction 2: additive EP020, annealing temperature 65° C.
Reaction 3: additive EP020, annealing temperature 60.7° C.
Reaction 4: additive EP013, annealing temperature 66.5° C.
Reaction 5: additive EP013, annealing temperature 64.2° C.
Reaction 6: additive EP013, annealing temperature 60.7° C.

FIG. 9 presents the fluorescence readings from the probes as a function of the LATE-PCR thermal cycle number. FIG. 9A shows the readings from Reaction 1, wherein circle 911 is the readings from the first probe in the four replicates of amplification of the first target, and circle 912 is the readings from the second probe in the four replicates of amplification of the second target. FIG. 9B shows the readings from Reaction 2, wherein circle 913 is the readings from the first probe in the four replicates of amplification of the first target, and circle 914 is the readings from the second probe in the four replicates of amplification of the second target. FIG. 9C shows the readings from Reaction 3, wherein circle 915 is the readings from the first probe in the four replicates of amplification of the first target, and circle 916 is the readings from the second probe in the four replicates of amplification of the second target. FIG. 9D shows the readings from Reaction 4, wherein circle 917 is the readings from the first probe in the four replicates of amplification of the first target, and circle 918 is the readings from the second probe in the four replicates of amplification of the second target. FIG. 9E shows the readings from Reaction 5, wherein circle 919 is the readings from the first probe in the four replicates of amplification of the first target, and circle 920 is the readings from the second probe in the four replicates of amplification of the second target. FIG. 9F shows the readings from Reaction 6, wherein circle 921 is the readings from the first probe in the four replicates of amplification of the first target, and circle 922 is the readings from the second probe in the four replicates of amplification of the second target.

Example 6

A Primer-Independent Oscillating-Temperature Assay for Evaluating Inhibition of 5'Exonuclease Activity Many DNA polymerases, including Taq and Tfi(+) have the capacity to cleave the fluorescently labeled nucleotide on the 5' end of an oligonucleotide probe that is hybridized to its target strand. This 5' exonuclease cleavage even occurs under isothermal conditions in the absence of extension of an upstream primer. It is therefore primer-independent cleavage in contrast to primer-dependent cleavage that takes place in standard 5' nuclease amplification reactions. The rate of primer-independent 5' exonuclease cleavage can be increased by oscillating the temperature of the reaction mixture over a limited temperature range above and below the Tm of the probe/target hybrid.

Oscillation reactions were carried out in 25 ul volume consisting of 1×PCR buffer (Invitrogen, Carlsbad, Calif.), 3 mM $MgCl_2$, 200 nM dNTPs, 1.25 units of Taq DNA polymerase (Invitrogen, Carlsbad, Calif.), 200 nM of a probe having a 5'FAM and a 3' Black Hole Quencher 1 (BHQ1), and 100 nM of a complementary 41 nucleotide target. This reaction mixture was used with and without any additive and with each of the additives identified below at a concentration of 300 nM. A control reaction was run with the probe as the only oligonucleotide in the reaction mixture. The additives included PS060, a single-stranded additive that forms a stem-loop structure (complementary nucleotides forming the stem are underlined), as well as double-stranded additives. Reaction mixtures were oscillated using the following thermal profile: 45° C./20 s, 60° C./10 s for 45 cycles, followed by a melt starting at 45° C./30 secs with 1° C. increments for 30 cycles. The FAM fluorescence was acquired during the 45° C./10 s segment of the thermal profile. Sequences for the probe, target and additives were:

```
Probe.
                                            (SEQ ID No. 57)
5' FAM CCATGATACAAGCTTCC BHQ1

Target.
                                            (SEQ ID No. 58)
5' ACTTAGTAATTGGGAAGCTTGTATCATGGCACTTAGAACCT Additive EP001.
                                            (SEQ ID No. 23)
5' Dabcyl GGAGCAAAATAGCAATGAGGTA Dabcyl Dabcyl CCTCGTTTTATCGTTACTCCAT Dabcyl 5'

Additive EP004.
                                            (SEQ ID No. 26)
5' Dabcyl GGAGCAAAATAGCAATGAGGTAp Dabcyl CCTCGTTTTATCGTTACTCCAT Dabcyl 5'

Additive EP008.
                                            (SEQ ID No. 30)
5' Dabcyl GGAGCAAAATAGCAATGAGGTAp pCCTCGTTTTATCGTTACTCCAT Dabcyl 5'

Additive EP009.
                                            (SEQ ID No. 31)
5' GGAGCAAAATAGCAATGAGGTA Dabcyl Dabcyl CCTCGTTTTATCGTTACTCCAT 5'
```

-continued

Additive PS060.
(SEQ ID No. 59)
5' CGCGGCGTCAGGCATATAGGATACCGGGACAGAC

GCCGCG

Figure 10:
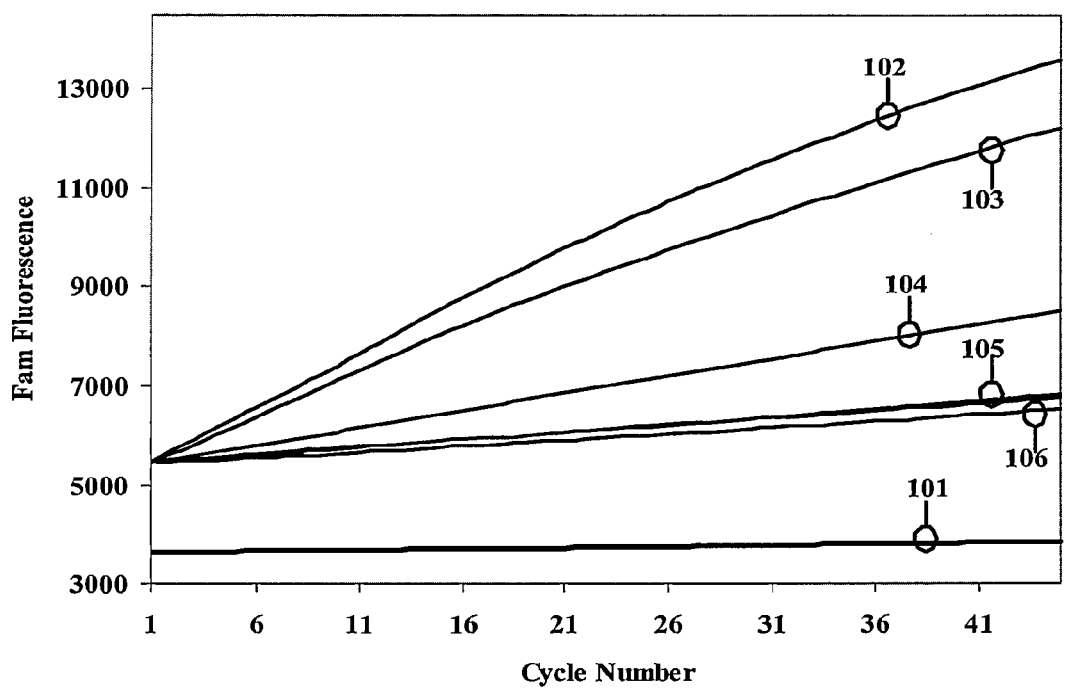
FIG. 10 is a graph of probe fluorescence as a function of the number of temperature oscillation cycles for a primer-independent probe-cleavage assay described in Example 6 utilizing any of several additives or no additive.

Exonuclease cleavage activity separates the probe's fluorophore from the probe, thereby resulting in an increase in fluorescence (FAM). Results are reported in FIG. 10. In FIG. 10, curve 101 for the probe-only reaction shows that in the absence of target, the probe is not cleaved. Curve 102 for the reaction containing probe and target but no additive, shows the highest probe cleavage. Curve 103 for PS060 shows higher probe cleavage than the curves for additives; that is, curve 104, EP009; curve 105, the same curve for EP004 and for EP008; and curve 106, EP001.

Example 7

Inhibitor of 5'Exonuclease Activity During PCR

After the LATE-PCR amplification as described in Example 5, the detection probe for the first target was hybridized to its complementary amplification products at 50° C. for 1 minute. The probe-target hybrids were then subjected to melting curve analysis by monitoring probe fluorescent intensities at 1° C. intervals of 30 seconds each between 50° C. and 80° C. as the probe was being melted from the amplicon. A no-template control containing only the probe was also subjected to melting regimen (fluorescence increases slightly with temperature in the absence of probe cleavage, because fluorescence intensity from the fluorophore is temperature dependent). Two samples were subjected to melting: one containing no additive and one containing additive EP013 (SEQ ID Nos 47 and 157) at 600 nM concentration.

Results are presented in FIGS. 11A and 11B. In FIG. 11A, curve 111 is for the probe alone, and curve 112 is for the amplification product of the reaction containing no additive. In FIG. 11B, curve 113 is for the probe alone, and curve 114 is for the amplification product containing the additive EP013. Inhibition of primer-dependent Taq DNA polymerase 5' exonuclease activity is evidenced by fluorescence signals from the probe melted off the amplification targets matching the fluorescence signals of control samples containing the probe alone when melting is completed.

Example 8

Large Multiplexed Reactions

Twelve pairs of primers, each for a different sequence within genes of the human mitochondrial genome, were combined into a single multiplex amplification mixture for a multiplex amplification of twelve different target sequences. The 25 ul reaction mixtures contained 1×PCR Buffer, 400 nM dNTPs, 3 mM MgCl$_2$, 0.24×SYBR Green, 50 nM Limiting Primer, 1000 nM Excess Primer, and 3.75 units of Tfi(-) DNA polymerase, with either no additive, additive EP011 at 300 nM concentration, or additive EP011 at 600 nM concentration.

Reaction mixtures were subjected to the following LATE-PCR thermal cycling protocol: 95° C. for 3 minutes followed by 65 cycles of 95° C./5 s, 58° C./20 s, and 68° C./2 m; followed by a melt starting at 45° C. with 1° C. increments at 30 s intervals to 95° C. Reactions were analyzed at the end of 65 cycles by a melt curve analysis using the first derivative of SYBR Green fluorescence (–dF/dT, SYBR) of double-stranded DNA product. In addition, the kinetics of production of double-stranded product (SYBR Green intensity reading as a function of thermal cycles) was analyzed for reactions.

The sequence of additive EP011, and the sequences of the 12 targets and the primers used to amplify each were are as follows:

Additive EP011.
(SEQ ID No. 60)
5' DabcylGGTCAGATGAAAATGATACGTG Dabcyl pCCAGTCTACTTTTACTATGCAC Dabcyl 5'

Target HV1.
(SEQ ID No. 61)
5' GCCCGGAGCGAGGAGAGTAGCACTCTTGTGCGGGATATTGA

TTTCACGGAGGATGGTGGTCAAGGGACCCCTATCTGAGGGG

GGTCATCCATGGGACGAGAAGGGATTTGACTGTAAT GTGC

TATGTACGGTAAATGGCTTTATGTACTATGTACTGTTAAGGG

TGGGTAGGTTTGTTGGTATCCTAGTGGGTGAGGGGTGGCTT

TGGAGTTGCAGTTGATGTGTGATAGTTGAGGGTTGATTGCT

GTACTTGCTTGTAAGCATGGGGAGGGGTTTTGATGTG GAT

TGGGTTTTTATGTACTACAGGTGGTCAAGTATTTATGGTAC

CGTACAATATTCATGGTGGCTGGCAGTAATGTACGAAATA

CATAGCGGTTGTTGATGGGTGAGTCAATACTTGGGTGGTAC

CCAAATCTGCTTCCCCATGAAAGAACAGAGAATAGTTTAA

ATTAGAATCTTAGCTTTGGGTGCTAATGGTGGAGTTAAAGACT

TTTTCTCTGATTTGTCCTTGGAAAAAGGTTTTCATCTCCGGT

TTACAAGACTGGTG

Limiting Primer.
(SEQ ID No. 62)
5' GCCCGGAGCGAGGAGAGTAGCACTCTTG

Excess Primer.
(SEQ ID No. 63)
5' CACCAGTCTTGTAAACCGGAGATGAA

Target HV2.
(SEQ ID No. 64)
5' ACAGGTCTATCACCCTATTAACCACTCACGGGAGCTCTCC

ATGCATTTGGTATTTTCGTCTGGGGGGTATGCACGCGATAGC

ATTGCGAGACGCTGGAGCCGGAGCACCCTATGTCGCAGTAT

CTGTCTTTGATTCCTGCCTCATCCTATTATTTATCGCACCTA

CGTTCAATATTACAGGCGAACATACTTACTAAAGTGTGTTA

ATTAATTAATGCTTGTAGGACATAATAATAACAATTGAAT

GTCTGCACAGCCACTTTCCACACAGACATCATAACAAAAA

ATTTCCACCAAACCCCCCCTCCCCCGCTTCTGGCCACAGCA

CTTAAACACATCTCTGCCAAACCCCAAAAACAAAGAACCC

TAACACCAGCCTAACCAGATTTCAAATTTTATCTTTTGGCG

GTATGCACTTTTAACAGTCACCCCCCAACTAACACATTATT

TTCCCCTCCCACTCCCATACTACTAATCTCATCAATACAAC

CCCCGCCCATCCTACCCAGCACACACACACCGCTG

Limiting Primer.

(SEQ ID No. 65)

5' AGCGGTGTGTGTGCTGGGTAGGAT

Excess Primer.

(SEQ ID No. 66)

5' ACAGGTCTATCACCCTATTAACCACTCA

Target CO1-1.

(SEQ ID No. 67)

5' AGGTTGCGGTCTGTTAGTAGTATAGTGATGCCAGCAGCT

AGGACTGGGAGAGATAGGAGAAGTAGGACTGCTGTGATT

AGGACGGATCAGACGAAGAGGGGCGTTTGGTATTGGGTTA

TGGCAGGGGGTTTTATATTGATAATTGTTGTGATGAAATTG

ATGGCCCCTAAGATAGAGGAGACACCTGCTAGGTGTAAGG

AGAAGATGGTTAGGTCTACGGAGGCTCCAGGGTGGGAGT

AGTTCCCTGCTAAGGGAGGGTAGACTGTTCAACCTGTTCCT

GCTCCGGCCTCCACTATAGCAGATGCGAGCAGGAGTAGG

AGAGAGGGAGGTAAGAGTCAGAAGCTTATGTTGTTTATGC

GGGGAAACGCCATATCGGGGGCACCGATTATTAGGGGAAC

TAGTCAGTTGCCAAAGCCTCCGATTATGATGGGTATTACT

ATGAAGAAGATTATTACAAATGCATGGGCTGTGACGATAA

CGTTGTAGATGTGGTCGTTACCTAGAAGGTTGCCTGGCTGG

CCCAGCTCGGCTCGAATAAGGAGGCTTAGAGCTGTGCCTA

GGACTCCAGCTCATGCGCCGAATAATAGGTATAGTGTTCCA

ATGTCTTTGTGGTTTGTAGAGAATAGTCAACGGT

Limiting Primer.

(SEQ ID No. 68)

5' AGGTTGCGGTCTGTTAGTAGTATAGTGATGCCAGCA

Excess Primer.

(SEQ ID No. 69)

5' ACCGTTGACTATTCTCTACAAACCACA

Target CO1-2.

(SEQ ID No. 70)

5' ATGGAGGGTTCTTCTACTATTAGGACTTTTCGCTTCGAAG

CGAAGGCTTCTCAAATCATGAAAATTATTAATATTACTGCT

GTTAGAGAAATGAATGAGCCTACAGATGATAGGATGTTTC

ATGTGGTGTATGCATCGGGGTAGTCCGAGTAACGTCGGGG

CATTCCGGATAGGCCGAGAAAGTGTTGTGGGAAGAAAGTT

AGATTTACGCCGATGAATATGATAGTGAAATGGATTTTGGC

GTAGGTTTGGTCTAGGGTGTAGCCTGAGAATAGGGGAAATC

AGTGAATGAAGCCTCCTATGATGGCAAATACAGCTCCTAT

TGATAGGACATAGTGGAAGTGGGCTACAACGTAGTACGTG

TCGTGTAGTACGATGTCTAGTGATGAGTTTGCTAATACAAT

GCCAGTCAGGCCACCTACGGTGAAAAGAAAGATGAATCC

TAGGGCTCAGAGCACTGCAGCAGATCATTTCATATTGCTTC

CGTGGAGTGTGGCGAGTCAGCTAAATACTTTGACGCCGGT

GGGGATAGCGATGATTATGGTAGCGGAGGTGAAATATGCT

CGTGTGTCTACGTCTATTCCTACTGTAAATATATGGTGTGC

TCACACGATAAACCCTAGGAAGCCAATTGATATCATAGCT

CAGACCATACCTATGTATCCAAATGGTTCTTTTTTTCCGGA

GTAGTAAGTTACAATATGGGAGATTATTCCGAAGCCTGG

TAGGAT

Limiting Primer.

(SEQ ID No. 71)

5' ATGGAGGGTTCTTCTACTATTAGGACTTTTCGCT

Excess Primer.

(SEQ ID No. 72)

5' ATCCTACCAGGCTTCGGAATAATCTC

Target CO2.

(SEQ ID No. 73)

5' AGGGTAAATACGGGCCCTATTTCAAAGATTTTTAGGGG

AATTAATTCTAGGACGATGGGCATGAAACTGTGGTTTGCTC

CACAGATTTCAGAGCATTGACCGTAGTATACCCCCGGTCG

TGTAGCGGTGAAAGTGGTTTGGTTTAGACGTCCGGGAATTG

CATCTGTTTTTAAGCCTAATGTGGGGACAGCTCATGAGTGCA

AGACGTCTTGTGATGTAATTATTATACGAATGGGGGCTTCA

ATCGGGAGTACTACTCGATTGTCAACGTCAAGGAGTCGCA

GGTCGCCTGGTTCTAGGAATAATGGGGAAGTATGTAGGA

GTTGAAGATTAGTCCGCCGTAGTCGGTGTACTCGTAGGTTC

AGTACCATTGGTGGCCAATTGATTTGATGGTAAGGGAGGG

ATCGTTGACCTCGTCTGTTATGTAAAGGATGCGTAGGGAT

GGGAGGGCGATGAGGACTAGGATGATGGCGGGCAGGATA

GTTCAGACGGTTTCTATTTCCTGAGCGTCTGAGATGTTAGTA

TTAGTTAGTTTTGTTGTGAGTGTTAGGAAAAGGGCATACA

GGACTAGGAAGCAGATAAGGA

Limiting Primer.

(SEQ ID No. 74)

5' AGGGTAAATACGGGCCCTATTTCAAAGATTTTTAGGGGA

Excess Primer.

(SEQ ID No. 75)

5' TCCTTATCTGCTTCCTAGTCCTGTATGC

Target 12srRNA.

(SEQ ID No. 76)

5' CCTCTAAATCACCACGATCAAAAGGAACAAGCATCAA

GCACGCAGCAATGCAGCTCAAAACGCTTAGCCTAGCCA

CACCCCCACGGGAAACAGCAGTGATTAACCTTTAGCAATA

AACGAAAGTTTAACTAAGCTATACTAACCCCAGGGTT

GGTCAATTTCGTGCCAGCCACCGCGGTCACACGATTA

ACCCAAGTCAATAGAAGCCGGCGTAAAGAGTGTTTTAGAT

CACCCCCTCCCCAATAAAGCTAAAACTCACCTGAGTTGT

AAAAAACTCCAGTTGACACAAAATAGACTACGAAAGTGG

CTTTAACATATCTGAACACACAATAGCTAAGACCCAAAC

TGGGATTAGATACCCCACTATGCTTAGCCCTAAACCTCAA

CAGTTAAATCAACAAAACTGCTCGCCAGAACACTACGAG

CCACAGCTTAAAACTCAAAGGACCTGGCGGTGCTTCATA

-continued
TCCCTCTAGAGGAGCCTGTTCTGTAATCGATAAACCCCGA

TCAACCTCACCACCTCTTGCTCAGCCTATATACCGCCATC

TTCAGCAAACCCTGATGAAGGCTACAAAGTAAGCGCAAG

TACCCACGTAAAGACGTTAGGTCAAGGTGTAGCCCATGAG

GTGGCAAGAAATGGGCTACATTTTCTACCCCAGAAAACT

ACGATAGCCCTTATGAAACTTAAGGGTCGAAGGTGGATT

TAGCAGTAAACTAAGAGTAGAGTGCTTAGTTGAACAGGG

CCCTGAAGCGCGTACACACCGCCCGTCACCCTCCTCAAG

TATACTTCAAAGGACATTTAACTAAAACCCCTACGCATT

TATATAGAGGAGACAAGTCGTAACATGGTAAGTGT

ACTGGA

Limiting Primer.
(SEQ ID No. 77)
5' TCCAGTACACTTACCATGTTACGACTTGTCTCCTCTA

Excess Primer.
(SEQ ID No. 78)
5' CCTCTAAATCACCACGATCAAAAGGAAC

Target Cytb-1.
(SEQ ID No. 79)
5' TGTGAGGGTGGGACTGTCTACTGAGTAGCCTCCTCAGAT

TCATTGAACTAGGTCTGTCCCAATGTATGGGATGGCGGATA

GTAAGTTTGTAATTACTGTGGCCCCTCAGAATGATATTTGG

CCTCACGGGAGGACATAGCCTATGAAGGCTGTTGCTATAG

TTGCAAGCAGGAGGATAATGCCGATGTTTCAGGTTTCTGA

GTAGAGAAATGATCCGTAATATAGGCCTCGCCCGATGTGT

AGGAAGAGGCAGATAAAGAATATTGAGGCGCCATTGGCG

TGAAGGTAGCGGATGATTCAGCCATAATTTACGTCTCGAG

TGATGTGGGCGATTGATGAAAAGGCGGTTGAGGCGTCTGG

TGAGTAGTGCATGGCTAGGAATAGTCCTGTGGTGATTTGG

AGGATCAGGCAGGCGCCAAGGAGTGAGCCGAAGTTTC

ATCATGCGGA

Limiting Primer.
(SEQ ID No. 80)
5' TGTGAGGGTGGGACTGTCTACTGAGTAGCC

Excess Primer.
(SEQ ID No. 81)
5' TCCGCATGATGAAACTTCGGCTC

Target Cytb-2.
(SEQ ID No. 82)
5' ACTCCACCTCCTATTCTTGCACGAAACGGGATCAAACAA

CCCCCTAGGAATCACCTCCCATTCCGATAAAATCACCTTCC

ACCCTTACTACACAATCAAAGACGCCCTCGGCTTACTTCTCT

TCCTTCTCTCCTTAATGACATTAACACTATTCTCACCAGAC

CTCCTAGGCGACCCAGACAATTATACCCTAGCCAACCCCT

TAAACACCCCTCCCCACATCAAGCCCGAATGATATTTCCT

ATTCGCCTACACAATTCTCCGATCCGTCCCTAACAAACTAG

GAGGCGTCCTTGCCCTATTACTATCCATCCTCATCCTAGCA

ATAATCCCCATCCTCCATATATCCAAACAACAAAGCATAAT

ATTTCGCCCACTAAGCCAATCACTTTATTGACTCCTAGCCG

CAGACCTCCTCATTCTAACCTGAATCG

Limiting Primer.
(SEQ ID No. 83)
5' CGATTCAGGTTAGAATGAGGAGGTCTGCGGCTAG

Excess Primer.
(SEQ ID No. 84)
5' ACTCCACCTCCTATTCTTGCACGA

Target ND1.
(SEQ ID No. 85)
5' CATAAGAACAGGGAGGTTAGAAGTAGGGTCTTGGTGACAA

AATATGTTGTGTAGAGTTCAGGGGAGAGTGCGTCATATGT

TGTTCCTAGGAAGATTGTAGTGGTGAGGGTGTTTATTATAA

TAATGTTTGTGTATTCGGCTATGAAGAATAGGGCGAAGGG

GCCTGCGGCGTATTCGATGTTGAAGCCTGAGACTAGTTCGG

ACTCCCCTTCGGCAAGGTCGAAGGGGGTTCGGTTGGTCTC

TGCTAGTGTGGAGATAAATCATATTATGGCCAAGGGTCAT

GATGGCAGGAGTAATCAGAGGTGTTCTTGTGTTGTGATAA

GGGTGGAGAGGTTAAAGGAGCCACTTATTAGTAATGTTGA

TAGTAGAATGATGGCTAGGGTGACTTCATATGAGATTGTTT

GGGCTACTGCTCGCAGTGCGCCGATCAGGGCGTAGTTTGAG

TTTGATGCTCACCCTGATCAGAGGATTGAGTAAACGGCTA

GGCTAGAGGTGGCTAGAATAAATAGGAGGCCTAGGTTGA

GGTTGACCAGGGGGTTGGGTATGGGGAGGGGGGTTCATA

GTAGAAGAGCGATGGTGAGAGCTAAGGTCGGGGCGGTGA

TGTAGAGGGTGATGGTAGATGTGGCGGGTTTTAGGGG

Limiting Primer.
(SEQ ID No. 86)
5' CATAAGAACAGGGAGGTTAGAAGTAGGGTCTTGGT

Excess Primer.
(SEQ ID No. 87)
5' CCCCTAAAACCCGCCACAT

Target ND2.
(SEQ ID No. 88)
5' AGTGTGATTGAGGTGGAGTAGATTAGGCGTAGGTAGAA

GTAGAGGTTAAGGAGGGTGATGGTGGCTATGATGGTGGGG

ATGATGAGGCTATTGTTTTTGTGAATTCTTCGATAATGGC

CCATTTGGGCAAAAGCCGGTTAGCGGGGGCAGGCCTCC

TAGGGAGAGGAGGGTGGATGGAATTAAGGGTGTTAGTCAT

GTTAGCTTGTTTCAGGTGCGAGATAGTAGTAGGGTCGTGGT

GCTGGAGTTTAAGTTGAGTAGTAGGAATGCGGTAGTAGTT

AGGATAATATAAATAGTTAAATTAAGAATGGTTATGTTAG

GGTTGTACGGTAGAACTGCTATTATTCATCCTATGTGGGTA

ATTGAGGAGTATGCTAAGATTTTGCGTAGCTGGGTTTGGTT

TAATCCACCTCAACTGCCTGCTATGATGGATAAGATTGAG

AGAGTGAGGAGAAGGCTTACGTTTAGTGAGGGAGAGATTT

```
GGTATATGATTGAGATGGGGCTAGTTTTTGTCATGTGAG

AAGAAGCAGGCCGGATGTCAGAGGGGTGCCTTGGGTAACC

TCTGGGACTCAGAAGTGAAAGGGGGCTATTCCTAGTTTTAT

TGCTATAGCTATTATGATTATTAATGATGAGTATTGATTGG

TAGTATTGGTTATGGTTCATTGTCCGGAGAGTATATTGTTG

AAGAGGATAGCTATTAGAAGGATTATGGATGCGGTTGCTT

GCGTGAGGAAATACTTGATGGCAGCTTCTGTGGAACGAGGG

TTTATTTTTTGGTTAGAACTGGAATAAAAGCTAGCATGTTT

ATTTCTAGGCCTACTCAGGTAAAAAATCAGTGCGAGCTTA

GCGCTGTGATGAGTGTGCCTGCA

Limiting Primer
                                    (SEQ ID No. 89)
5' AGTGTGATTGAGGTGGAGTAGATTAGGCGTAGGT

AGAAGT

Excess Primer.
                                    (SEQ ID No. 90)
5' TGCAGGCACACTCATCACAGCGCTAAGCT Target ND4-1.
                                    (SEQ ID No. 91)
5' AACACAACCACCCACAGCCTAATTATTAGCATCATCCCTC

TACTATTTTTAACCAAATCAACAACAACCTATTTAGCTGTT

CCCCAACCTTTTCCTCCGACCCCCTAACAACCCCCCTCCTA

ATACTAACTACCTGACTCCTACCCCTCACAATCATGGCAAG

CCAACGCCACTTATCCAGTGAACCACTATCACGAAAAAAA

CTCTACCTCTCTATACTAATCTCCCTACAAATCTCCTTAATT

ATAACATTCACAGCCACAGAACTAATCATATTTTATATCTT

CTTCGAAACCACACTTATCCCCACCTTGGCTATCATCACCC

GATGAGGCAACCAGCCAGAACGCCTGAACGCAGGCACATA

CTTCCTATTCTACACCCTAGTAGGCTCCCTTCCCCTACTCAT

CGCACTAATTTACACTCACAACACCCTAGGCTCACTAAACA

TTCTACTACTCACTCTCACTGCCCAAGAACTATCAA

ACTCCTGAGC

Limiting Primer.
                                    (SEQ ID No. 92)
5' GCTCAGGAGTTTGATAGTTCTTGGGCAGTGAGAG Excess Primer.
                                    (SEQ ID No. 93)
5' AACACAACCACCCACAGCCTAATTATTAG Target ND4-2.
                                    (SEQ ID No. 94)
5' GTGGTGGGTGAGTGAGCCCATTGTGTTGTGGTAAATAT

GTAGAGGGAGTATAGGGCTGTGACTAGTATGTTGAGTCCT

GTAAGTAGGAGAGTGATATTTGATCAGGAGAACGTGGTTA

CTAGCACAGAGAGTTCTCCCAGTAGGTTAATAGTGGGGGG

TAAGGCGAGGTTAGCGAGGCTTGCTAGAAGTCATCAAAAA

GCTATTAGTGGGAGTAGAGTTTGAAGTCCTTGAGAGAGGA

TTATGATGCGACTGTGAGTGCGTTCGTAGTTTGAGTTTGCT

AGGCAGAATAGTAATGAGGATGTAAGCCCGTGGGCGATTA

TGAGAATGACTGCGCCGGTGAAGCTTCAGGGGGTTTGGAT

GAGAATGGCTGTTACTACGAGGGCTATGTGGCTGATTGAA

GAGTATGCAATGAGCGATTTTAGGTCTGTTTGTCGTAGGCA

GATGGAGCTTGTTATAATTATGCCTCATAGGGATAGTACA

AGGAAGGGGTAG

Limiting Primer.
                                    (SEQ ID No. 95)
5' GTGGTGGGTGAGTGAGCCCCATTGTGT Excess Primer.
                                    (SEQ ID No. 96)
5' CTACCCCTTCCTTGTACTATCCCTATGAG
```

The amplified products were then analyzed using a 5% Polyacrylamide gel, loaded with 1 ul of PCR product combined with 1 ul of loading dye. The gel was run for eight hours at 30 volts at 4° C. The gel was developed for ten minutes using SYBR Gold. A photograph of the gel is presented in FIG. 12. The first lane is the reaction with no additive. The second lane is the reaction with additive EP011 at 300 nM concentration. The third lane is the reaction with additive EP011 at 600 nM concentration. As can be seen from FIG. 12, the reaction without additive failed to generate the expected set of twelve products. From lane 2 it can be seen that 300 nM of additive EP011 suppressed most mispriming (one band of light weight product can be seen at the bottom). From lane 3 it can be seen that additive EP011 at 600 nM concentration suppressed all mispriming.

The reaction containing 600 nM additive EP011 was subjected to the sequencing sample preparation known as the Dilute-'N'-Go method. See, Rice, J. E. et al. (2007), Monoplex/Multiplex Linear-After-The-Exponential PCR Assay Combined with PrimeSafe and Dilute-'N'-Go Sequencing, *Nature Protocols* 2: 2429-2438. The prepared sample was divided into twelve aliquots, and each aliquot was subjected to dideoxy sequencing utilizing one of the twelve limiting primers as the sequencing primer. Sequencing results demonstrated that the amplification reaction generated a sufficient single-stranded DNA for each amplicon to permit sequencing of each of the 12 different Limiting Primer strands from a single reaction via the Dilute 'N' Go dideoxy sequencing protocol.

The above results were obtained using 1000 copies of mitochondrial genomic DNA in each reaction. Additional samples in this experiment (results not shown) demonstrated that complete amplification of all 12 products was not obtained when each reaction contained only 100 or 10 copies of mitochondrial genomic DNA. This is consistent with the fact that Type 1 and Type 3 mispriming increase with decreasing numbers of targets.

But, 100 and 10 copies of mitochondrial genomic DNA can be successfully amplified with the multiplex reaction described above after making the following adjustments: 1) use EP043 with a combination of strands at 50/600/550 nM; 2) increase the number of amplification cycles to 80-90; and 3) in accord with Example 14 alter the limiting primers for the following targets by addition of at least two mismatched A's or T's to their 5' ends (indicated by underlining).

```
For target HV1:
Limiting Primer.
                                    (SEQ ID No. 97)
5' TAAAGCCCGGAGCGAGGAGAGTAGCACTCTTG
```

```
-continued
For target HV2:
Limiting Primer.
                                        (SEQ ID No. 98)
5' AAAGCGGTGTGTGTGCTGGGTAGGAT For target CO1-1:
Limiting Primer.
                                        (SEQ ID No. 99)
5' AAAGGTTGCGGTCTGTTAGTAGTATAGTGATGCCAGCA For target CO1-2:
Limiting Primer.
                                       (SEQ ID No. 100)
5' AAATGGAGGGTTCTTCTACTATTAGGACTTTTCGCT For target CO2:
Limiting Primer.
                                       (SEQ ID No. 101)
5' TAAGGGTAAATACGGGCCCTATTTCAAAGATTTTT

AGGGGA

For target 12srRNA:
Limiting Primer.
                                       (SEQ ID No. 102)
5' AATCCAGTACACTTACCATGTTACGACTTGTCTCCTCTA For target Cytb-1:
Limiting Primer.
                                       (SEQ ID No. 103)
5' AATGTGAGGGTGGGACTGTCTACTGAGTAGCC For target Cytb-2:
Limiting Primer.
                                       (SEQ ID No. 104)
5' AACGATTCAGGTTAGAATGAGGAGGTCTGCGGCTAG For target ND1:
Limiting:
                                       (SEQ ID No. 105)
5'AACATAAGAACAGGGAGGTTAGAAGTAGGGTCTTGGT For target ND2:
Limiting Primer.
                                       (SEQ ID No. 106)
5' AAAGTGTGATTGAGGTGGAGTAGATTAGGCGT

AGGTAGAAGT

For target ND4-1:
Limiting Primer.
                                       (SEQ ID No. 107)
5' AAGCTCAGGAGTTTGATAGTTCTTGGGCAGTGAGAG For target ND4-2:
Limiting Primer.
                                       (SEQ ID No. 108)
5' TAGTGGTGGGTGAGTGAGCCCCATTGTGT
```

Example 9

Direct Quantitative Measure of Suppression of Type 1 Mispriming

The assay reported in this example was developed to measure Type I mispriming and the effect of additives and hot-start reagents in suppressing Type I mispriming. In this assay, two overlapping oligonucleotides that can anneal and extend are first incubated at a temperature (50° C.) below a LATE-PCR annealing temperature for an extended period (10 minutes). If extension occurs, priming sites for a pair of LATE-PCR primers are created, that is, the extended overlapping nucleotides include the priming sites but the oligonucleotides themselves contain only the complements of the priming sites. The reaction mixture is then subjected to LATE-PCR amplification using the primer pair. Under these conditions, the number of cycles required to generate a detectable level of product (observed with either SYBR Green or a probe to the Excess-Primer-Strand) will depend on how many extended (or full length) strands are generated during the initial isothermal incubation of the partially complementary oligomers. This, in turn, will depend on how active the DNA polymerase is during isothermal incubation. By comparing the threshold cycles ($C_T$) of a reaction with an inhibitor to a reaction with no inhibitor, one obtains a quantitative measure of the effect of the inhibitor in suppressing the initial, isothermal extension, which is considered to be a mispriming event in this assay. The lowest $C_T$ value is observed when all oligomers present initially are fully extended prior to the first round of amplification. Higher and higher $C_T$ values are observed with greater and greater inhibition of DNA polymerase. After the respective combinations of reactions were mixed and prior to the isothermal incubation at 50° C. all reactions had the overlap oligonucleotides 1 and 2 added at approximately 100,000 copies each.

The following oligonucleotides were used. For the overlapping oligonucleotides, the sequences complementary to priming sites are underlined, and overlapping sequences are italicized.

```
Overlapping oligonucleotide 1:
                                       (SEQ ID No. 109)
5' TTGCACGAGAGCCAGCTCGTCAGGTAGTCACCAGTACAGTCCGCT

TGTGTCAAGACAGCACG

Overlapping oligonucleotide 2
                                       (SEQ ID No. 110)
5' CAGCAGCAGACAGTGCACTCGTCACTCACTAACCGCTATTCGAGTT

CGCGTGCTGTCTTGACACAAGCGGACTGT

Limiting Primer:
                                       (SEQ ID No. 111)
5' TTGCACGAGAGCCAGCTCGTCAGGTAGTCACCAGT Excess Primer:
                                       (SEQ ID No. 112)
5' CAGCAGCAGACAGTGCACTCGTCAC Additive EP046.
                                       (SEQ ID No. 113)
5' Dabcyl GGAGCAGACTAGCACTGAGGTA Dabcyl Dabcyl CCTCGTCTGATCGTGACTCCAT Dabcyl 5'

Additive EP020.
                                        (SEQ ID No. 12)
5' Dabcyl GAAATAAAATAAAAATAAAATA Dabcyl Dabcyl CTTTATTTTATTTTTATTTTAT Dabcyl 5'

Additive EP022.
                                        (SEQ ID No. 14)
5' Dabcyl CCGCCGGC Dabcyl Dabcyl GGCGGCCG Dabcyl 5'
```

Each reaction was carried out in triplicate in a 25 ul reaction. Each reaction mixture contained 1×PCR buffer (Invitrogen, Carlsbad, Calif.), 3 mM $MgCl_2$, 250 nM dNTPs, 0.24× SYBR Green (Invitrogen, Carlsbad, Calif.), and 1.25 units of Taq DNA polymerase (Invitrogen, Carlsbad, Calif.). One reaction mixture contained only Taq DNA polymerase. A second reaction mixture contained Taq DNA polymerase and additive EP046 at 600 nM concentration. A third reaction mixture contained "hot start" Taq DNA polymerase with antibody (Invitrogen, Carlsbad, Calif.). A fourth reaction mixture contained Taq DNA polymerase with antibody and additive EP046 at 600 nM concentration. After the respective combinations of reaction ingredients were mixed and prior to the isothermal incubation at 50° C., all reactions had the overlapping oligonucleotides 1 and 2 added at approximately 100,000 copies each.

The thermal profile conditions for these reactions were as follows: 50° C. for 10 minutes followed by incubation on ice for long enough to add the primers, followed by rapid heating to 98° C., then 60 cycles at 98° C./10 s and 72° C./40 s. The melting temperature of the hybrid formed by the overlapping oligonucleotides was about 60° C., that is, well above the temperature of the initial 10-minute incubation. The annealing/extension temperature of the two-step PCR protocol was below the concentration-adjusted melting temperatures of the limiting and excess primers, which were 75.1° C. and 73.6° C., respectively, calculated according to the method given in Example 1. Each of the samples was analyzed by SYBR Green fluorescence in real-time, and at the end of the run each was subjected to melt curve analysis to confirm that the reaction generated a single product peak of 88° C. as expected for the double-stranded product of the amplification reaction (not shown).

SYBR Green fluorescence as a function of amplification cycle is shown in FIG. 13, where circle 131 identifies the replicates from the sample with Taq DNA polymerase only, circle 132 identifies the replicates from the sample with Taq DNA polymerase and the additive EP046, circle 133 identifies the replicates from the sample with Taq DNA polymerase-plus-antibody and circle 134 identifies the replicates from the sample with Taq DNA polymerase-plus-antibody and additive EP046.

Example 10

Mispriming and "ColdStop" Detection

To determine whether or not it is possible to interrupt a PCR amplification to perform some low-temperature operation. Mispriming effects of doing so need to be determined. We have developed the assay reported in this example for that purpose. The assay is a LATE-PCR amplification assay in which we have utilized the following target strand, primers and hybridization probe (labeled on one end with the fluorophore Quasar670 (Biosearch Technologies, Novato, Calif.) and on the other end with the quencher BHQ2 (Biosearch Technologies, Novato, Calif.):

```
Limiting Primer.
                                        (SEQ ID No. 114)
5' CTCCAGCCCGGCACGCTCACGTGACAGACCG Excess Primer.
                                        (SEQ ID No. 115)
5' CCGGTGGTCGCCGCGATCAAGGAG Probe.
                                        (SEQ ID No. 116)
5' Quasar670 GCGGGTTGTTCTGGTCCATGA BHQ2

Target.
                                        (SEQ ID No. 117)
5' CCGGTGGTCGCCGCGATCAAGGAGTTCTTCGGCACCAGCCA

GCTGAGCCAATTCATGGACCAGAACAACCCGCTGTCGGGG

TTGACCCACAAGCGCCGACTGTCGGCGCTGGGGCCCGGCG

GTCTGTCACGTGAGCGTGCCGGGCTGGAG
```

The reaction mixture included 1×PCR buffer (Invitrogen, Carlsbad, Calif.), 2 mM MgCl$_2$, 200 nM dNTPs, 50 nM of limiting primer, 1000 nM of excess primer, 200 nM of probe, 1.25 units of Taq DNA polymerase (Invitrogen, Carlsbad, Calif.), and an additive to be tested, in this case additive EP010 at 600 nM concentration. In addition, each reaction contained 10 million copies of human genomic DNA (Sigma-Aldrich, St. Louis, Mo.). The sequence of the tested additive was:

```
Additive EP010.
                                        (SEQ ID No. 10)
5' Dabcyl GGTCAGATGAAAATGATACGTG Dabcyl Dabcyl CCAGTCTACTTTTACTATGCAC Dabcyl 5'
```

Three control assays were first performed with the test additive included in the reaction mixture but without any interruption of the thermal cycling protocol to establish that the uninterrupted protocol was both sensitive and robust. The control assays were begun with 1000, 100 and 10 copies of the target strand in the amplification reaction mixture. Thermal cycling regimen was 98° C. for 3 minutes, followed by 70 cycles of 98° C./10 s. 75° C./40 s. 60° C./30 s, with fluorescence reading at 60° C. FIG. 14A presents the fluorescence readings from the probe as a function of PCR cycle number, with circle 141 being the readings from the four replicate amplifications of the sample with 1000 copies of target, circle 142 (dashed lines) being the readings from the replicates of the sample with 100 copies of target, and circle 143 being from the replicates of the sample with 10 copies of target.

A separate reaction mixture was subjected to a thermal cycling protocol that was interrupted. The thermal profile was 1 minute at 98° C. followed by 40 cycles of 98° C./10 s, 75° C./40 s, then a melt starting at 45° C. and increasing in 1° C. steps every 30 seconds (data acquisition for each step) for 40 steps, followed by 30 more cycles of 98° C./10 s, 75° C./40 s, at the conclusion of which the melt was repeated.

Results from the two melts are presented in FIG. 14B and FIG. 14C. These figures present melt curves in which the fluorescent values at each temperature are normalized by being divided by the fluorescent value at 75° C., a temperature at which the probe is not bound to the single-stranded product. Normalized melts were determined after 40 amplification cycles (FIG. 14B) and after 70 cycles, following the conclusion of amplification (FIG. 14C). In FIG. 14B, circle 144 is the replicates for 1000 copies of the target, circle 145 is the replicates of the sample with 100 copies of target, and circle 146 is the replicates of the sample with 10 copies of target. Similarly, in FIG. 14C, circle 147 (solid black lines) is the three replicate amplifications of the sample with 1000 copies of target, circle 148 (dashed lines) is the replicates of the sample with 100 copies of target, and circle 149 (solid gray lines) is the replicates of the sample with 10 copies of target.

Example 11

Type II Mispriming in Symmetric PCR Reactions

To demonstrate the effect of additives on the specificity of conventional symmetric PCR, allele-discriminating primers, the following assay was performed. Equal concentrations of two DNA target sequences differing at a single nucleotide position were amplified in parallel under symmetric PCR conditions in the presence or absence of additive EP043 (SEQ ID No. 45) using a primer pair in which one primer is specific (allele-specific primer) for one those DNA targets DNA (designated as the "matched target"). As suggested in the literature (Newton et al., Analysis of any point mutation in DNA. The amplification refractory mutation system (ARMS). 1989, Nucleic Acids Res. 17:2503-2516), a pair of symmetric PCR primers for preferential amplification of the matched target was constructed such that 3' end of one of the primers is complementary to the nucleotide unique to the intended DNA target and the penultimate 3' end position is mismatched to both the intended and the unintended DNA targets. Thus, the primer specific for the intended target is mismatched only once at its 3' end to the intended DNA target, but it is mismatched twice at its 3' end to the mismatched target. This primer design results in preferential amplification of the matched target. Prior to this experiment, genomic DNA samples containing the matched and mismatched targets were quantified with primers fully complementary to both targets to normalize the data for differences in target genome concentration. In this instance, the $C_T$ for the mismatched target was lower than the $C_T$ for the matched target by 1.52, so for assays using the allele-specific primer, any noted delay in the $C_T$ of the mismatched target had to be corrected by adding 1.52 to the observed $\Delta C_T$ to account for target concentration difference.

The target and primer sequences for preferential amplification, and the additive sequence were:

```
Allele-Specific Primer.
                                      (SEQ ID No. 118)
5' TATCGTCAAGGCACTCTTGCCTACGCCTT Common Primer.
                                      (SEQ ID No. 119)
5' GTACTGGTGGAGTATTTGATAGTGTATTAACC Matched Target.
                                      (SEQ ID No. 120)
5' GTACTGGTGGAGTATTTGATAGTGTATTAACCTTATGTGT

GACATGTTCTAATATAGTCACATTTTCATTATTTTTATTATA

AGGCCTGCTGAAAATGACTGAATATAAACTTGTGGTAGTT

GGAGCTGATGGCGTAGGCAAGAGTGCCTTGACGATA

Mismatehed Target.
                                      (SEQ ID No. 121)
5' GTACTGGTGGAGTATTTGATAGTGTATTAACCTTATGT

GTGACATGTTCTAATATAGTCACATTTTCATTATTTTT

ATTATAAGGCCTGCTGAAAATGACTGAATATAAACTT

GTGGTAGTTGGAGCTGGTGGCGTAGGCAAGAGTGC

CTTGACGATA

Additive EP043.
                                      (SEQ ID No. 48)
5' GGAGCAGACTAGCACTGAGGTA Dabcyl Dabcyl CCTCGTCTGATCGTGACTCCAT Dabcyl 5'

5' Dabcyl AGACTAGCACTGAGGTA Dabcyl
```

Symmetric PCR amplification were carried out in 1× Platinum Taq buffer (Invitrogen, Carlsbad, Calif.), 3 mM MgCl$_2$, 0.2 mM dNTP, 1 uM of primer pair, 0.24×SYBR Green (Invitrogen, Carlsbad, Calif.), 1 unit Platinum Taq DNA polymerase (Invitrogen, Carlsbad, Calif.) and 1000 genomes equivalents of human DNA containing either the matched or the mismatched target sequence in a final reaction volume of 25 ul. The reaction mixture either contained no additive or contained additive EP043 at a total concentration of 300 nM, with the top strand at 100 nM, the middle strand at 300 nM, and the bottom strand at 200 nM concentration.

The amplification conditions were 94° C. for 5 minutes; followed by 60 cycles of 94° C./1 minute (m), 64° C./1 m, 72° C./1 m, with data acquisition at the 72° C. step; and a final extension step of 72° C./10 m. Amplification was carried out in a Bio-Rad IQ-5 Multicolor Real-Time PCR Detection System (Bio-Rad, Hercules, Calif.).

From SYBR green real-time fluorescence signals it was determined that in the assay containing no additive, signal from the mismatched target was delayed relative to signal from the matched target, giving a corrected $\Delta C_T$ of 7.84. Similarly, in the assay containing additive EP043 at a total of 300 nM concentration signal from the mismatched target was even more delayed relative to signal from the matched target, giving a corrected $\Delta C_T$ of 12.59. Accordingly, increased polymerase specificity due to the presence of EP043 was 4.75 cycles.

Example 12

Inhibition of Taq DNA Polymerase Activity and AT Content of Limiting Primer 3' End LATE-PCR assays utilizing a limiting primer GC rich at its 3' end and a limiting primer AT rich at its 3' end were compared as to the delay caused by the presence of an additive as described herein. Four amplification reactions were performed: one using the primer having the GC rich 3' end and no additive, a second using the same primer and additive EP013; a third using the primer having the AT rich 3' end and no additive; and a fourth using the same primer and additive EP013.

Each 25 ul amplification reaction mixture included 1× Platinum Taq buffer (Invitrogen, Carlsbad, Calif.), 3 mM MgCl$_2$, 250 nM dNTP, 1.25 units Platinum Taq polymerase (Invitrogen, Carlsbad, Calif.), 1000 genomes equivalents of human DNA, excess primer at 1000 nM concentration, limiting primer at 50 nM concentration, and detection probe at 500 nM concentration. For the two assays that included additive EP013 (SEQ ID Nos 47 and 157) was included in the reaction mixture at 600 nM concentration.

The thermal cycling regimen was 95° C. for 10 seconds, 66.5° C. for 10 seconds, and 72° C. for 10 seconds for 20 cycles, followed by 50 cycles at 95° C. for 10 seconds, 65° C. for 10 seconds, 72° C. for 10 seconds, and fluorescent signal detection at 54° C. for 20 seconds. Fluorescence detection from each probe when bound to its target was measured during the annealing phase of the PCR cycles.

Sequences of target, primers and probe utilized in assays with limiting primer having GC rich 3' end were:

```
Excess primer.
                                      (SEQ ID No. 122)
5' GCACAGTTACAGTATTCCAGCAGACTCA Limiting primer.
                                      (SEQ ID No. 123)
5' TCAGTGGTGGCAGTGGTAGTGGTGGC Target for GC rich primer.
                                      (SEQ ID No. 124)
5' GCACAGTTACAGTATTCCAGCAGACTCAAAT

ACAAGAACCTACTGCTAATGCCACCACTAC

CACTGCCACCACTGA

Detection probe.
                                      (SEQ ID No. 125)
5' BHQ-2 TCAGTGGTGGCAGTGGTAGA Quasar 670
```

Sequences for target, primers, and probe utilized in assays with limiting primer having AT rich 3' end were:

```
Excess primer.
                                        (SEQ ID No. 126)
5' CTTTGGCACCAGAGGTGAGC Limiting primer.
                                        (SEQ ID No. 127)
5' GGTGCGTGGGTCCCAGTCTGCAGTTAAG Target for AT rich primer.
                                        (SEQ ID No. 128)
5' GGTGCGTGGGTCCCAGTCTGCAGTTAAGGG

GGCAGGAGTGGCGCTGCTCACCTCTGG

TGCCAAAG

Detection probe.
                                        (SEQ ID No. 129)
5' BHQ-2 GCAGGAGTGGCGCT Quasar 670
```

Sequence of additive EP013 was as follows:

```
Additive EP013.
                                        (SEQ ID No. 56)
5' Dabcyl GGTCAGATGAAAATGATACGTGp Dabcyl CCAGTCTACTTTTACTATGCAC Dabcyl 5'
```

In the assays using the limiting primer having the GC rich 3' end, addition of additive EP013 to the reaction mixture at 600 nM concentration resulted in a delay in the threshold cycle ($C_T$) of 4 cycles as compared to amplification with no additive. In the assays using the limiting primer having the AT rich 3' end, addition of additive EP013 to the reaction mixture at 600 nM concentration resulted in a $C_T$ delay of 11 cycles.

Example 13

Modification of 5' End of Primers and Type III Mispriming

We used additional nucleotides to form a non-complementary tail on the 5' end of one of the PCR amplification primers. In this example we used LATE-PCR amplification, and we modified the limiting primer. We compared modified and unmodified primers to discriminate between fully bound and partially bound 3' ends. Two adenines were added to the 5'-end of the limiting primer used to amplify the human mitochondrial cytochrome b gene (denoted by the underlined bases). We tested two additives: additive EP047, target, primer, and additive sequences were as follows:

```
Target Cytb-1.
                                        (SEQ ID No. 79)
5' TGTGAGGGTGGGACTGTCTACTGAGTAGCCTCCTCAGAT

TCATTGAACTAGGTCTGTCCCAATGTATGGGATGGCGGATA

GTAAGTTTGTAATTACTGTGGCCCCTCAGAATGATATTTGG

CCTCACGGGAGGACATAGCCTATGAAGGCTGTTGCTATAG

TTGCAAGCAGGAGGATAATGCCGATGTTTCAGGTTTCTGA

GTAGAGAAATGATCCGTAATATAGGCCTCGCCCGATGTGT

AGGAAGAGGCAGATAAAGAATATTGAGGCGCCATTGGCG

TGAAGGTAGCGGATGATTCAGCCATAATTTACGTCTCGAG

TGATGTGGGCGATTGATGAAAAGGCGGTTGAGGCGTCTGG

TGAGTAGTGCATGGCTAGGAATAGTCCTGTGGTGATTTGG

AGGATCAGGCAGGCGCCAAGGAGTGAGCCGAAGTTTC

ATCATGCGGA

Limiting Primer.
                                        (SEQ ID No. 80)
5' TGTGAGGGTGGGACTGTCTACTGAGTAGCC Excess Primer.
                                        (SEQ ID No. 81)
5' TCCGCATGATGAAACTTCGGCTC Modified Limiting Primer.
                                        (SEQ ID No. 130)
5' AATGTGAGGGTGGGACTGTCTACTGAGTAGCC Additive EP047.
                                        (SEQ ID No. 131)
Dabcyl CCTCGTCTGATCGTGACTCCAT Dabcyl 5'

5' Dabcyl AGACTAGCACTGAGGTA

Additive EP043.
                                        (SEQ ID No. 48)
5' GGAGCAGACTAGCACTGAGGTA Dabcyl Dabcyl CCTCGTCTGATCGTGACTCCAT Dabcyl 5'

5' Dabcyl AGACTAGCACTGAGGTA Dabcyl
```

Additive EP047 includes a strand 22 nucleotides long and a strand 17 nucleotides long that form a double-stranded region that is 17 nucleotides long, and it has four terminal Dabcyl modifiers. The Tm of additive EP047 is 59.1° C. Additive EP043 is a mixture of additives. It includes as one component additive EP047 (which comprises the two bottom strands), which was included in this test at a concentration of 550 nM. Mixture EP043 also includes another double-stranded oligonucleotide shown as the top two strands. This second oligomer includes two complementary strands that are 22 nucleotides long, and it has three terminal Dabcyl modifiers. It has a Tm of 67.4° C., and it was included in this test at a concentration of 50 nM. Because the two additives in the mixture share a common strand, the strand concentrations were 50/600/550 for the top/middle//bottom strands.

LATE-PCR reaction mixtures included 1×PCR buffer, 250 nM dNTPs, 3 mM MgCl$_2$, 0.24×SYBR Green, 50 nM limiting primer, 1000 nM excess primer, 1000 copies of human mitochondrial DNA, and 2.5 units of TFi(−) DNA polymerase, an antibody-bound, 5' exonuclease (−) polymerase (Invitrogen, Carlsbad Calif.) in 25 ul volume. Six assays were performed, with additives and limiting primers in the reaction mixture as follows:
 (1) no additive, untailed limiting primer (SEQ ID No. 80)
 (2) no additive, tailed limiting primer (SEQ ID No. 133)
 (3) additive EP047 at 600 nM concentration, untailed limiting primer
 (4) additive EP047 at 600 nM concentration, tailed primer
 (5) three-strand additive mixture EP043 at strand concentrations of 50/600/550, untailed primer
 (6) three-strand additive mixture EP043 at strand concentrations of 50/600/550, tailed primer The six reaction mixtures were amplified under the following conditions: 95° C. for 3 minutes followed by 65 cycles of 95°/5 s, 58° C./20 s, and 68° C./2 m. Melt analysis of the products was then conducted, starting at 45° C. with 1° C. increments at 30 s intervals to 95° C. PCR amplification as well as the melt analysis was monitored by the use of SYBR Green.

For the reactions with no additive, product evolution resulted in an amplicon having a Tm above the Tm of the desired product, no matter which limiting primer was used. Including additive EP047 in the reaction mixture delayed the onset of detectable product evolution by several amplification cycles and resulted in a portion of the amplification product being the correct product. With additive EP047, more correct product was made using the tailed primer than was made using the untailed primer. Additive EP047 has a calculated Tm based on its unmodified strands of 59.1° C. Including additive EP043 in the reaction mixture also delayed the onset of detectable product evolution and resulted in the most correct product being generated. With additive EP043, more correct product was made using the tailed primer than was made using the untailed primer. Additive EP043 is a mixture having calculated Tm's base on the unmodified strands of 67.4° C. and 59.1° C.

Figure 15A:
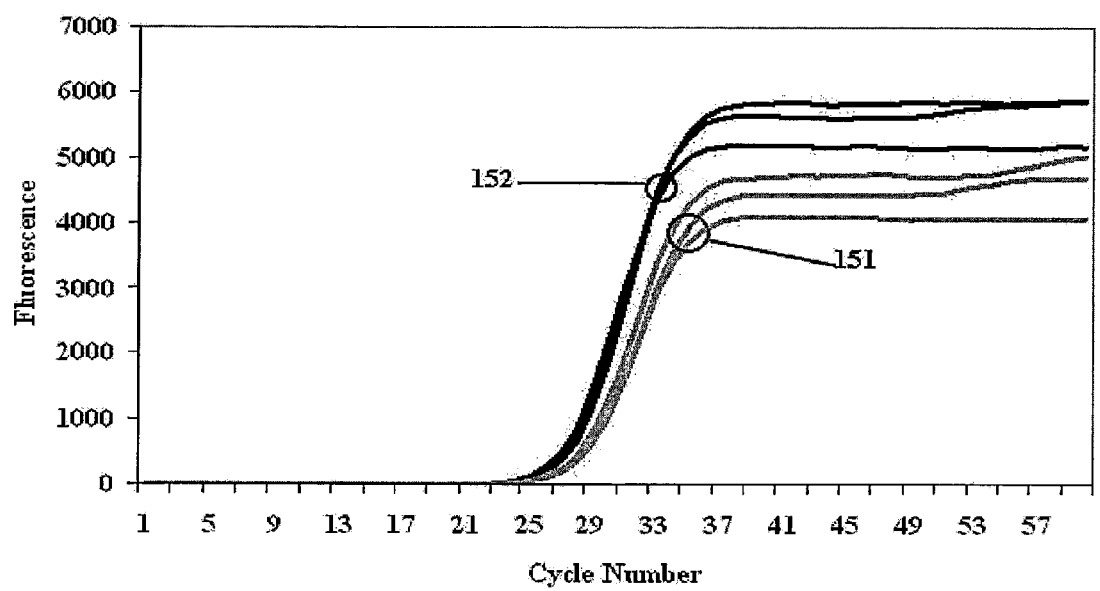
FIG. 15A is a graph of SYBR Green fluorescence as a function of amplification cycle number for replicates of a LATE-PCR amplification described in Example 13 utilizing additive mixture EP043 at a total concentration of 600 nM and strand concentrations of 50/600/550 nM, with untailed primer and tailed primer.
Figure 15B:
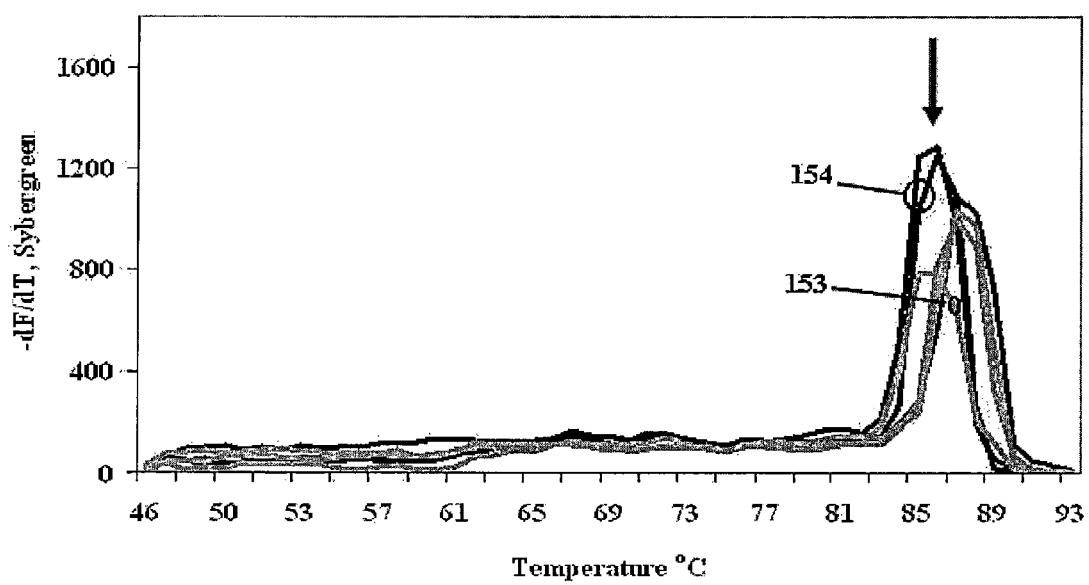
FIG. 15B shows the melt curves of the six amplification products with additive EP043, where the downward pointing arrow indicates the melting temperature, 86° C., of the correct double-stranded DNA product. Circle 153 identifies the one replicate with untailed primer that showed the correct peak with no product evolution (flat plateau) in FIG. 15A, and circle 154 identifies the two replicates with tailed primer also showed no product evolution (flat plateau) in FIG. 15A.

Real-time kinetic curves the six replicates with additive EP043, tailed limiting primer and untailed limiting primer, are shown in FIG. 15A. In FIG. 15A circle 151 (gray lines) identifies the curves for the three replicates with the untailed primer, and circle 152 (black lines) identifies the curves for the replicates with the tailed primer. Melt curves of the six amplification products with additive EP043 are shown in FIG. 15B, where the downward pointing arrow indicates the melting temperature, 86° C., of the correct double-stranded DNA product. In FIG. 15B circle 153 identifies the one replicate with untailed primer that showed the correct peak with no product evolution (flat plateau) in FIG. 15A, and circle 154 identifies the two replicates with tailed primer also showed no product evolution (flat plateau) in FIG. 15A.

Example 14

Additive as Primer for Suppressing Mispriming

A primer that is an additive is a double-stranded oligonucleotide in which one strand is an amplification primer having an extendable 3' end. Its 5' end has a modifier substituent. The other strand, which we refer to as the reverse complement sequence has two, and its 3' end is non-extendable. Because the amplification assay of this example is a LATE-PCR assay in which the limiting primer is included in the reaction mixture a very low concentration, only the excess primer is made an additive. The strand having the free 3' end serves as an amplification primer when it hybridizes to and extends on its target strand, and it serves as an inhibitor of mispriming when it hybridizes to its modified complementary strand. In this example, the primer-reverse complement sequence additive has three terminal Dabcyl modifiers. The primer strand is modified by covalent linkage of a modifying group, here a Dabcyl group, to its 5' terminal nucleotide. The reverse complement sequence is modified by covalent linkage of a modifying group, here a Dabcyl group, to each of its 5' and 3' ends. The Tm of the reverse complement sequence to the primer strand is designed to be 5-30° C., preferably 15-25° C., lower than the Tm of the primer strand to its amplification target sequence. To achieve the difference in Tm's, the reverse complement sequence may be rendered partially complementary to the primer strand by making it either shorter or mismatched at one or more nucleotides. In this example, several mismatched nucleotides were included. In multiplex reactions having more than one pair of primers at least one primer is converted to an additive with its corresponding partially complementary reverse complement sequence. In both monoplex and multiplex reactions the concentration of said at least one oligonucleotide is titrated and optimized empirically to achieve suppression of mispriming together with the lowest scatter among replicate reactions. Typically, said optimum concentration is close to that of a double-stranded additive that is not a primer added to the same reaction to suppress mispriming. As one skilled in the art will understand, reactions utilizing an additive-primer can be further supplemented with an additive that is not a primer, provided the latter does not cross hybridize with the former.

LATE-PCR reactions were carried out in triplicate using the following sequences:

```
Limiting Primer.
                                      (SEQ ID No. 132)
5' TCCAGTACACTTACCATGTTACGACTTGTCTCCTCTA Excess Primer.
                                      (SEQ ID No. 133)
5' Dabcyl AGTTCACCCTCTAAATCACCACGAT Reverse Complement Sequence.
                                      (SEQ ID No. 134)
5' Dabcyl ATCGTTGTGGTATAGAGGGTGAACT-Dabcyl Target.
                                      (SEQ ID No. 135)
5'AGTTCACCCTCTAAATCACCACGATCAAAAGGAACAAGC

ATCAAGCACGCAGCAATGCAGCTCAAAACGCTTAGCCTAGCCA

CACCCCCACGGGAAACAGCAGTGATTAACCTTTAGCAATAAAC

GAAAGTTTAACTAAGCTATACTAACCCCAGGGTTGGTCAATTTCG

TGCCAGCCACCGCGGTCACACGATTAACCCAAGTCAATAGAAGC

CGGCGTAAAGAGTGTTTTAGATCACCCCCTCCCCAATAAAGCTA

AAACTCACCTGAGTTGTAAAAAACTCCAGTTGACACAAAATAGA

CTACGAAAGTGGCTTTAACATATCTGAACACACAATAGCTAAGA

CCCAAACTGGGATTAGATACCCCACTATGCTTAGCCCTAAACCT

CAACAGTTAAATCAACAAAACTGCTCGCCAGAACACTACGAGC

CACAGCTTAAAACTCAAAGGACCTGGCGGTGCTTCATATCCCTC

TAGAGGAGCCTGTTCTGTAATCGATAAACCCCGATCAACCTCAC

CACCTCTTGCTCAGCCTATATACCGCCATCTTCAGCAAACCCTGA

TGAAGGCTACAAAGTAAGCGCAAGTACCCACGTAAAGACGTTAG

GTCAAGGTGTAGCCCATGAGGTGGCAAGAAATGGGCTACATTTTC

TACCCCAGAAAACTACGATAGCCCTTATGAAACTTAAGGGTCGA

AGGTGGATTTAGCAGTAAACTAAGAGTAGAGTGCTTAGTTGAAC

AGGGCCCTGAAGCGCGTACACACCGCCCGTCACCCTCCTCAAGT

ATACTTCAAAGGACATTTAACTAAAACCCCTACGCATTTATATA

GAGGAGACAAGTCGTAACATGGTAAGTGTACTGG
```

LATE PCR amplifications were carried out in 25 ul volume consisting of 1× Platinum Tfi(-) buffer (Invitrogen, Carlsbad, Calif.), 3 mM MgCl$_2$, 250 nM dNTPs, 50 nM of limiting primer, 1000 nM of excess primer, 0.24×SYBR Green (Invitrogen, Carlsbad, Calif.), 2.5 units of Platinum Tfi(-) DNA polymerase (Invitrogen, Carlsbad, Calif.) with approximately 1000 mitochondrial genomes from human genomic DNA. The concentrations of the reverse complement that created the additive were 100, 200 and 300 nM. In this instance we lowered the Tm of the primer-reverse complement hybrid relative to the primer-target hybrid by introducing mismatches into the reverse complement strand (mismatched nucleotides are underlined).

The thermal profile conditions for these reactions were as follows: 95° C. for 3 minutes followed by 95° C./5 s-58° C./20 s-68° C./2 m for 60 cycles, followed by a melt starting at 45° C./45 s with 1° C. increments for 51 cycles. All reactions were analyzed in real time during the extension phase (68° C.) of thermal cycles. At the end of 60 cycles the amplification products were analyzed using the first derivative of SYBR Green fluorescence (melt curve analysis) of double-stranded DNA product.

Figure 16A:
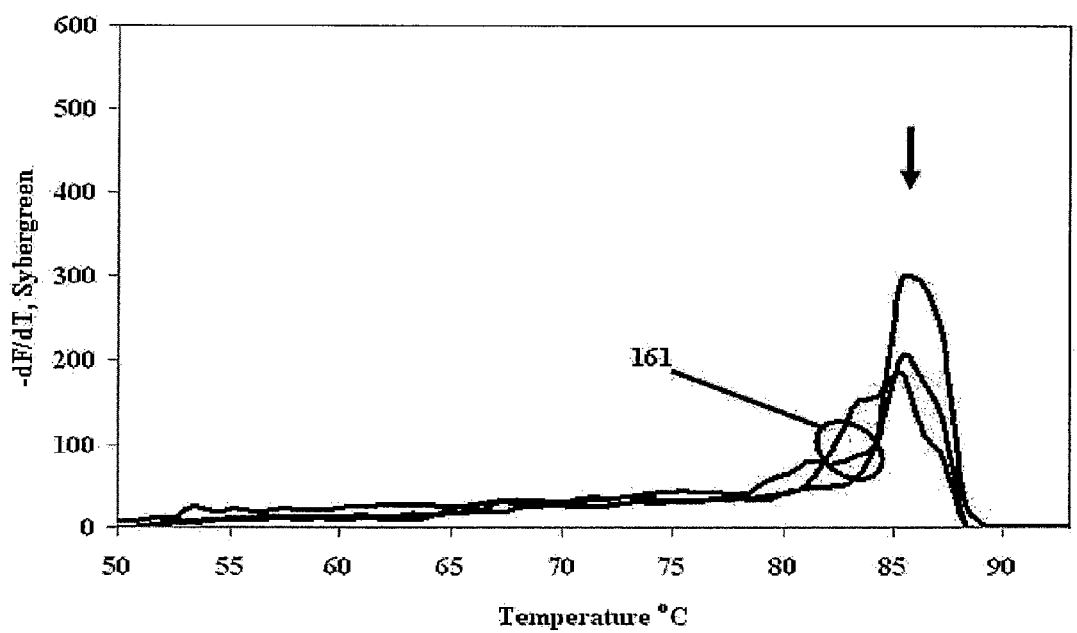
FIG. 16A presents melt curves for replicates of a LATE-PCR amplification described in Example 14 utilizing a 5'-Dabcylated primer but no reverse complement sequence.
Figure 16B:
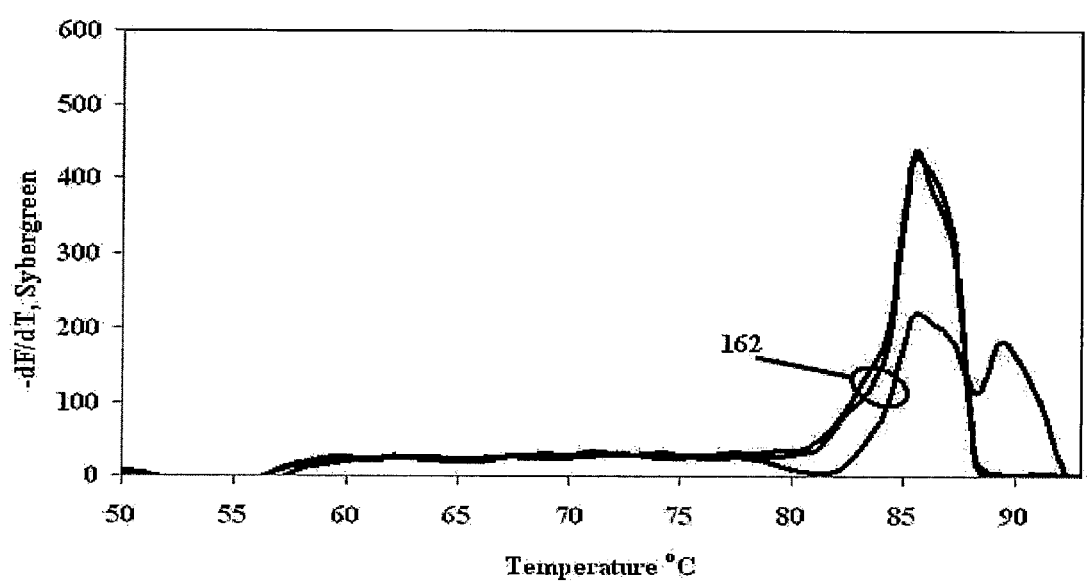
FIG. 16B presents melt curves for replicates of a LATE-PCR amplification described in Example 14 utilizing a 5'-Dabcylated primer plus a reverse complement sequence at a concentration of 100 nM.
Figure 16C:
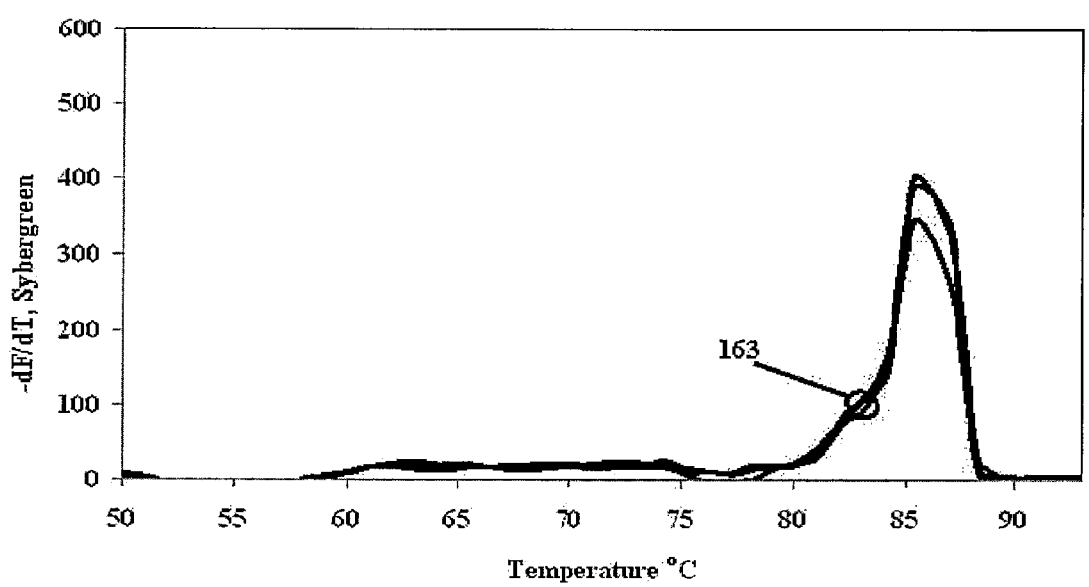
FIG. 16C presents melt curves for replicates of a LATE-PCR amplification described in Example 14 utilizing a 5'-Dabcylated primer plus a reverse complement sequence at a concentration of 200 nM.
Figure 16D:
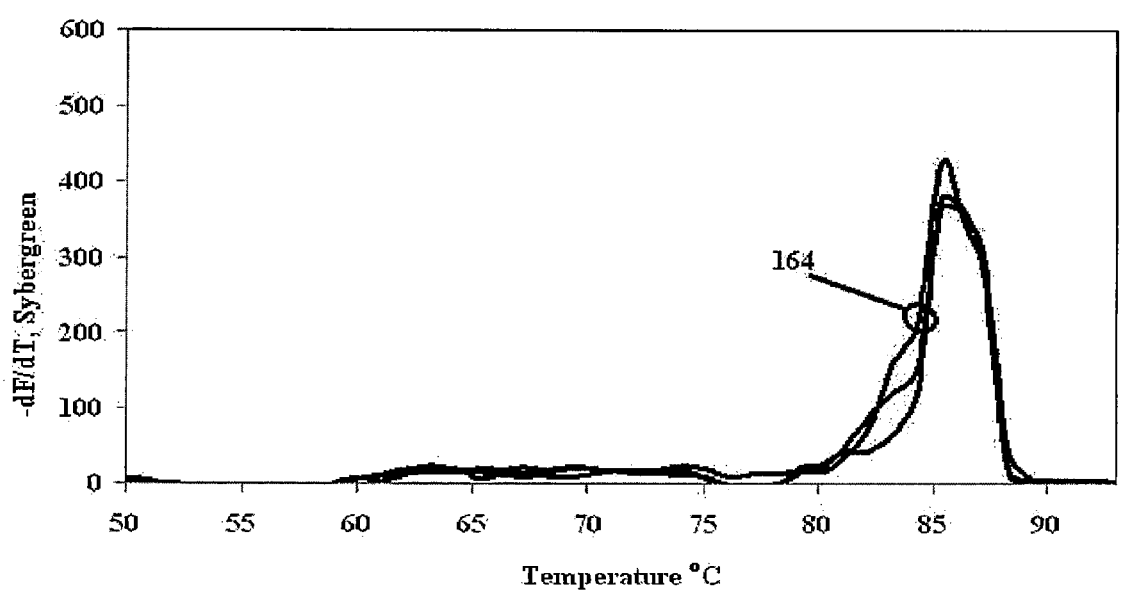
FIG. 16D presents melt curves for replicates of a LATE-PCR amplification described in Example 14 utilizing a 5'-Dabcylated primer plus a reverse complement sequence at a concentration of 300 nM.

The melt curves are presented in FIGS. 16A-16D. FIG. 16A is the melt curves for the three replicates with no reverse complement sequence. Curves 161 show that in the absence of the complementary oligonucleotide only one of three reactions generated the expected product having a melting temperature of 86° C. (arrow). FIG. 16B is the melt curves for the three replicates that included the reverse complement sequence at 100 nM concentration. Curves 162 show that two of three reactions generated the expected product. FIGS. 16C and 16D are the melt curves for the replicates with the reverse complement sequence at concentrations of 200 nM and 300 nM, respectively. Curves 163 and 164 show that all three replicates in each set of reactions generated the correct product (as judged by the presence of a melting peak of 86° C.).

Example 15

Mispriming with RNA Target

This example describes a series of LATE-PCR assays in which the starting target sequence was RNA rather than DNA, so the initial reaction mixtures included reverse transcriptase, and the protocol included an initial incubation to convert RNA to cDNA prior to amplification of the cDNA. The RNA utilized in this series was a sequence within an Enterovirus Armored RNA (EV, Catalog #42050 from Asuragen, Austin, Tex., USA) containing the a portion of the 5' untranslated region (UTR) from the Enterovirus RNA. Samples include primer pairs for both EV and Foot and Mouth Disease Virus (FMDV), but no FMDV targets are included in this example. Amplification reactions were followed in real time by the use of a molecular beacon probe having a fluorophore (Cal Red 610) and a quencher (Black Hole Quencher No. 2). All sets of all reactions were run in triplicate, and products were analyzed via melt curve analysis at end-point.

Several additives, including mixtures, were compared to a no-additive control. Sequences of the EV primers, EV probe and additives were as follows:

```
EV Limiting Primer.
                                    (SEQ ID No. 136)
5' GACTTGCGCGTTACGACAGGCCAATC EV Excess Primer.
                                    (SEQ ID No. 137)
5' TGAATGCGGCTAATCCCAAC EV Probe.
                                    (SEQ ID No. 138)
5' Cal Red 610-AACCACCTGCCCCTT-BHQ2

Additive EP020.
                                    (SEQ ID No. 12)
5' Dabcyl GAAATAAAATAAAAATAAAATA Dabcyl Dabcyl CTTTATTTTATTTTTATTTTAT Dabcyl 5'
```

```
-continued
Additive EP010.
                                    (SEQ ID No. 10)
5' Dabcyl GGTCAGATGAAAATGATACGTG Dabcyl Dabcyl CCAGTCTACTTTTACTATGCAC Dabcyl 5'

Additive EP003.
                                    (SEQ ID No. 25)
5' GGAGCAAAATAGCAATGAGGTA Dabcyl Dabcyl CCTCGTTTTATCGTTACTCCAT Dabcyl 5'
```

EV Armored RNA was diluted in 10 mM TRIS, pH 8.3 to about 25,000 particles per µl and heated at 75° C. for 3 minutes to denature the coat protein and release the RNA. The RNA (2 µl per sample) was mixed with a solution containing the concentrated primers (3 µl per sample) and was incubated at room temperature for 5 minutes, then a concentrated reagent mix was added to yield the following concentrations in a final volume of 25 µl per sample: 3 mM magnesium chloride, 400 nM each deoxynucleotide, 500 nM each probe, 50 nM each limiting primer, 500 nM each excess primer, 1× Tfi (exo-) reaction buffer, 2 Units Tfi (exo-) polymerase per sample (Invitrogen, Cat. No. 60684-050), and 100 Units per sample SuperScript III Reverse Transcriptase (Invitrogen, Cat. No. 18080-044). EV RNA was at about 50,000 copies per sample. Additives were included at the following concentrations:

Reaction A—Additive EP020 at 2000 nM
Reaction B—Additive EP010 at 200 nM
Reaction C—Additive EP003 at 400 nM
Reaction D—Additive EP010 at 400 nM and Additive EP020 at 1000 nM
Reaction E—Additive EP003 at 400 nM and Additive EP020 at 1000 nM
Reaction F—no additive control Samples were placed in a Stratagene MX3005P thermal cycler and incubated at 50° C. for 6 minutes, 95° C. for 1 minute, then 25 cycles of 95° C./10 s, 64° C./10 s, and 68° C./20 s, followed by 35 cycles of 95° C./10 s, 64° C./10 s, 68° C./20 s, and 50° C./30 s with fluorescence detection for probe at 50° C.

Figure 17A:
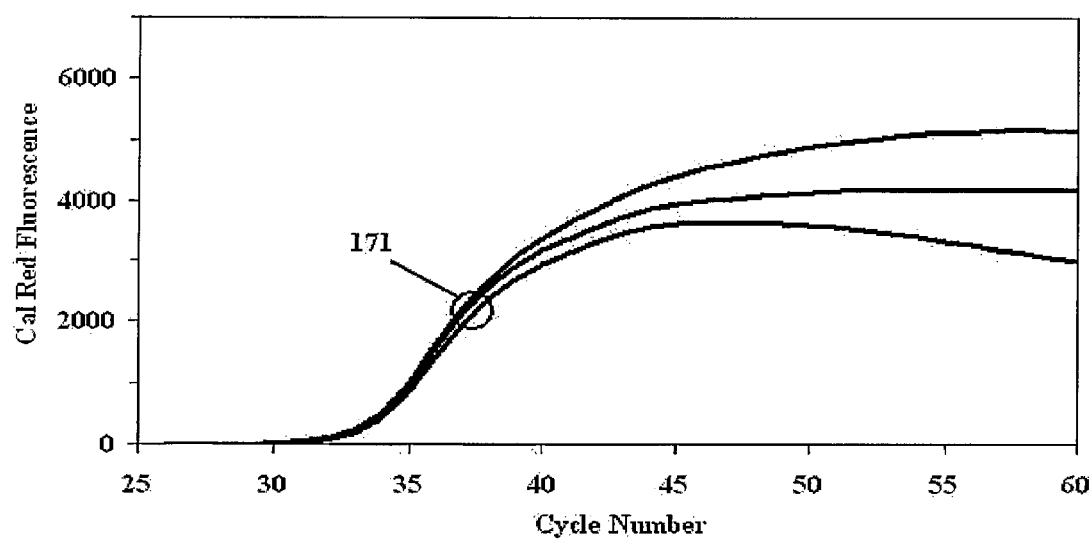
FIG. 17A is a graph of probe fluorescence as a function of cycle number for replicates of a LATE-PCR amplification with reverse transcription for an RNA target, described in Example 15, utilizing additive EP020 at a concentration of 2000 nM.
Figure 17B:
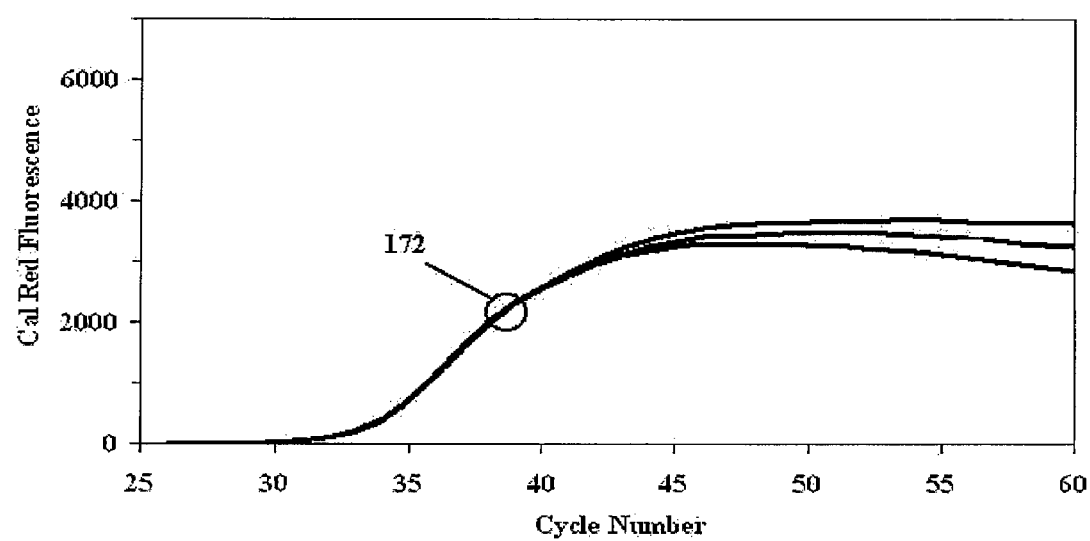
FIG. 17B is a graph of probe fluorescence as a function of cycle number for replicates of a LATE-PCR amplification with reverse transcription for an RNA target, described in Example 15, utilizing additive EP010 at a concentration of 200 nM.
Figure 17C:
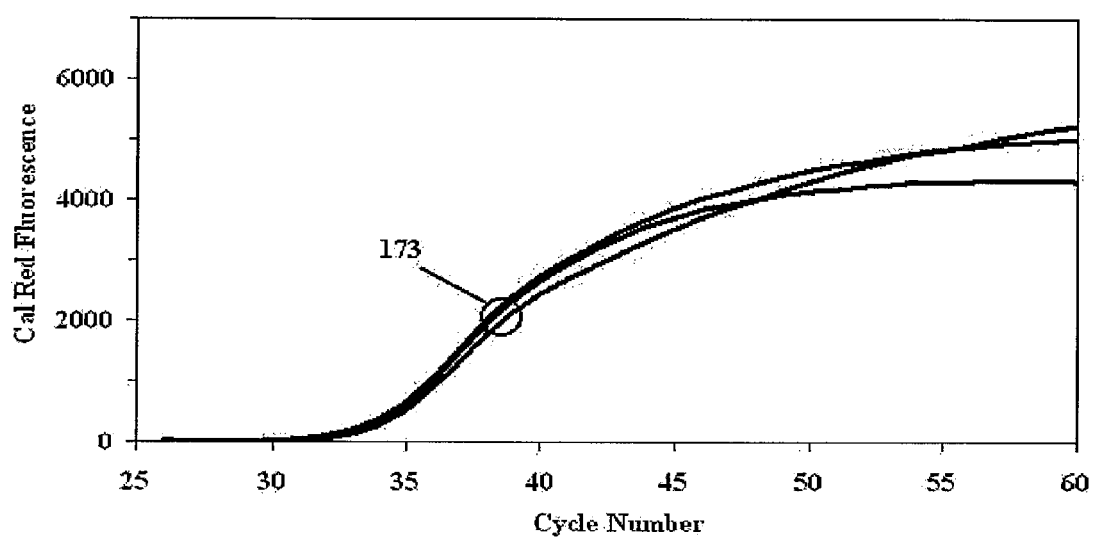
FIG. 17C is a graph of probe fluorescence as a function of cycle number for replicates of a LATE-PCR amplification with reverse transcription for an RNA target, described in Example 15, utilizing additive EP003 at a concentration of 400 nM.
Figure 17D:
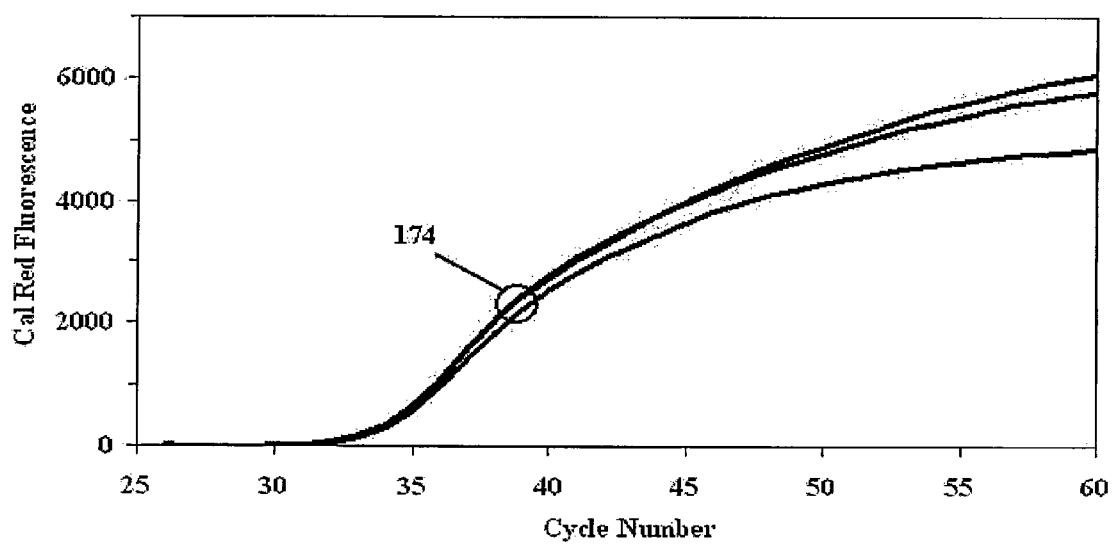
FIG. 17D is a graph of probe fluorescence as a function of cycle number for replicates of a LATE-PCR amplification with reverse transcription for an RNA target, described in Example 15, utilizing an mixture of additive EP010 at a concentration of 400 nM and additive EP020 at a concentration of 1000 nM.
Figure 17E:
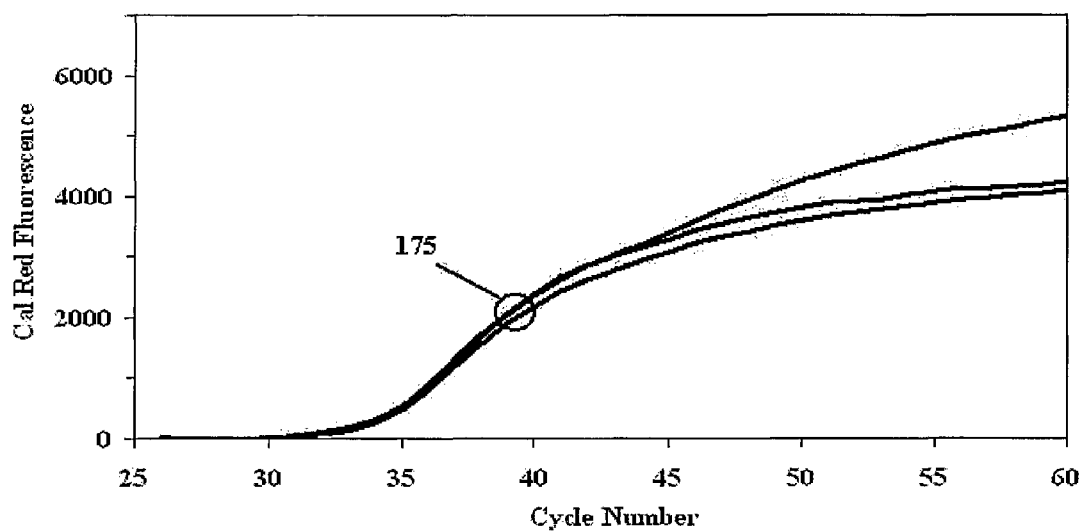
FIG. 17E is a graph of probe fluorescence as a function of cycle number for replicates of a LATE-PCR amplification with reverse transcription for an RNA target, described in Example 15, utilizing a mixture of additive EP003 at a concentration of 400 nM and additive EP020 at a concentration of 1000 nM.
Figure 17F:
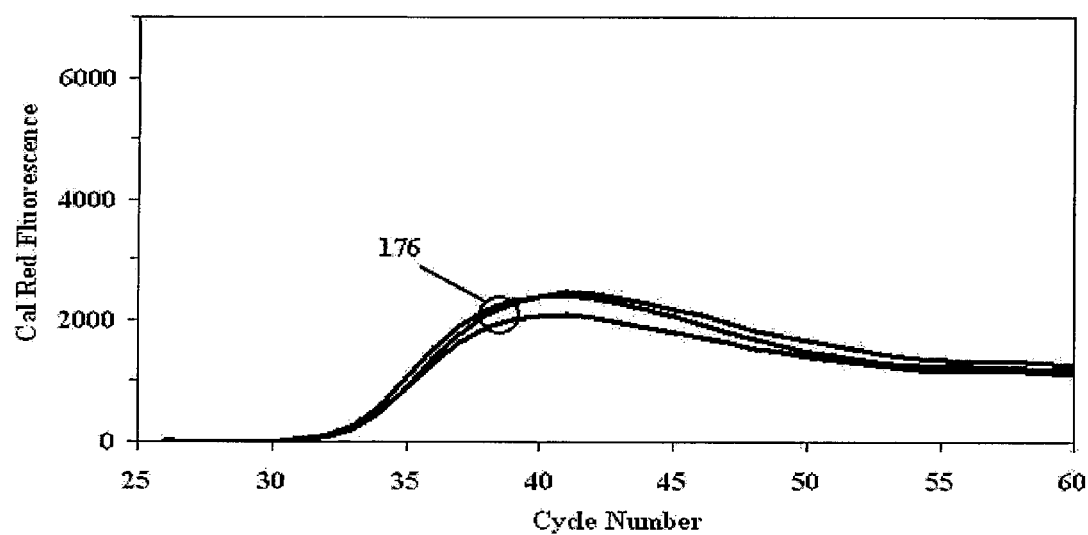
FIG. 17F is a graph of probe fluorescence as a function of cycle number for replicates of a LATE-PCR amplification with reverse transcription for an RNA target, described in Example 15, utilizing no additive.

FIGS. 17A-17F show the real-time results for probe fluorescence during the low-temperature (50° C.) detection step in cycles 26-60. In FIG. 17A, circle 171 is the curves for the three replicates for Reaction A. In FIG. 17B, circle 172 is the curves for the three replicates for Reaction B. In FIG. 17C, circle 173 is the curves for the three replicates for Reaction C. In FIG. 17D, circle 174 is the curves for the three replicates for Reaction D. In FIG. 17E, circle 175 is the curves for the three replicates for Reaction E. In FIG. 17F, circle 176 is the curves for the three replicates for Reaction F.

The curves of circle 176 show that the no-additive control exhibited Type III mispriming (severe product evolution), shown by the reduction of single-stranded product in later amplification cycles (roughly cycles 42-60). The curves of circle 171 for Reaction A, which contained a low-Tm additive (Tm 47.7° C., which was some 16° C. below the annealing temperature and 2.3° C. below the low-temperature detection temperature) in very high concentration, showed suppression of Type 1 mispriming but only partial suppressionn of Type III mispriming, with high scatter among replicates by cycle 60. The curves of circle 172 for Reaction B, which contained an additive having a somewhat higher Tm (Tm 60° C., which was 4° C. below the annealing temperature but above the low-temperature detection temperature) at very low concentration totally suppppressed Type I mispriming and only partially suppressed Type III mispriming (two of three replicates showed some reduction in probe signal by cycle 60), but significantly reduced scatter at cycle 60 nonetheless. Reactions C, D, and E, all of which contained additives showed no reduction in probe signal through cycle 60. Because curves of circle 174 show suppression of Type III mispriming with high signal, indicating minimal reduction in efficiency of the reaction, Reaction D was judged to be optimal for this set of reactions.

Example 16

Direct Quantitative Measure of Suppression of Type I Mispriming by Additives with Overhangs The assay reported here was carried out as described in Example 9 with the following exceptions: (a) a Taq polymerase antibody was present in all samples during the 50° C. incubation step; (b) the incubation step at 50° C. was for 1 minute.

Each additive was comprised of the same two hairpin-forming 34-nucleotide long single-stranded oligomers having the structure of oligomers 194,195 depicted in FIG. 18C, with 1, 2, 3 or 4 ends modified by addition of a Dabcyl moiety. All oligos in which the 3' ends were not blocked by a quencher were blocked by either a phosphate (P) or a three-carbon modifier ($C_3$) to prevent extension. The six nucleotides on the 5' and 3' ends of each single-stranded oligomer were complementary, such that when these ends hybridized to each other they formed a 6-base-pair stem and a 22-nucleotide loop structure. With reference to FIG. 18C, the two 22-nucleotide loops of said additive were complementary, such that when hybridized to each other formed an additive 196 having a 22-base-pair long double-stranded portion 197 with four non-complementary single-stranded 6-base-pair long ends 198, 199, 200, 201. The sequences of the single-stranded oligomers were not randomly assigned but required careful consideration due to the inherent complementarity in the design. The consideration is not to allow the oligomers to form other structures at the temperature in which the loops are engaged, in particular to prevent the arm sequences to remain disengaged from each other as well as not binding to any of the complementary loop sequences of either oligonucleotide. These additive sequences have the ability to remain in a predesigned conformation over a range of temperatures.

In the case of additives in which one or both of the component oligonucleotide strands has the capacity to form a stem-loop structure (see FIGS. 18B, 18C) it is desirable that the melting temperature (Tm) of said stem be higher than the melting temperature of the double-strand of the additive, but not so much higher as to prevent formation of the double-stranded conformation of the additive in a reasonable period of time when the temperature of the reaction is decreased. In this case the calculated Tm of the double-stranded portion of the additives was 59° C., and the calculated Tm of the stem nucleotides was 65° C. These calculations are based on reagent concentrations of 70 mM Na+, 3 mM Mg++ at 50° C. For the double-stranded portion the website (http://dinamelt.bioinfo.rpi.edu/twostate.php) was used, and for the stem the website (http://frontend.bioinfo.rpi.edu/applications/mfold/cgi-bin/dna-form1.cgi) was used. In practice the actual Tm depends on the number of interacting Dabcyls and can increase from the calculated Tm by approximately 4° C.

The following additives were used and sequences that are complementary are underlined.

```
Additive SL02.
                              (SEQ ID Nos 139 and 158)
5' GCGCCTCACGTATCATTTTCATCTGACCAGGCGC (P)

3' Dabcyl GCCTCCGTGCATAGTAAAAGTAGACTGGGGAGGC

Additive SL03.
                              (SEQ ID Nos 140 and 159)
5' GCGCCTCACGTATCATTTTCATCTGACCAGGCGC (P)

3' (P) GCCTCCGTGCATAGTAAAAGTAGACTGGGGAGGC Dabcyl

Additive SL04.
                              (SEQ ID Nos 141 and 160)
5' Dabcyl GCGCCTCACGTATCATTTTCATCTGACCAGGCGC (P)

3' (P) GCCTCCGTGCATAGTAAAAGTAGACTGGGGAGGC Dabcyl

Additive SL05.
                              (SEQ ID Nos 142 and 161)
5' GCGCCTCACGTATCATTTTCATCTGACCAGGCGC Dabcyl 3' Dabcyl GCCTCCGTGCATAGTAAAAGTAGACTGGGGAGGC Additive SL06.
                              (SEQ ID Nos 143 and 162)
5' Dabcyl GCGCCTCACGTATCATTTTCATCTGACCAGGCGC (P)

3' Dabcyl GCCTCCGTGCATAGTAAAAGTAGACTGGGGAGGC

Additive SL07.
                              (SEQ ID Nos 144 and 163)
5' Dabcyl GCGCCTCACGTATCATTTTCATCTGACCAGGCGC
Dabcyl 3' Dabcyl GCCTCCGTGCATAGTAAAAGTAGACTGGGGAGGC Additive SL08.
                              (SEQ ID Nos 145 and 164)
5' Dabcyl GCGCCTCACGTATCATTTTCATCTGACCAGGCGC (C3)

3' Dabcyl GCCTCCGTGCATAGTAAAAGTAGACTGGGGAGGC
Dabcyl

Additive SL09.
                              (SEQ ID Nos 146 and 165)
5' Dabcyl GCGCCTCACGTATCATTTTCATCTGACCAGGCGC
Dabcyl 3' Dabcyl GCCTCCGTGCATAGTAAAAGTAGACTGGGGAGGC
Dabcyl
```

Each reaction was carried out in 25 µl volume in triplicate. The final reaction mixture contained 1×PCR buffer (Invitrogen, Carlsbad, Calif.), 3 mM $MgCl_2$, 250 nM dNTPs, 0.24×SYBR Green (Invitrogen, Carlsbad, Calif.), 1.25 units of both Taq DNA polymerase and Taq DNA polymerase antibody (Invitrogen, Carlsbad, Calif.). Separate reaction mixtures contained 300 nM of each additive and no additive. After the respective combinations of reaction ingredients were mixed and prior to the isothermal incubation at 50° C., all reactions had the overlapping oligonucleotides 1 and 2 (Example 9) added at approximately 100,000 copies each.

The thermal profile conditions for these reactions were as follows: 50° C. for 1 minute followed by incubation on ice then the addition of primers to all reaction mixtures for final concentrations of 50 nM limiting primer and 1 µM excess primer. This was followed by rapid heating to 95° C. for 3 min, then 50 cycles at 98° C./10 s and 72° C./40 s. Each of the samples was analyzed by SYBR Green fluorescence in real-time, and at the end of the run each was subjected to melt curve analysis to confirm that the reaction generated a single product peak of 88° C. as expected for the double-stranded product of the amplification reaction.

The melt-curve analysis with additives SL04, SL07, SL08 and SL09 is shown in FIGS. 19A-19D. The lines identified by circle 210 in each figure are the replicates from the sample with Taq DNA polymerase-plus-antibody. The lines identified by circles 211, 212, 213 and 214 are the replicates with additive SL04, SL07, SL08 and SL09, respectively.

Figure 19D:
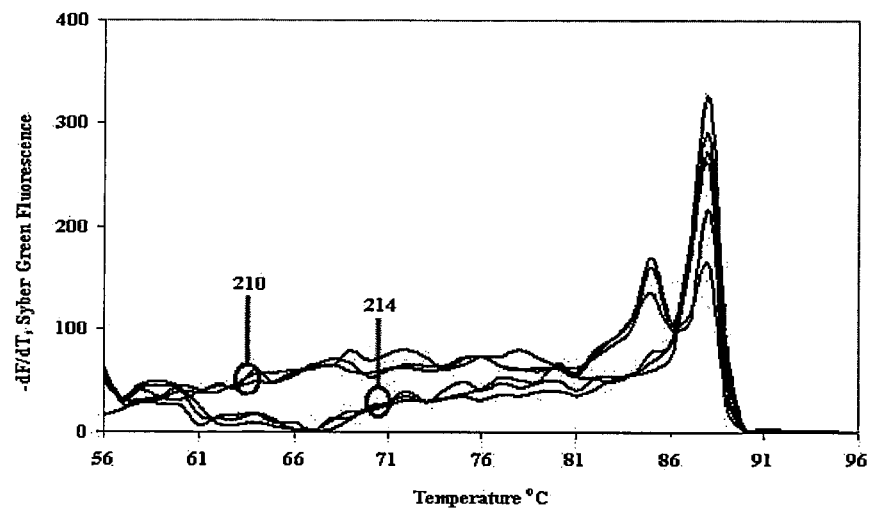
FIG. 19D presents melt curves for products of LATE-PCR amplifications with Taq polymerase plus antibody, with and without additive SL09, as described in Example 16.

The results (see FIG. 19A) confirm that the antibody (circle 210) did not reduce mispriming, because of the presence of two peaks, a low melting peak (i.e., incorrect product, 85° C.) and the correct product at higher peak (88° C.). The results with additives SL04, SL05, SL07 and SL08 show that each additive greatly reduced the amount of incorrect product but did not completely suppress it. FIG. 19D shows that additive SL09, which has 4 Dabcyls, was able to completely suppress the production of the incorrect product.

Example 17

Type II Mispriming and Polymerase Selectivity with Additives Having Overhangs

We performed a LATE-PCR assay described in Example 3 using the additives SL06, SL07, and SL09 (Example 16) at 200 nM, 400 nM, and 600 nM concentrations. These additives contain two, three or four Dabcyl modifiers, respectively.

The LATE-PCR amplifications were carried out in triplicate in 25 µl volume consisting of 1× Invitrogen PCR buffer (Invitrogen, Carlsbad, Calif.), 3 mM $MgCl_2$, 250 nM dNTPs, 50 nM limiting primer, 1000 nM excess primer, 0.24×SYBR Green (Invitrogen, Carlsbad, Calif.), 1.25 units Platinum Taq DNA polymerase (Invitrogen, Carlsbad, Calif.) with approximately 10000 single-stranded target A (matched) or T (mismatched). The thermal profile conditions for these reactions were: 95° C. for 3 minutes followed by 95° C./5 s-62° C./20 s-72° C./30 s for 60 cycles. For this and other assays containing two targets, a control amplification is done using the excess primer, which is perfectly complementary to both targets, and a control limiting primer that is also perfectly complementary to both targets, to ensure that the starting copy numbers of both targets are the same, in which case the $C_T$ for both targets is the same. (If the control amplifications reveal that the starting copy numbers are not the same, one has two choices: either reformulate or, if the $C_T$ difference is slight—as was the case in all examples reported here, correct the observed $C_T$ values to adjust for the difference.)

The results for selectivity ($\Delta C_T$ equals $C_T$ for mismatched target minus $C_T$ for matched target) are shown in Table 7.

TABLE 7

| Additive | Concentration, nM | Selectivity, $\Delta C_T$ |
|---|---|---|
| SL06 (two Dabcyls) | 200 | 1.3 |
| | 400 | 0.8 |
| | 600 | 3.2 |
| SL07 (three Dabcyls) | 200 | 0.8 |
| | 400 | 2.4 |
| | 600 | 2.6 |
| SL09 (four Dabcyls) | 200 | 2.8 |
| | 400 | 4.2 |
| | 600 | 6.8 |

Example 18

Inhibition of Primer-Independent 5' Exonuclease Activity by Additives with Overhangs We performed a LATE-PCR assay as described in detail in Example 6 to determine the efficacy of inhibition of primer-independent 5' exonuclease activity of DNA Taq polymerase using additives with single-stranded overhangs of the type shown in FIG. 18C.

Oscillation reactions were carried out in 25 µl volume consisting of 1×PCR buffer (Invitrogen, Carlsbad, Calif.), 3 mM $MgCl_2$, 200 nM dNTPs, 1.25 units of Taq DNA polymerase (Invitrogen, Carlsbad, Calif.), 200 nM of probe (Example 6), and 100 nM of target (Example 6). This reaction mixture was used without any additive and with each additive at 200 nM, 400 nM, and 600 nM concentrations. A control reaction was run with the probe as the only oligonucleotide in the reaction mixture. The additives (see Example 16) included SL06, which has two Dabcyls; SL07, which has 3 Dabcyls; and SL09, which has 4 Dabcyls. Reaction mixtures were oscillated using the following thermal profile: 45° C./20 s, 60° C./10 s for 45 cycles, followed by a melt starting at 45° C./30 secs with 1° C. increments for 25 cycles. During cycling FAM fluorescence was acquired during the 60° C./10 s segment of the thermal profile.

Exonuclease cleavage activity separates the probe's fluorophore from the probe, thereby resulting in an increase in fluorescence (FAM). Results with additive SL06 are reported in FIG. 20, wherein circle 220 identifies the probe-only control; circle 221 identifies the samples with probe and target but no additive; circle 222 identifies the samples with probe, target and additive SL06 at 200 nM concentration; circle 223 identifies the samples with probe, target and additive SL06 at 400 nM concentration; and circle 224 identifies the samples with probe, target and additive SL06 at 600 nM concentration.

Example 19

Use of a Blocker to Create a 3' Terminal Mismatch

Example 4 above demonstrates the effect of additive mixtures on Type II mispriming and polymerase selectivity in LATE-PCR amplification for a target sequence that is perfectly complementary to the limiting primer as opposed to a mismatched target containing a single base-pair mismatch at the 3' terminal nucleotide of the limiting primer. The present example demonstrates the use of an oligonucleotide, referred to as a "blocker", to prevent the 3' terminus of the limiting primer from hybridizing to a target that is considered to be the mismatched target, that is, the one to be selected against, when the mismatched nucleotide or nucleotides are downstream from the limiting primer binding site. Targets, primers and blocker for the type of assay are depicted generally in FIGS. 21A, 21B.

LATE-PCR amplifications were performed using a limiting primer and an excess primer that were perfectly complementary to the strands of a double-stranded first target and also perfectly complementary to the strands of a double-stranded second target. It was desired that the second target be amplified selectively relative to the first target. The second target contained two base-pair differences from the first target. The first base-pair difference was downstream of the limiting primer binding site and was included in the binding site for a blocker oligonucleotide that was utilized to create a 3' terminal mismatch. The second base-pair difference was downstream of both the limiting primer binding site and the blocker binding site, and the downstream of the excess primer binding site, and was used for probing. The blocker binding site overlapped the limiting primer binding site at the 3' end of the limiting primer, as shown in FIG. 21A.

The blocker used in the LATE-PCR assays was allele-specific so that, due to the first base-pair difference between the targets, it preferentially hybridized to the strand of the first target to which the limiting primer hybridized (see FIG.

21A) rather than the second target (see FIG. 21B). The 5' end of the blocker and the 3' end of the limiting primer were both complementary to the same bases on the first-target strand, but the melting temperature of the blocker, Tm(B), to said strand was higher so that it would bind first as the reaction temperature was lowered during amplification, preventing the 3' terminus of the primer from hybridizing to the first target, creating a 3' terminal mismatch with a perfectly complementary primer. The 3' end of the blocker was itself blocked to prevent extension during amplification. In this instance, the blocker was dual labeled with a fluorophore (Cal Orange 560) on its 5' end and a Dabcyl quencher on its 3' end.

Both LATE-PCR assays also contained an allele-specific probe that hybridizes to the excess primer strand generated from said first target (to the extent that such strands are generated) at a higher melting temperature, Tm(P1), than when hybridized to the excess primer stranded generated from said second target Tm(P2). In this instance the probe was a molecular beacon probe labeled on its 5' end with a Black Hole Quencher 2 (BHQ2) and on its 3' end with a fluorophore (Quasar 670).

The binding of the limiting primer, the allele-specific blocker, and the allele-specific probe to both said first and second targets is illustrated generally in FIGS. 21A and 21B. To effectively block the binding and extension of the limiting primer, the blocker must overlap with the 3' end of the primer at least one nucleotide. The 5' end of the blocker does not have to be a perfect match to the target as long as the blocker binds at a higher temperature than the limiting primer.

Reaction components and reaction conditions were as follows:

```
Limiting Primer:
                                          (SEQ ID NO. 147)
5' GCACTCTTGCCTACGCC Excess Primer:
                                          (SEQ ID NO. 148)
5' CTGGTGGAGTATTTGATAGTG Allele-Specific Blocker:
                                          (SEQ ID NO. 149)
5' Cal Org 560-GCCTACGCCACCAGCTCC-Dabcyl Molecular Beacon Probe:
                                          (SEQ ID NO. 150)
5' BHQ2-CAAGAACATGTCACACATAATG-Quasar 670

Excess Primer Strand of Said First Target:
                                          (SEQ ID NO. 151)
5' CTGGTGGAGTATTTGATAGTGTATTAACCTTATGTGTGACATGTTC

TAATATAGTCACATTTTCATTATTTTTATTATAAGGCCTGCTGAAAATGA

CTGAATATAAACTTGTGGTAGTTGGAGCTGGTGGCGTAGGCAAGAGTGC
```

Excess Primer Strand of Said Second Target (the first base pair change, the change in the blocker binding site, is underlined; the second base pair change, the change in the probe binding site, bolded:

```
                                          (SEQ ID NO. 152)
5' CTGGTGGAGTATTTGATAGTGTATTAACCTTATGTGTCACATGTTC

TAATATAGTCACATTTTCATTATTTTTATTATAAGGCCTGCTGAAAATGA

CTGAATATAAACTTGTGGTAGTTGGAGCTGATGGCGTAGGCAAGAGTGC
```

LATE-PCR amplifications were carried out in 25 ul volume consisting of 1×PCR buffer (Invitrogen, Carlsbad, Calif.), 3 mM $MgCl_2$, 200 nM dNTPs, 50 nM limiting primer, 1000 nM excess primer, 0.24×SYBR Green (Invitrogen, Carlsbad, Calif.), 200 nM probe, 2 units of Taq DNA polymerase (Invitrogen, Carlsbad, Calif.) with different concentrations of plasmid DNA (Epoch Biolabs, Inc, Sugar Land, Tex.) that gave starting copy numbers in the range of $10^0$ to $10^6$, obtained by serial dilution. Amplification reactions were run in a duplicate set for each condition in the presence or absence of 500 nM blocker and either with no additive or with additive EP043 (Example 4) whose strand concentrations (top/middle/bottom) were 33.3 nM, 200 nM and 166.7 nM.

Figure 22A:
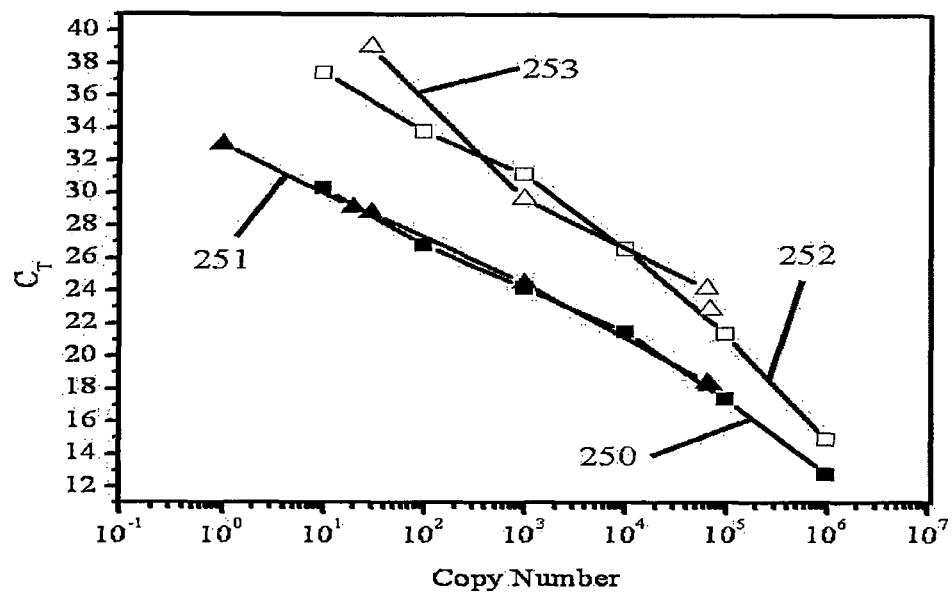
FIG. 22A is a graph of threshold cycle ($C_T$) versus starting concentration of target (Copy Number) for a dilution series of amplifications without blocker as described in Example 19.
Figure 22B:
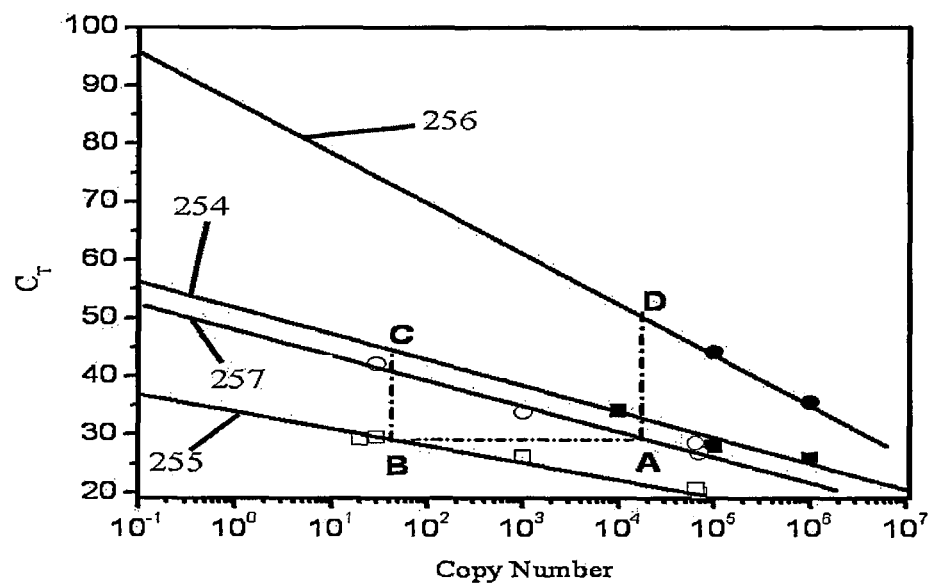
FIG. 22B is a graph of threshold cycle ($C_T$) versus starting concentration of target (Copy Number) for a dilution series of amplifications with blocker as described in Example 19.

The thermal profile conditions for these reactions were as follows: 95° C. for 3 min followed by 70 cycles of 95° C./10 s, 70° C./30 s, 62° C./10 s, 72° C./20 s, followed by a melt starting at 30° C. with 1° C. increments at 30 s intervals to 90° C. SYBR Green signals were detected in real time during the primer extension portion of all PCR cycles, and the $C_T$ values were determined. As the assays were run in duplicate, the two $C_T$ values at each concentration of target were averaged. FIG. 22A presents $C_T$ values as a function of target concentration for assays performed without the blocker, both with and without the EP043 additive. FIG. 22B presents $C_T$ values as a function of target concentration for assays performed with the blocker, both with and without the additive.

Turning to FIG. 22A, filled squares are $C_T$ values of samples with the first target (to be discriminated against through operation of the blocker) at various amounts of starting target (copy number), no blocker and no additive, and the $C_T$ values are connected by line 250; and filled triangles are $C_T$ values of samples with the second target (to be preferentially amplified, because it is mismatched to the blocker), no blocker and no additive, and the $C_T$ values are connected by line 251. Also in FIG. 22A, open squared are $C_T$ values of samples with the first target and additive but no blocker, and the $C_T$ values are connected by line 252; and open triangles are $C_T$ values of samples with the first target and additive but no blocker, and the $C_T$ values are connected by line 253.

Turning to FIG. 22B, filled squares are $C_T$ values of samples with the first target and blocker but no additive, and the $C_T$ values are connected by line 254 (which is extrapolated to low copy numbers); and open squares are $C_T$ values of samples with the second target and blocker but no additive, and the $C_T$ values are connected by line 255 (which is extrapolated to low copy numbers). Also in FIG. 22B, filled circles are $C_T$ values of samples with the first target, blocker and additive, and the $C_T$ values are connected by line 256 (which is extrapolated); and open circles are $C_T$ values of samples with the second target, blocker and additive, and the $C_T$ values are connected by line 257 (which is extrapolated).

Selectivity against the created 3' terminal mismatch in the absence of additive, in this case additive EP043, is the difference between the threshold cycle ($C_T$) of the signal from amplification of said first target at a first concentration and the $C_T$ of the signal from amplification of said second target at said first concentration, and is designated ($\Delta C_{TB}$). Selectivity due to additive EP043 is the double-$C_T$ difference, designated ($\Delta \Delta C_T$), calculated as $\Delta C_{TA}-\Delta C_{TB}$, where $\Delta C_{TA}$ is measured as the difference between the $C_T$ values of said first target and said second target at a second concentration in the presence of both the additive and the blocker, wherein the $C_T$ value of said second target is the same for the reaction containing just the blocker at said first concentration and the reaction containing both the blocker and the additive at said second concentration.

FIG. 22A shows that without the blocker there was no selectivity for either target, as we expected due to the lack of a 3' terminal mismatch between the limiting primer and either target. The data show that without additive EP043, the assay is efficient, as lines 250 and 251 both have slopes of about 3.5. With additive EP043, however, the slopes of lines 252 and 253 are both about 3.9, thereby demonstrating that EP043 decreased PCR amplification for both targets.

For the effect of the additive on selectivity, one turns to FIG. 22B. With the allele-specific blocker but no additive, a mismatched 3' end of the limiting primer is created to said first target, which gives a first selectivity that shows as a $\Delta C_T$ between the $C_T$ of said first target and the $C_T$ of said second target. As shown by lines 254, 255, this $\Delta C_T$ is a function of the concentration of target. With both the blocker and additive EP043, there is another selectivity due to the additive. Because of the inhibition of the PCR amplification reaction by EP043, the $C_T$ difference between the first target and the second target in the presence of EP043 actually includes two factors: 1) the selectivity due to the allele-specific blocker compounded with selectivity due to EP043; and 2) the progressive decrease in efficiency due to EP043 inhibition of PCR.

In order to distinguish and quantify the contribution of these two factors, we did the following with the information in FIG. 22B. At a certain target concentration (copy number), the $C_T$ of a sample with second target, blocker and additive has the value of point A on line 257, and the $C_T$ of a sample with first target, blocker and additive has the value of point D on line 256. These $C_T$ values are 35 and 62, respectively, giving sample a $\Delta C_{TA}$ of 27. However, the $C_T$ value of point A is the $C_T$ value of point B on line 255 (same target, that is, second target, without additive EP043). The concentration of second target at point B is the effective target concentration in the presence of EP043 because of its inhibition of amplification. At the concentration of point B, the $\Delta C_{TB}$ is the segment BC, which is 17. Without additive EP043, this selectivity between said first target and said second target is due to the allele-specific blocker. In order to remove the inhibitory effect of the additive EP043 from $\Delta C_{TA}$, the $\Delta C_{TB}$ at said first concentration of target, 17, is subtracted from the $\Delta C_{TA}$ at the said second concentration of target, 27. This gives the $\Delta\Delta CT$ of 10. The $\Delta\Delta CT$ of 10 is the selectivity effect of additive EP043 in the presence of induced-Type II mis-priming at the target concentration of point A. As can be seen from the FIG. 22B, the magnitude of the selectivity effect of additive EP043 depends on the target concentration, because lines 254, 255, 256, 257 are not parallel to one another. The lower the target concentration, the greater is the selectivity effect of the additive. This is the case, because more thermal cycles are required to detect the product.

Example 20

Suppression of Type I Mispriming on Ice Prior to Amplification

The assay reported here was carried out as described in Example 9 with the following exceptions: (a) the incubation step at 50° C. was for 1 minute; (b) the number of amplifications cycles was reduced to 50; (c) EP010, described in Example 10, was used as the additive; (d) the concentration of the additive was 300 nM.

Figure 23A:
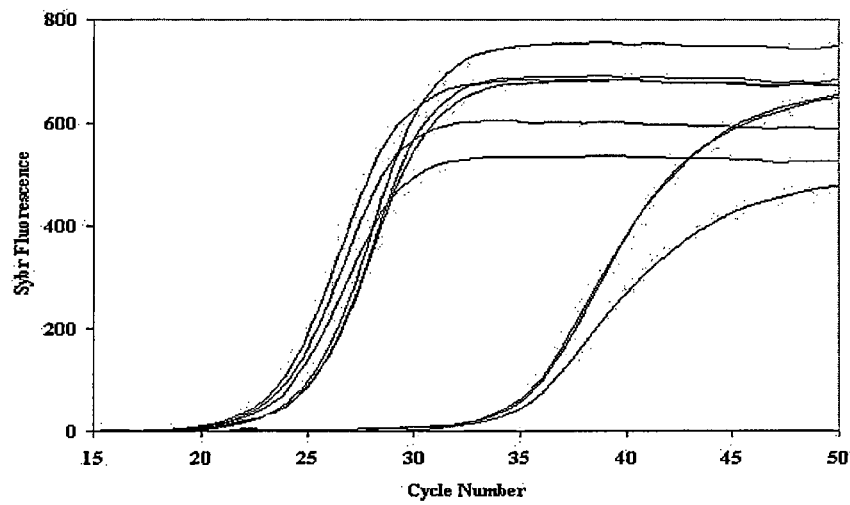
FIG. 23A is a graph of SYBR Green fluorescence versus amplification Cycle Number showing the effect of antibody in amplifications described in Example 20.

SYBR Green fluorescence of the double-stranded products generated in these amplification reactions is shown in FIG. 23A, where circle 260 identifies the replicates from the sample with Taq DNA polymerase only, circle 261 identifies the replicates from the sample with Taq DNA polymerase and antibody added immediately after the isothermal extension step, circle 262 identifies the replicates from the sample with Taq DNA polymerase-plus-antibody present during the isothermal extension step.

FIG. 23A shows the effect of antibody on extension of the overlapping oligonucleotides. The replicate samples without any antibody (circle 260) had a $C_T$ value of 22, and, therefore, extension of the overlapping templates was efficient. In contrast, extension of the overlapping templates is extensively inhibited when the antibody is added prior to the 50° C. incubation step (circle 262). When addition of the antibody is delayed until the end of the 50° C. incubation (circle 261), the $C_T$ is higher than in the no-antibody case (circle 260). This means that most, but not all, of the possible overlapping templates were extended during the 1-minute incubation at 50° C. Additional overlapping templates are extended during the subsequent incubation on ice.

Figure 23B:
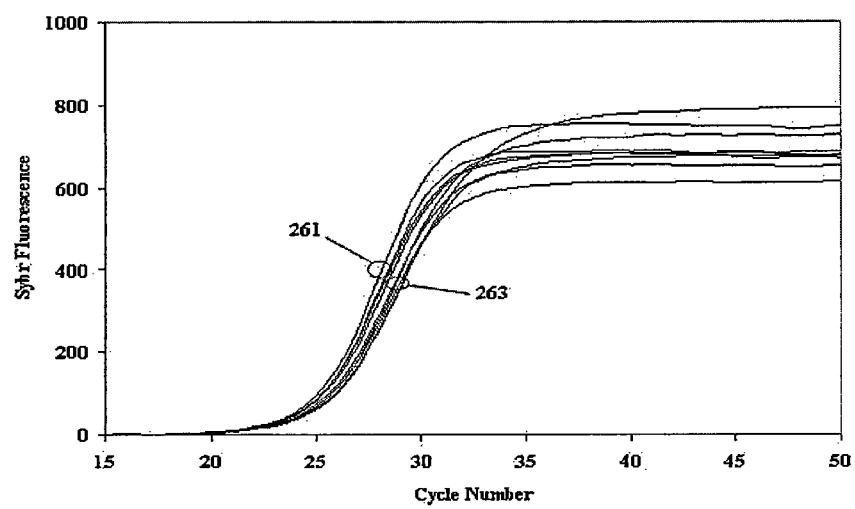
FIG. 23B is a graph of SYBR Green fluorescence versus amplification Cycle Number showing the effect of additive EP010 in amplifications described in Example 20.

FIG. 23B shows the effect of additive EP010 on extension of the overlapping oligonucleotides. Replicates with EP10 (circle 263) received additive EP010 either prior to incubation at 50° C. or after incubation at 50° C. The results (combined as circle 263) show no difference in amplification when EP010 is added before or after the incubation step. This demonstrates that EP010 does not inhibit polymerization during the incubation at the 50° C. step. However, the $C_T$ values are slightly higher than $C_T$ replicates that received the antibody at the end of the 50° C. step (circle 261). This demonstrates that addition of additive EP010 is slightly more effective than the antibody in inhibiting the extension of the overlapping oligonucleotides on ice.

Figure 23C:
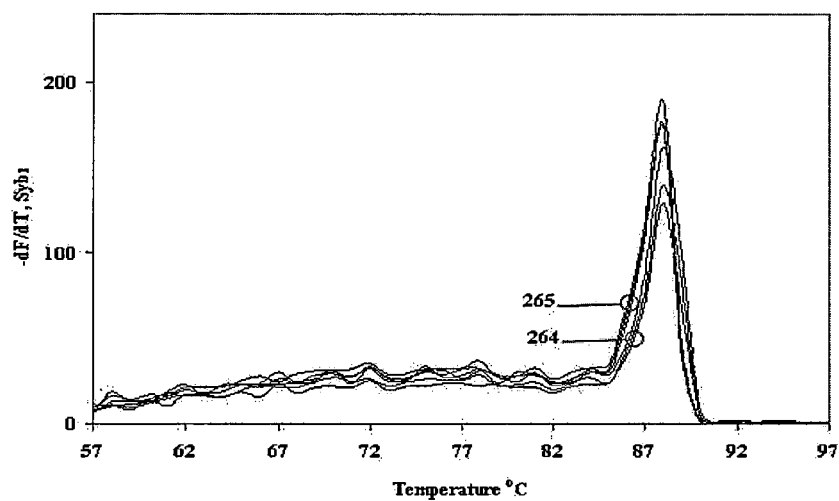
FIG. 23C is melt curves of products described in Example 20 made with DNA polymerase only and product made with antibody added after the first incubation step of the assay.
Figure 23D:
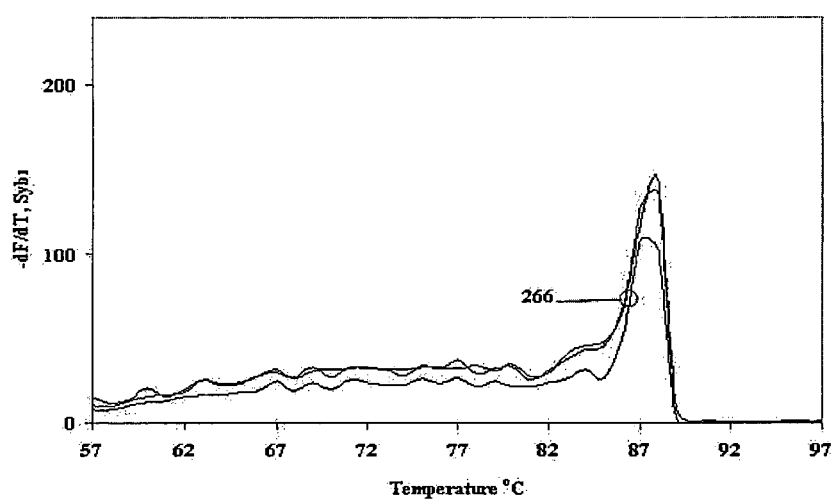
FIG. 23D is melt curves of product described in Example 20 made with antibody added prior to the first incubation step of the assay.
Figure 23E:
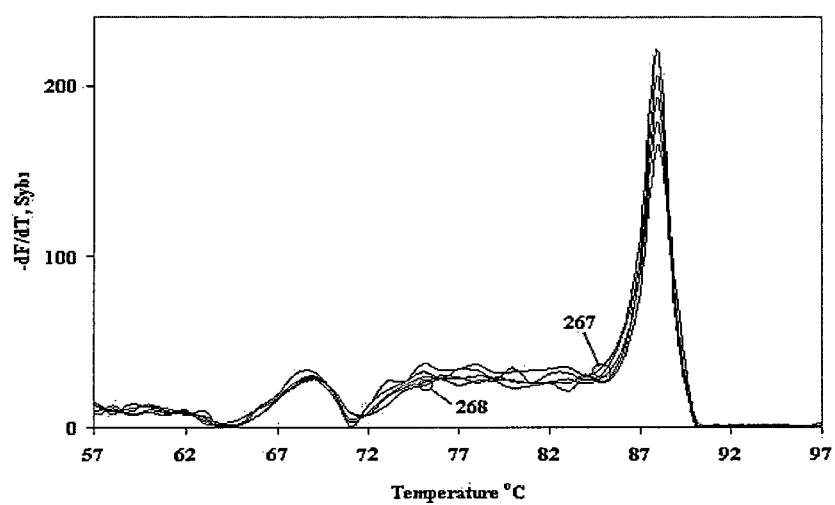
FIG. 23E is melt curves of products described in Example 20 made with additive EP010 added before and after the first incubation step of the assay.

FIG. 23C shows the SYBR Green melt curves of the double-strand product generated in replicates with Taq DNA polymerase only (circle 264) and in replicates with Taq DNA polymerase and antibody added immediately after the extension step (circle 265). FIG. 23D shows the SYBR Green melt curve of the double-stranded product generated in replicates with Taq DNA polymerase-plus-antibody during extension step (circle 266). FIG. 23E shows the SYBR Green melt curves (circle 267) of the double-stranded product generated in replicates that received additive EP010 either prior to incubation at 50° C. (circle 267) or after incubation at 50° C. (circle 268, only two replicates, as one was lost).

FIG. 23C demonstrates that omission of the antibody entirely (circle 264) or omission of the antibody during incubation of the templates at 50° C. (circle 265) results in extension and subsequent amplification of a fairly clean product that melts at 88° C. FIG. 23D demonstrates, in contrast, that inclusion of the antibody during the incubation at 50° C. (circle 266) results in a mixture of products with peaks at 88° C. and 85° C. FIG. 23E demonstrates that addition of the EP010 additive either before or after the 50° C. step results amplification of a clean double-stranded product with a sharp melting peak at 88° C. The melt curves in FIG. 23E also show the presence of a small broad peak at 67-71° C. This peak is due to melting of the double-stranded form of EP010. It shows that the double-stranded form is no longer present at 72° C., the temperature at which extension was carried out during the amplification phase of these reactions and in Example 9. In contrast, the additives used in Example 9 were found to have melt peaks (not shown) that are higher than that of EPO10.

The specific embodiments described above are not exhaustive and should not be construed as limiting the claims. Various modifications of these embodiments can be made without departing from the the concepts described herein. Such modifications are intended to fall within the scope of the claims.

What is claimed is:

1. A reaction mixture for a primer-dependent DNA amplification reaction including primer extension by a DNA polymerase for amplifying at least one DNA target sequence, said reaction mixture comprising:
   (a) at least one primer pair;
   (b) a DNA polymerase;
   (c) dNTPs; and
   (d) at least one double-stranded oligonucleotide additive:
      (i) comprising two separate strands, each of the strands 6-50 nucleotides long;
      (ii) that is at least fifty percent double-stranded at 32° C.; and
      (iii) that has a terminal region on each end of its two separate strands and includes 1-4 modifying groups, each covalently attached to a different terminal region, said modifying groups being polycyclic moieties that do not have bulky portions that are non-planar,
   wherein said at least one double-stranded oligonucleotide additive is present in the reaction mixture at a concentration sufficient to suppress mispriming of an amplification reaction performed using the reaction mixture.

2. The amplification reaction mixture of claim 1 wherein the 1-4 modifying groups is 2-4 modifying groups.

3. The amplification reaction mixture of claim 2 wherein the 2-4 modifying groups is three modifying groups.

4. The amplification reaction mixture of claim 3 wherein the additive includes a first strand that is a primer or probe for said at least one target sequence and a reverse complement strand that is partially complementary to the first strand.

5. The amplification reaction mixture of claim 2 wherein the 2-4 modifying groups is four modifying groups.

6. The amplification reaction mixture of claim 1 wherein the modifying groups are covalently linked to terminal nucleotides of said at least one double-stranded oligonucleotide additive.

7. The amplification reaction mixture of claim 1 wherein the modifying groups are Dabcyl.

8. The amplification reaction mixture of claim 2 wherein the at least one additive is a mixture of two additives.

9. The amplification reaction mixture of claim 8 wherein the mixture of two additives consists of three strands.

10. The amplification reaction mixture of claim 1, wherein the at least one double-stranded oligonucleotide additive consists of natural nucleotides.

11. The amplification reaction mixture of claim 1 wherein the at least one double-stranded oligonucleotide additive is DNA.

12. The amplification reaction mixture according to claim 1 wherein the at least one additive is not a primer or probe for said at least one target sequence.

13. The amplification reaction mixture according to claim 1 wherein the concentration of said at least one double-stranded oligonucleotide additive is not more than 1000 nM.

14. The amplification reaction mixture according to claim 1, further including a reverse transcriptase.

15. The amplification reaction mixture of claim 1 wherein the at least one double-stranded additive includes from one to four single-stranded overhangs.

16. The amplification reaction mixture of claim 15 wherein the at least one double-stranded additive comprises at least one strand that, when not hybridized, forms a stem-loop structure.

17. A method for amplifying at least one DNA target sequence comprising contacting said at least one DNA target sequence with an amplification reaction mixture according to claim 1 and subjecting the reaction mixture to a primer-dependent DNA amplification reaction having a primer annealing temperature and a primer extension temperature.

18. A modified double-stranded oligonucleotide comprising two separate strands, each of the strands 6-50 nucleotides long, that is at least fifty percent double-stranded at 32° C., that has a terminal region on each end of its two separate strands, and that includes 2-4 modifying groups, each covalently attached to a different terminal region, said modifying groups being polycyclic moieties that do not have bulky portions that are non-planar, said modified oligonucleotide being capable of inhibiting the 5' exonuclease domains of DNA polymerases.

19. The modified oligonucleotide of claim 18 wherein the double-stranded oligonucleotide is DNA.

20. The modified oligonucleotide of claim 18 wherein said modifying groups are attached to terminal nucleotides.

\* \* \* \* \*